United States Patent
Rebar

(10) Patent No.: US 10,648,001 B2
(45) Date of Patent: *May 12, 2020

(54) METHOD OF TREATING MUCOPOLYSACCHARIDOSIS TYPE I OR II

(71) Applicant: Sangamo BioSciences, Inc., Richmond, CA (US)

(72) Inventor: Edward J. Rebar, Richmond, CA (US)

(73) Assignee: Sangamo Therapeutics, Inc., Richmond, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/872,537

(22) Filed: Oct. 1, 2015

(65) Prior Publication Data

US 2016/0060656 A1    Mar. 3, 2016

Related U.S. Application Data

(63) Continuation-in-part of application No. 13/839,336, filed on Mar. 15, 2013, now Pat. No. 9,877,988.

(60) Provisional application No. 62/089,070, filed on Dec. 8, 2014, provisional application No. 62/058,400, filed on Oct. 1, 2014, provisional application No. 61/704,072, filed on Sep. 21, 2012, provisional application No. 61/670,463, filed on Jul. 11, 2012.

(51) Int. Cl.
| | |
|---|---|
| *A01N 63/00* | (2020.01) |
| *C12N 15/90* | (2006.01) |
| *C12N 9/22* | (2006.01) |
| *A61K 38/46* | (2006.01) |
| *A61K 38/47* | (2006.01) |
| *A61K 35/407* | (2015.01) |
| *A61K 48/00* | (2006.01) |

(52) U.S. Cl.
CPC .......... *C12N 15/907* (2013.01); *A61K 35/407* (2013.01); *A61K 38/465* (2013.01); *A61K 38/47* (2013.01); *A61K 48/005* (2013.01); *C12N 9/22* (2013.01); *C12Y 301/06013* (2013.01); *C12Y 302/0102* (2013.01); *C12Y 302/01021* (2013.01); *C12Y 302/01022* (2013.01); *C12Y 302/01076* (2013.01); *A61K 48/00* (2013.01); *C07K 2319/81* (2013.01)

(58) Field of Classification Search
USPC .................. 435/325; 424/93.21, 93.2; 514/44
See application file for complete search history.

(56) References Cited

U.S. PATENT DOCUMENTS

| | | |
|---|---|---|
| 5,356,802 A | 10/1994 | Chandrasegaran |
| 5,436,150 A | 7/1995 | Chandrasegaran |
| 5,487,994 A | 1/1996 | Chandrasegaran |
| 5,789,538 A | 8/1998 | Rebar et al. |
| 5,925,523 A | 7/1999 | Dove et al. |
| 6,007,988 A | 12/1999 | Choo |
| 6,013,453 A | 1/2000 | Choo |
| 6,140,081 A | 10/2000 | Barbas |
| 6,140,466 A | 10/2000 | Barbas, III et al. |
| 6,200,759 B1 | 3/2001 | Dove et al. |
| 6,242,568 B1 | 6/2001 | Barbas, III et al. |
| 6,410,248 B1 | 6/2002 | Greisman et al. |
| 6,453,242 B1 | 9/2002 | Eisenberg et al. |
| 6,479,626 B1 | 11/2002 | Kim et al. |
| 6,503,717 B2 | 1/2003 | Case et al. |
| 6,534,261 B1 | 3/2003 | Cox, III et al. |
| 6,599,692 B1 | 7/2003 | Case et al. |
| 6,607,882 B1 | 8/2003 | Cox, III et al. |
| 6,689,558 B2 | 2/2004 | Case |
| 6,723,551 B2 | 4/2004 | Ding et al. |
| 6,794,136 B1 | 9/2004 | Eisenberg et al. |
| 6,824,978 B1 | 11/2004 | Cox, III et al. |
| 6,903,185 B2 | 6/2005 | Kim et al. |
| 6,933,113 B2 | 8/2005 | Case et al. |
| 6,979,539 B2 | 12/2005 | Cox, III et al. |
| 7,013,219 B2 | 3/2006 | Case et al. |
| 7,030,215 B2 | 4/2006 | Liu et al. |
| 7,067,317 B2 | 6/2006 | Rebar et al. |
| 7,070,934 B2 | 7/2006 | Cox, III et al. |
| 7,153,949 B2 | 12/2006 | Kim et al. |
| 7,163,824 B2 | 1/2007 | Cox, III et al. |
| 7,253,273 B2 | 8/2007 | Collingwood |
| 7,262,054 B2 | 8/2007 | Jamieson et al. |
| 7,361,635 B2 | 4/2008 | Miller et al. |
| 7,888,121 B2 | 2/2011 | Urnov et al. |
| 7,914,796 B2 | 3/2011 | Miller et al. |
| 7,951,925 B2 | 5/2011 | Ando et al. |
| 7,972,854 B2 | 7/2011 | Miller et al. |
| 8,034,598 B2 | 10/2011 | Miller |
| 8,110,379 B2 | 2/2012 | DeKelver et al. |

(Continued)

FOREIGN PATENT DOCUMENTS

| | | |
|---|---|---|
| GB | 2338237 | 12/1999 |
| WO | WO 95/19431 | 7/1995 |

(Continued)

OTHER PUBLICATIONS

Luo (Nature Biotechnol., 2000, vol. 18, p. 33-37).*
Pfeifer (Annu. Rev. Genomics. Hum. Genet. 2001, vol. 2, p. 177-211.*
Johnson-Saliba (Curr. Drug. Targets, 2001, vol. 2, p. 371-399).*
Shoji (Current Pharmaceutical Design, 2004, vol. 10, p. 785-796).*
Bibikova (Mol. Cellular Biol., 2001, vol. 21, No. 1, p. 289-297).*
Edelstein (Journal Gene Med., 2004, vol. 6, p. 597-602).*
High (Nature, 2005, vol. 435, p. 577 and 579).*

(Continued)

*Primary Examiner* — Michael C Wilson
(74) *Attorney, Agent, or Firm* — Pasternak Patent Law

(57) ABSTRACT

Nucleases and methods of using these nucleases for inserting a sequence encoding a therapeutic protein such as an enzyme into a cell, thereby providing proteins or cell therapeutics for treatment and/or prevention of a lysosomal storage disease.

4 Claims, 15 Drawing Sheets

Specification includes a Sequence Listing.

(56) References Cited

U.S. PATENT DOCUMENTS

| | | | |
|---|---|---|---|
| 8,329,986 B2 | 12/2012 | Butler et al. | |
| 8,409,861 B2 | 4/2013 | Guschin et al. | |
| 8,563,314 B2 | 10/2013 | Gregory et al. | |
| 8,586,526 B2 | 11/2013 | Gregory et al. | |
| 8,623,618 B2 | 1/2014 | Doyon et al. | |
| 8,697,359 B1 | 4/2014 | Zhang | |
| 8,771,985 B2* | 7/2014 | Cui | C12N 9/22 435/196 |
| 8,772,453 B2 | 7/2014 | Paschon et al. | |
| 8,823,618 B2 | 9/2014 | Lee et al. | |
| 8,895,264 B2* | 11/2014 | Cost | C12N 9/96 435/366 |
| 8,932,814 B2 | 1/2015 | Cong et al. | |
| 8,945,868 B2 | 2/2015 | Collingwood et al. | |
| 8,956,828 B2 | 2/2015 | Bonini et al. | |
| 9,005,973 B2 | 4/2015 | Cost et al. | |
| 9,045,763 B2 | 6/2015 | DeKelver et al. | |
| 9,222,105 B2* | 12/2015 | Cost | C12N 9/96 |
| 2003/0232410 A1 | 12/2003 | Liljedahl et al. | |
| 2005/0026157 A1 | 2/2005 | Baltimore et al. | |
| 2005/0064474 A1* | 3/2005 | Urnov | C07K 14/43595 435/6.18 |
| 2005/0208489 A1* | 9/2005 | Carroll | A01K 67/0339 435/6.16 |
| 2005/0267061 A1 | 12/2005 | Martin | |
| 2006/0063231 A1 | 3/2006 | Li et al. | |
| 2006/0153826 A1* | 7/2006 | Arnould | A01K 67/0275 424/94.61 |
| 2006/0188987 A1 | 8/2006 | Guschin et al. | |
| 2007/0218528 A1 | 9/2007 | Miller | |
| 2008/0131962 A1 | 6/2008 | Miller | |
| 2008/0159996 A1 | 7/2008 | Ando et al. | |
| 2008/0299580 A1 | 12/2008 | DeKelver et al. | |
| 2009/0068164 A1 | 3/2009 | Barbas et al. | |
| 2009/0117617 A1 | 5/2009 | Holmes et al. | |
| 2010/0047805 A1 | 2/2010 | Wang | |
| 2010/0218264 A1 | 8/2010 | Cui et al. | |
| 2011/0041195 A1 | 2/2011 | Doyon | |
| 2011/0189776 A1 | 8/2011 | Terns et al. | |
| 2011/0201055 A1 | 8/2011 | Doyon et al. | |
| 2011/0207221 A1 | 8/2011 | Cost et al. | |
| 2011/0265198 A1 | 10/2011 | Gregory et al. | |
| 2011/0301073 A1 | 12/2011 | Gregory et al. | |
| 2012/0017290 A1 | 1/2012 | Cui et al. | |
| 2012/0128635 A1 | 5/2012 | Gregory et al. | |
| 2013/0122591 A1 | 5/2013 | Cost et al. | |
| 2013/0137104 A1 | 5/2013 | Cost et al. | |
| 2013/0177960 A1 | 7/2013 | Rebar | |
| 2013/0177983 A1 | 7/2013 | Rebar | |
| 2013/0280222 A1 | 10/2013 | Kay et al. | |
| 2015/0056705 A1 | 2/2015 | Conway et al. | |

FOREIGN PATENT DOCUMENTS

| | | |
|---|---|---|
| WO | WO 96/06166 | 2/1996 |
| WO | WO 98/37186 | 8/1998 |
| WO | WO 98/53057 | 11/1998 |
| WO | WO 98/53058 | 11/1998 |
| WO | WO 98/53059 | 11/1998 |
| WO | WO 98/53060 | 11/1998 |
| WO | WO 98/54311 | 12/1998 |
| WO | WO 00/27878 | 5/2000 |
| WO | WO 01/60970 | 8/2001 |
| WO | WO 01/88197 | 11/2001 |
| WO | WO 02/007752 A2 | 1/2002 |
| WO | WO 02/016536 | 2/2002 |
| WO | WO 02/077227 | 10/2002 |
| WO | WO 02/099084 A2 | 12/2002 |
| WO | WO 03/016496 A2 | 2/2003 |
| WO | WO 07/014275 A2 | 2/2007 |
| WO | WO 09/054985 A1 | 4/2009 |
| WO | WO 10/079430 | 7/2010 |
| WO | WO 10/117464 A1 | 10/2010 |
| WO | WO 11/011767 A1 | 1/2011 |
| WO | WO 11/097036 A1 | 8/2011 |
| WO | WO 11/100058 A1 | 8/2011 |
| WO | WO 12/015938 A2 | 2/2012 |
| WO | WO 13/044008 A2 | 3/2013 |
| WO | 2013063315 A2 | 5/2013 |
| WO | 2013158309 A2 | 10/2013 |

OTHER PUBLICATIONS

Donoho (Mol. Cell. Biol., Jul. 1998, vol. 18, No. 7, p. 4070-4078).*
Porteus (Nature Biotechnology, Aug. 2005, vol. 23, No. 8, p. 967-973).*
Ramirez (Unexpected failure rates for modular assembly of engineered zinc fingers. Nature Methods, 2008, 5(5): 374-375).*
Christian (Genetics, available online Jul. 26, 2008, vol. 186, p. 757-761).*
Geurts (Science, Jul. 24, 2009, vol. 325, p. 433).*
Carbery (Genetics, Oct. 2010, vol. 186, p. 451-459).*
Li (Nature, Jul. 14, 2011, vol. 475, No. 7355, p. 217-221, plus Supplemental Material).*
Hauschild (PNAS, Jul. 19, 2011, vol. 108, No. 29, p. 12013-12017).*
Lysosomal storage disease, Wikipedia, 2016.*
Takenaka (Human Gene Therapy, Aug. 10, 1999, vol. 10, p. 1931-1939).*
Takahashi (PNAS, Oct 15, 2002, vol. 99, No. 21, p. 13777-13782).*
Cheng (Gene Therapy, 2003, vol. 10, p. 1275-1281).*
Hodges (Current Gene Therapy, 2006, vol. 6, p. 227-241).*
Sands (Mol. Therapy, May 2006, vol. 13, No. 5, p. 839-849).*
Seregin (Current Pharmaceutical Design, 2011, vol. 17, p. 2558-2574).*
De Garibay (BioDrugs, 2013, vol. 27, p. 237-246).*
Hurler's syndrome, Wikipedia, 2017.*
Hunter's syndrome, Wikipedia, 2017.*
Anguela, et al., "In Vivo Genome Editing of Liver Albumin for Therapuetic Gene Expression, Rescue of Hemophilic Mice via Integration of Factor 9," 54th Annual Meeting and Exposition, 751 Atlanta, USA (Dec. 20, 2012), Abstract, Retrieved from the internet: URL:https://ash.confex.com/ash/2012/webprogram/Paper51404.html.
Beerli, et al., "Engineering Polydactyl Zinc-Finger Transcription Factors," *Nature Biotechnol.* 20:135-141(2002).
Beumer, et al., "Efficient Gene Targeting in *Drosophila* With Zinc-Finger Nucleases," *Genetics* 172:2391-2403 (2006).
Bitinaite, el al., "Fok I Dimerization is Required for DNA Cleavage," *PNAS USA* 95:10570-10575 (1998).
Boch, et al., "Breaking the Code of DNA Binding Specificity of Tal-Type III Effectors," *Science* 326:1509-1512 (2009).
Bonas, et al., "Genetic and Structural Characterization of the Avirulence Gene AVRBS3 From Xanthomonas Campestris PV Vesicatoria," *Mol. Gen. Genet.* 218:127-136 (1989).
Cardone, et al., "Correction of Hunter Syndrome in the MPSII Mouse Model by AAV2/8-Mediated Gene Delivery,"*Hum. Mol. Genet.* 15(7):1225 (2006).
Choo, et al., "Advances in Zinc Finger Engineering," *Curr. Opin. Biotechnol.* 12:632-637 (2000).
Christian, et al., "Targeting DNA Double-Strand Breaks With TAL Effector Nucleases," *Genetics* epub. 10.1534/genetics.110.120717 (2010).
Cohen-Tannoudji, et al., "I-SCEI-Induced Gene Replacement at a Natural Locus in Embryonic Stem Cells," *Mol. Cell. Biol.* 18:1444-1448 (1998).
Cong, et al., "Multiplex Genone Engineering Using CRISPR/CAS Systems," *Science* 339(6121):819-823 (2013).
Dagnino, et al., "Molecular Diagnosis of Analbuminemia: A New Case Caused by a Nonsense Mutation in the Albumin Gene," *International Journal of Molecular Sciences*, 12(12):7314-7322 (Dec. 25, 2011).
DiCarlo et al., "Genome Engineering in *Saccharomyces cerevisiae* using CRISPR-CAS Systems," *Nuc. Acid. Res.* doi:10.1093 (2013).

(56) References Cited

OTHER PUBLICATIONS

Donoho, et al., "Analysis of Gene Targeting and Intrachromosomal Homologous Recombination Stimulated by Genomic Double-Strand Breaks in Mouse Embryonic Stem Cells," *Mol. Cell. Biol.* 18(7):4070-4078 (1998).
Doyon, et al., "Heritable Targeted Gene Disruption in Zebrafish Using Designed Zinc-Finger Nucleases," *Nature Biotech.* 26(6):702-708 (2008).
Ferber, "Bridging the Blood-Brain Barrier: New Methods Improve the Odds of Getting Drugs to the Brain Cells That Need Them," *PLOS Biology* 5(6):1191-1194 (2007).
Gabathuler, et al., "Approaches to Transport Therapeutic Drugs Across the Blood-Brain Barrier to Treat Brain Diseases," *Neurobiology of Disease* 37:48-57 (2010).
Geurts, et al., "Knockout Rats via Embryo Microinjection of Zinc-Finger Nucleases," *Science* 325(5939):433 (2009) doi: 10.1126/science.1172447.
Grabowski, et al., "Phenotype, Diagnosis, and Treatment of Gaucher's Disease," 372(9645):1263-1271 (2008).
Grossman, et al., "Successful Ex Vivo Gene Therapy Directed to Liver in a Patient With Familial Hypercholesterolaemia," *Nature Genetics* 6:335-341 (1994).
Guo, et al., "Directed Evolution of an Enhanced and Highly Efficient FOKI Cleavage Domain for Zinc Finger Nucleases," *Journal of Molecular Biology* 400(1):96-107 (2010).
Guschin, et al., "A Rapid and General Assay for Monitoring Endogenous Gene Modification.," *Methods Mol. Biol.* 649:247-256 (2010).
Haft, et al., "A Guild of 45 CRISPR-Associated (CAS) Protein Families and Multiple CRISPR/CAS Subtypes Exist in Prokaryotic Genomes," *PLoS Comput. Biol.* 1(6):474-483 (2005).
Hartung, et al., "Correction of Metabolic, Craniofacial, and Neurologic Abnormalities in MPS 1 Mice Treated at Birth With Adeno-Associated Virus Vector Transducing the Human Alpha-L-Iduronidase Gene," *Mol. Ther.* 9(6):866 (2004).
Heuer, et al., "Repeat Domain Diversity of AVRBS3-Like Genes in Ralstonia Solanacearum Strains and Association Wiht Host Preferences in the Field" *Appl. and Envir. Micro.* 73(13):4379-4384 (2007).
Isalan, et al., "A Rapid, Generally Applicable Method to Engineer Zinc Fingers Illustrated by Targeting the HIV-1 Promoter," *Nat. Biotechnol.* 19:656-660 (2001).
Jansen, et al., "Identification of Genes That are Associated With DNA Repeats in Prokaryotes," *Mol. Microbiol.* 43:1565-1575 (2002).
Jinek, et al., "A Programmable Dual-RNA-Guided DNA Endonuclease in Adaptive Bacterial Immunity," *Science* 337:816-821 (2012).
Jinek, et al., "RNA-Programmed Genome Editing in Human Cells" *eLife* 2:e00471 (2013).
Johnson-Saliba, "Gene Therapy: Optimising DNA Delivery to the Nucleus," *Curr Drug Targets* 2:371-399 (2001).
Kay, et al., "A Bacterial Effector Acts as a Plant Transcription Factor and Induces a Cell Size Regulator," *Science* 318:648-651 (2007).
Kim, et al., "Chimeric Restriction Endonuclease," *PNAS USA* 91:883-887 (1994a).
Kim, et al., "Hybrid Restriction Enzymes: Zinc Finger Fusions to FOK I Cleavage Domain," *PNAS USA* 93(3):1156-1160 (1996).
Kim, et al., "Instertion and Deletion Mutants of FOKI Restriction Endonuclease," *J. Biol. Chem.* 269:31978-31982 (1994b).
Kormann, "Expression of Therapeutic Proteins After Delivery of Chemically Modified MRNA in Mice," *Nature Biotech.* 29(2):154-157 (2011).
Li, et al., "Alteration of the Cleavage Distance of FOK I Restriction Endonuclease by Insertion Mutagenesis," *PNAS USA* 90:2764-2768 (1993).
Li, et al., "Functional Domains in FOK I Restriction Endonuclease," *PNAS USA* 89:4275-4279 (1992).
Li, et al., "In Vivo Genome Editing Restores Haemostasis in a Mouse Model of Haemophilia," *Nature* 475(7355):217 (2011).
Makatova, et al., "A DNA Repairs System Specific for Thermophilic Archaea and Bacteria Predicted by Genomic Contect Analysis," *Nucleic Acids Res.* 30:482-496 (2002).
Makarova, et al., "A Putative RNA-Interference-Based Immune System in Prokaryotes: Computational Analysis of the Predicted Enzymatic Machinery, Functional Analogies With Eukaryotic RNAI, and Hypothetical Mechanisms of Action," *Biol. Direct* 1:7 (2006).
Meng, et al., "Targeted Gene Inactivation in Zebrafish Using Engineered Zinc-Finger Nucleases," *Nature Biotech.* 26(6):695-701 (2008).
Morton, et al., "Induction and Repair of Zinc-Finger Nuclease-Targeted Double-Strand Breaks in Caenorhabditis Elegans Somaitic Cells," *PNAS USA* 13(44):16370-16375 (2006).
Moscou and Bogdanove, "A Simple Cipher Governs DNA Recognition by Tal Effectors," *Science* 326:1501 (2009).
O'Neil, et al., "Comparison of the Chromosomal Localization of Murine and Human Glucocerebrosidase Genes and of the Deduced Amino Acid Sequences," *PNAS USA* 86:5049-5053 (1989).
Olovnikov, et al., "Bacterial Argonaute Samples the Transcriptome to Identify Foreign DNA," *Mol. Cell.* 51(5):594-605 (2013).
Pabo, et al., "Design and Selection of Novel CYS2HIS2 Zinc Finger Proteins," *Ann. Rev. Biochem.* 20:313-340 (2001).
Perez, et al., "Establishment of HIV-1 Resistance in CD4+ T Cells by Genome Editing Using Zinc-Finger Nucleases," *Nature Biotechnology* 26(7):808-816 (2008).
Ponder, "Immune Response Hinders Therapy for Lysosomal Storage Diseases," *J. Clin. Invest.* 118(8):2686 (2008).
Porteus, et al., "Gene Targeting Using Zinc Finger Nucleases," *Nature Biotechnology* 23(8):967-973 (2005).
Qi, el al., "Repurposing CRISPR as an RNA-Guided Platform for Sequence-Specific Control of Gene Expression," *Cell* 152:1173-1183 (2013).
Ramirez, et al., "Unexpected Failure Rates for Modular Assembly of Engineered Zinc Fingers," *Nature Methods* 5(5):374-375 (2008).
Rebar, "Development of Pro-Angiogenic Engineered Transcription Factors for the Treatment of Cardiovascular Disease," *Expert Opinion Invest. Drugs* 13(7):829-839 (2004).
Roberts, et al., "Rebase Restriction Enzymes and Methyltransferases," *Nucleic Acid Research* 31:418-420 (2003).
Rossi, et al., "Genetic Therapies Against HIV," *Nature Biotech.* 25(12):1444-1454 (2007).
Schornack, et al., "Gene-For-Gene-Mediated Recognition of Nuclear-Targeted AVRBS3-Like Bacterial Effector Proteins," *J Plant Physiol.* 163(3):256-272 (2006).
Segal, "Bacteria Herald a New Era of Gene Editing," *eLife* 2:e00563 (2013).
Segal, et al., "Custom DNA-Binding Proteins Come of Age: Polydactyl Zinc-Finger Proteins," *Curr. Opin. Biotechnol.* 12:632-637 (2001).
Sheng, et al., "Structure-Based Cleavage Mechanism of Thermus Thermophilus Argonaute DNA Guide Strand-Mediated DNA Target Cleavage," *PNAS USA* 111:652 (2013).
Shoji, et al., "Current Status of Delivery Systems to Improve Target Efficacy of Oligonu-Cleotides," *Current Pharmaceutical Design* 10:785-796 (2004).
Sunyer, et al., "Barnes Maze, a Useful Task to Assess Spatial Reference Memory in the Mice," *Protocol Exchange* (2007) doi:10.1038/nprot.2007.390.
Swarts, et al., CRISPR Infernce Directs Strand Specific Spacer Acquisition, *PLos One* 7(4):e35888 (2012).
Tebas, et al., "Gene Editing of CCR5 in Autologous CD4 T Cells of Persons Infected With HIV" *New England Journal of Medicine* 370(10):901 (2014).
Urnov, et al., "Highly Efficient Endogenous Human Gene Correction Using Designed Zinc-Finger Nucleases," *Nature* 435(7042):646-651 (2005).
Vasquez, et al., "Manipulating the Mammalian Genome by Homologous Recombination," *PNAS USA* 98(15):8403-8410 (2001).
Vogel, et al., "A Bacterial Seek-And-Destroy System for Foreign DNA" *Science* 344:972-973 (2014).
Wikipedia, "Gaucher's Disease," (2014).
Wikipedia, "Lysosomal Storage Diseases," (2014).
Yang, et al., "Purification, Cloning, and Characterization of the Cell Nuclease," *Biochemistry* 39:3533-3541 (2000).

(56) References Cited

OTHER PUBLICATIONS

Yuan, et al., Crystal Structure of a Aeolicus Argonaute, a Site-Specific DNA-Guided Endoribonuclease, Provides Insights into RISC-Mediated MRNA Cleavage, *Molecular Cellular* 19:405-419 (2005).
Zetsche, et al., "CPFI is a Single RNA-Guided Endonuclease of a Class 2 CRISPR-CAS System," *Cell* 163:1-13 (2015).
Anguela, et al., "In Vivo Genome Editing of Liver Albumin for Therapeutic Gene Expression: Rescue of Hemophillic Mice Via Integration of Factor 9," Blood, vol. 120, No. 21, Abstract No. 751, 3 pgs. (2012).
Mali, et al., "RNA-Guided Human Genome Engineering Via CAS9," Science, vol. 339, No. 6121, pp. 823-826 (2013).
Boklan, et al., "Factor IX Deficiency in Gaucher Disease. An in Vitro Phenomenon," Arch Intern Med, 136(4):489-492, Abstract only (1976).
Dugaiczyk, et al., "Nucleotide Sequence and the Encoded Amino Acids of Human Serum Albumin MRNA," PNAS, 79:71-75 (1982).
Wang, et al., "Trans-Splicing Into Highly Abundant Albumin Transcripts for Production of Therapeutic Proteins in Vivo," Molecular Therapy, 17(2):343-351 (2009).
Bruni, et al., "Update on Treatment of Lysosomal Storage Diseases," Acta Myologica, XXVI:87-92 (2007).
Carroll, "Genome Engineering With Zinc-Finger Nucleases," Genetics 188:773-782 (2011).
Carroll, "A CRISPR Approach to Gene Targeting," Molecular Therapy 20(9):1658-1660 (2012).
Chial, et al., "Mendelian Genetics: Patterns of Inheritance and Single-Gene Disorders," Nature Education 1(1):63 (2008).
"Your Guide to Understanding Genetic Conditions: Danon Disease" https://ghr.nlm.nih.gov/condition/danon-disease (2019).
Esvelt, et al., "Genome-Scale Engineering for Systems and Synthetic Biology," Molecular Systems Biology 9(641):1-17 (2013).
Follenzi, et al., "Targeting Lentiviral Vector Expression to Hepatocytes Limits Transgene-Specific Immune Response and Establishes Long-Term Expression of Human Antihemophilic Factor IX in Mice," Blood 103(10):3700-3709 (2004).
Kellendonk, et al., "Hepatocyte-Specific Expression of CRE Recombinase," Genesis 26:151-153 (2000).
Matissek, et al., "Choosing Targets for Gene Therapy," Targets in Gene Therapy, Yongping You (ed.) ISBN: 978-953-307-540-2 (2011).
Meštrović, et al. "Single Gene Genetic Disorder," https://www.news-medical.net/health/Single-Gene-Genetic-Disorder.aspx (2018).
Nguyen, et al., "Liver Gene Therapy: Advances and Hurdles," Gene Therapy 11:S76-S84 (2004).

Nishimasu, et al., "Crystal Structure of CAS9 in Complex With Guide Rna and Target DNA," Cell 156:935-949 (2014).
Pelletier, et al., "RNA Based Gene Therapy for Dominantly Inherited Diseases," Current Gene Therapy 6:131-146 (2006).
Porteus, et al., "A Look to Future Directions in Gene Therapy Research for Monogenic Diseases," PLoS Genetics 2(9):1285-1292 (2006).
Richard, "The Genetic and Molecular Bases of Monogenic Disorders Affecting Proteolytic Systems," J Med Genet 42:529-539 (2005).
Ross, et al., "Huntington's Disease: From Molecular Pathogenesis to Clinical Treatment," Lancet Neurol 10:83-98 (2011).
Sadelain, et al., "Safe Harbours for the Integration of New DNA in the Human Genome," Nature Reviews Cancer 12:51-58 (2012).
Sands, et al., "Gene Therapy for Lysosomal Storage Diseases," Molecular Therapy 13:839-849 (2006).
Sharma, et al., "Correction of Hemophilia B Phenotype Following ZFN Mediated Genome Editing in Adult Mice," Molecular Therapy 20(Suppl. 1):S24 (2012).
Silva, et al., "Meganucleases and Other Tools for Targeted Genome Engineering: Perspectives and Challenges for Gene Therapy," Current Gene Therapy 11:11-27 (2011).
Wooddell, et al., "Sustained Liver-Specific Transgene Expression From the Albumin Promoter in Mice Following Hydrodynamic Plasmid DNA Delivery," J Gene Med 10:551-563 (2008).
Barranger, et al., "Gene Transfer Approaches to the Lysosomal Storage Disorders," Neurochemical Research, 24(4):601-615 (1999).
Cox, et al., "Therapeutic Genome Editing: Prospects and Challenges," Nature Medicine, 21(2):121-131 (2015).
Frank, et al., "Investigation of the Cuase of Death in a Gene-Therapy Trial," N. Engl. J. Med, 361(2):161-169 (2009).
Kaiser, et al., "Death Prompts a Review of Gene Therapy Vector," Science, 317:580 (2007).
Schuchman, "Hematopoietic Stem Cell Gene Therapy for Niemann-Pick Disease and Other Lysosomal Storage Diseases," Chemistry and Physics of Lipids, 102:179-188 (1999).
Suzuki, et al., "Are Animal Models Useful for Understanding the Pathophysiology of Lysosomal Storage Disease," Acta Pediatr. Suppl. 443:54-62 (2003).
Thomas, et al., "Progress and Problems With the Use of Viral Vectors for Gene Therapy," Nature Reviews, 4:346-358 (2003).
Verma, et al., "Gene Therapy: Twenty-First Century Medicine," Annu. Rev. Biochem, 74:711-738 (2005).
Walldey, "Cellular Pathology of Lysosomal Storage Disorders," Brain Pathol. 8(1):175-193 (1998).

\* cited by examiner

Figure 1
Hurler, Hunter & Gaucher ZFN + Donor in wildtype mice

Hurler (Iduronidase/IDUA) liver expression

Hurler (Iduronidase/IDUA) plasma activity
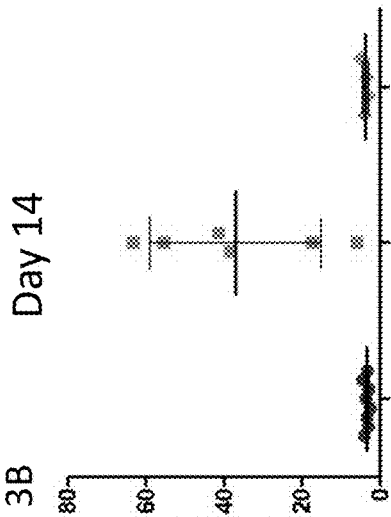
Figure 3A — Day 7
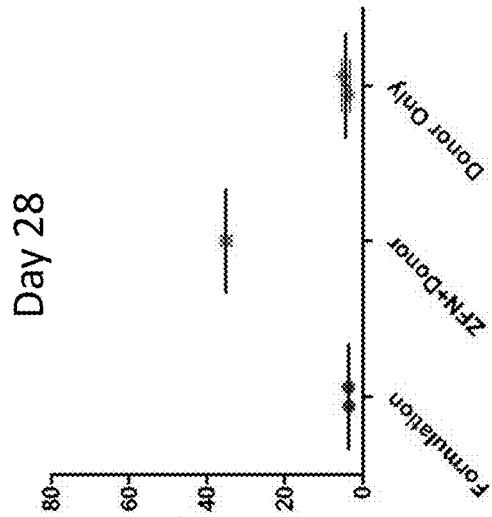
Figure 3B — Day 14
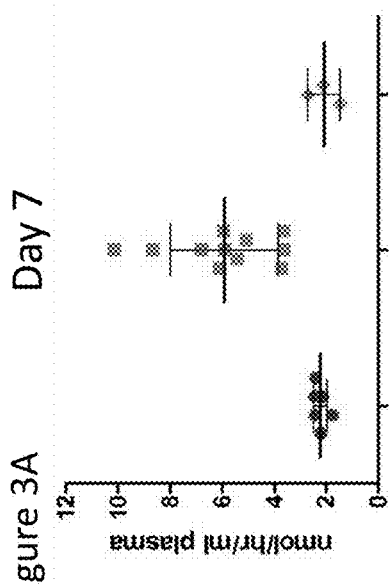
Figure 3C — Day 21
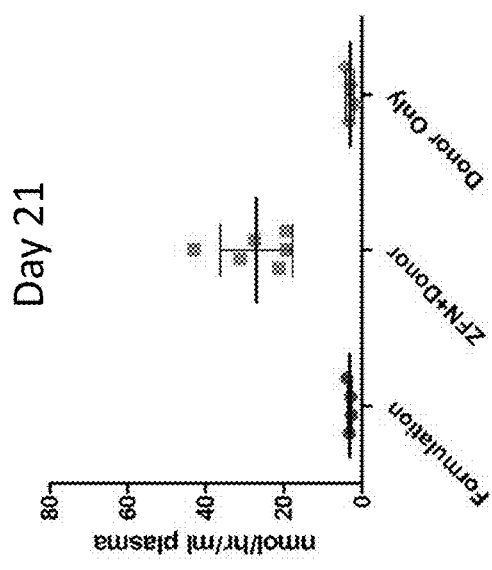
Figure 3D — Day 28

Hunter (Iduronate-2-sulfatase/IDS) liver expression

Hunter (Iduronate-2-sulfatase/IDS) plasma activity
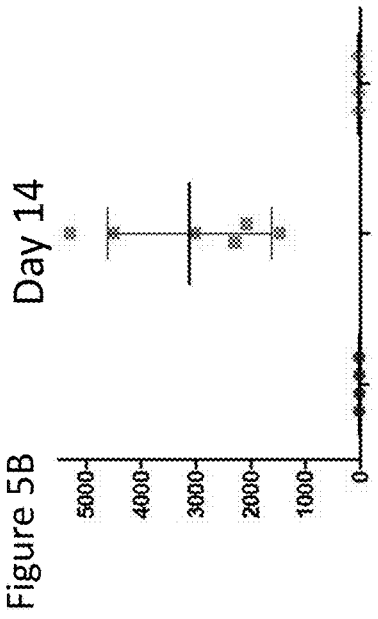
Figure 5A
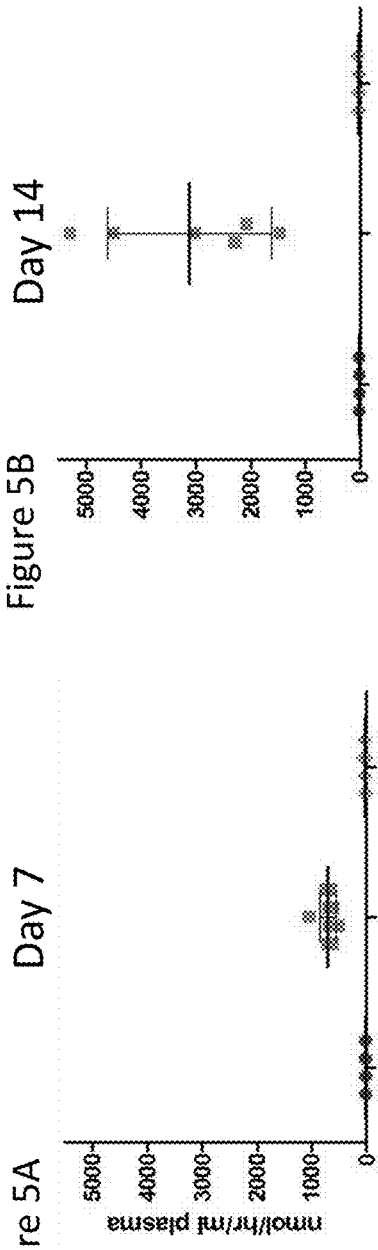
Figure 5B
Figure 5C
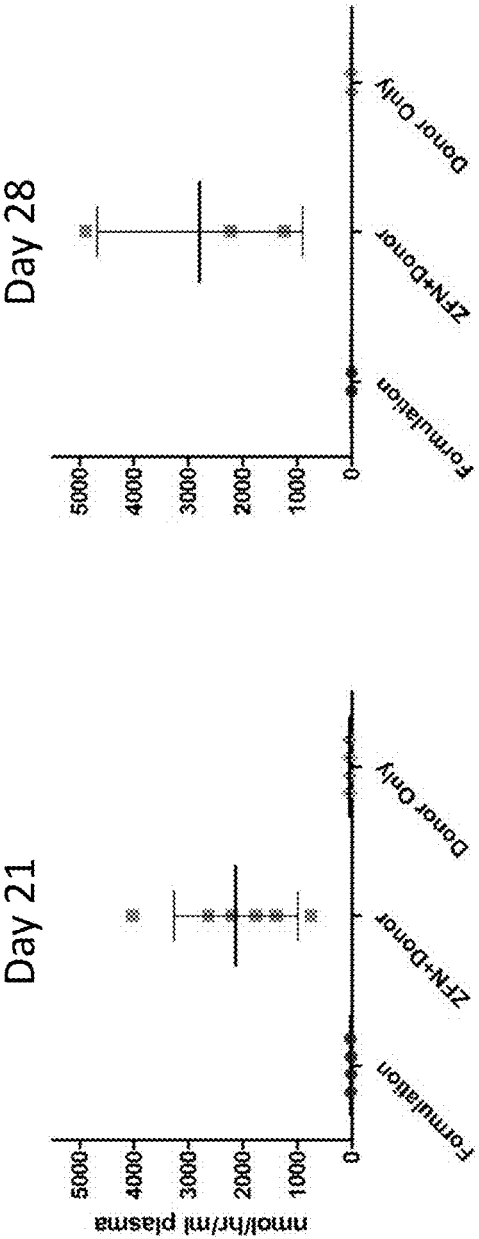
Figure 5D

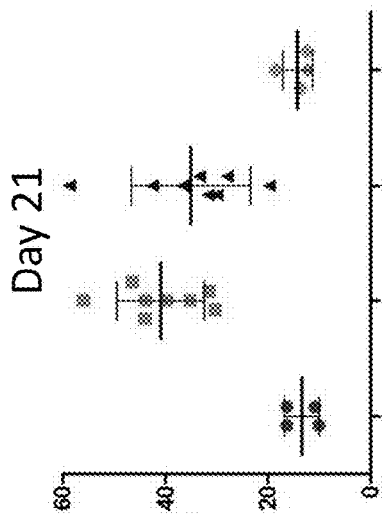
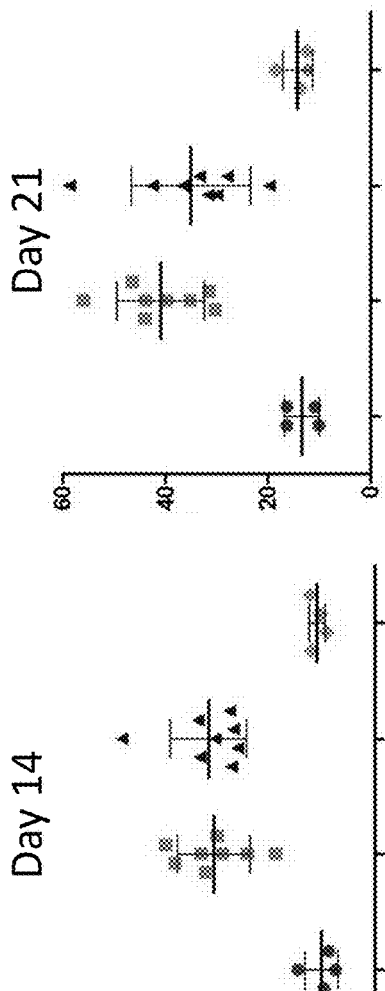
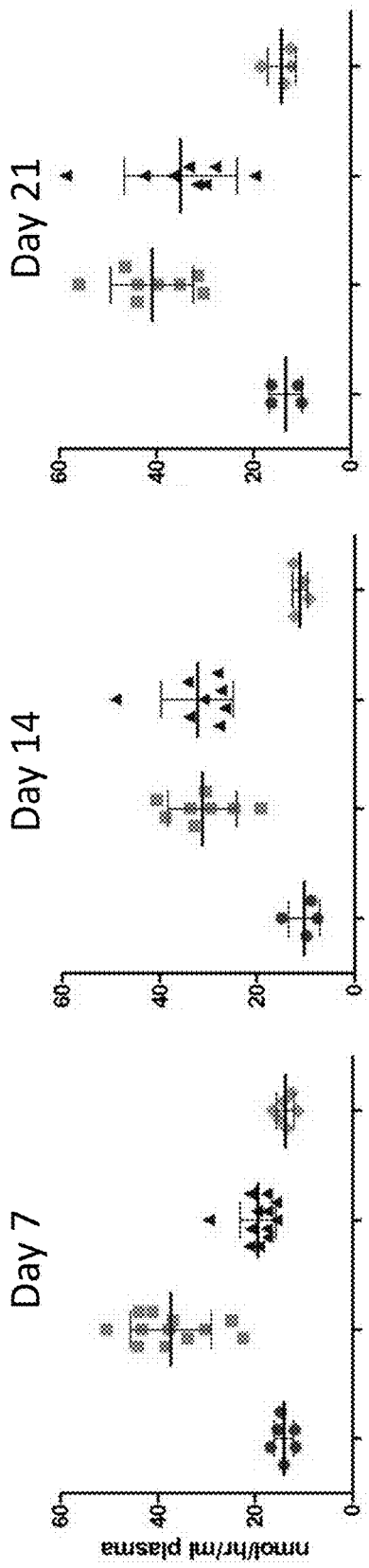
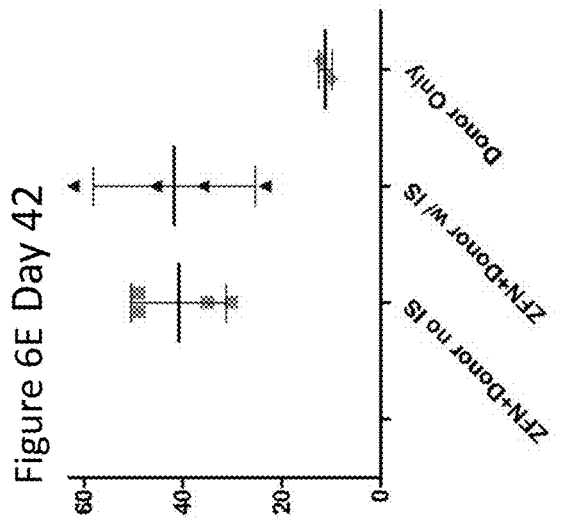
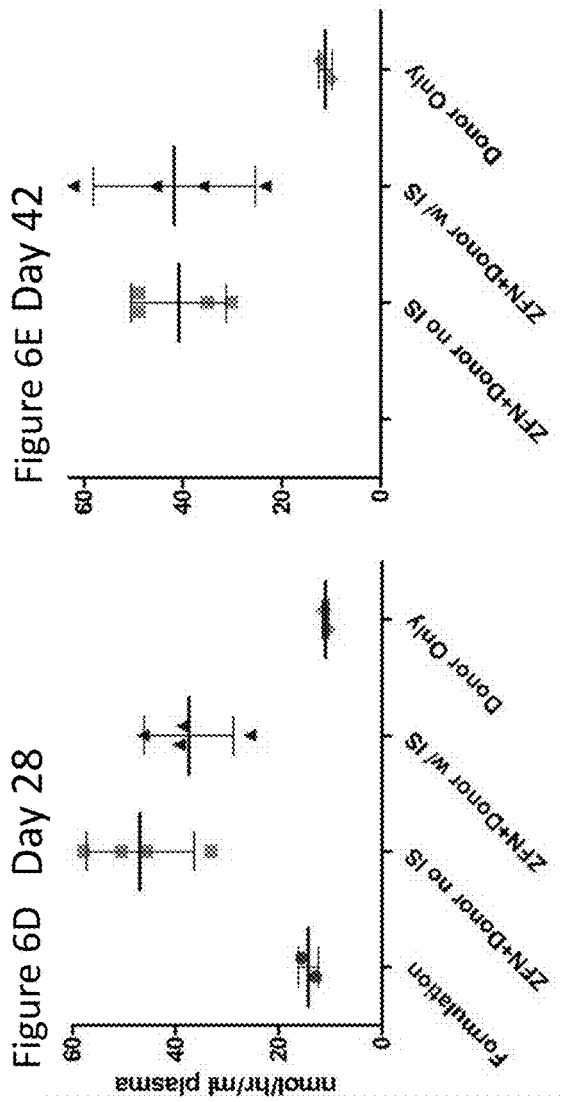

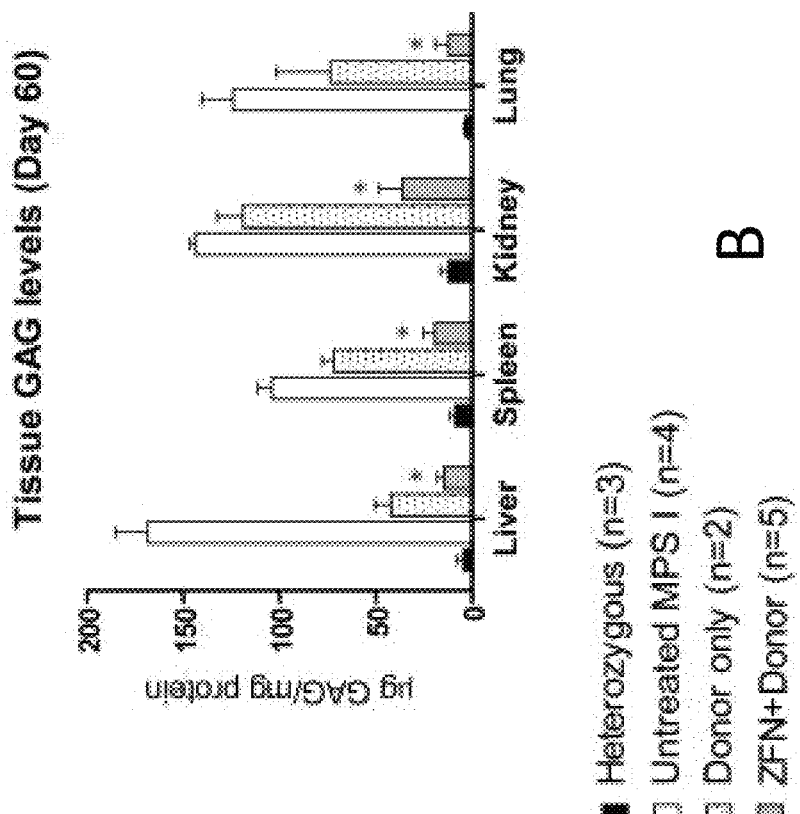
Figure 12A
Figure 12B
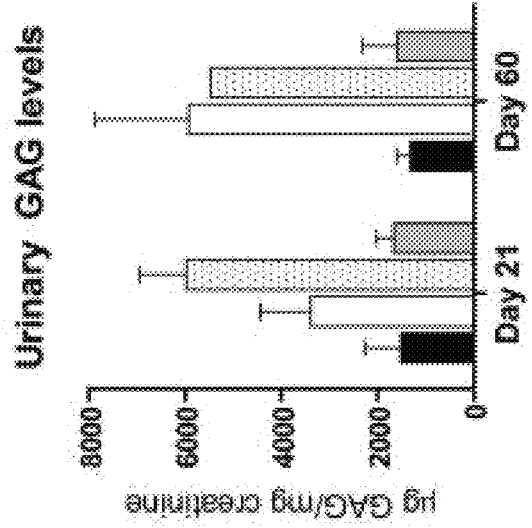

METHOD OF TREATING MUCOPOLYSACCHARIDOSIS TYPE I OR II

CROSS-REFERENCE TO RELATED APPLICATIONS

The present application is a continuation-in-part of U.S. Ser. No. 13/839,336, filed Mar. 15, 2013, which claims the benefit of U.S. Provisional Application No. 61/670,463, filed Jul. 11, 2012; U.S. Provisional Application No. 61/704,072, filed Sep. 21, 2012. This application also claims the benefit of U.S. Provisional Application No. 62/058,400, filed Oct. 1, 2014, and U.S. Provisional Patent Application No. 62/089,070, filed Dec. 8, 2014, the disclosures of which are hereby incorporated by reference in their entireties.

SEQUENCE LISTING

The instant application contains a Sequence Listing which has been submitted electronically in ASCII format and is hereby incorporated by reference in its entirety. Said ASCII copy, created on Oct. 29, 2015, is named 8325009720_SL.txt and is 5,888 bytes in size.

TECHNICAL FIELD

The present disclosure is in the field of the treatment of Lysosomal storage diseases (LSDs) and gene therapy.

BACKGROUND

Gene therapy holds enormous potential for a new era of human therapeutics. These methodologies will allow treatment for conditions that heretofore have not been addressable by standard medical practice. One area that is especially promising is the ability to add a transgene to a cell to cause that cell to express a product that previously not being produced in that cell. Examples of uses of this technology include the insertion of a gene encoding a therapeutic protein, insertion of a coding sequence encoding a protein that is somehow lacking in the cell or in the individual and insertion of a sequence that encodes a structural nucleic acid such as a microRNA.

Transgenes can be delivered to a cell by a variety of ways, such that the transgene becomes integrated into the cell's own genome and is maintained there. In recent years, a strategy for transgene integration has been developed that uses cleavage with site-specific nucleases for targeted insertion into a chosen genomic locus (see, e.g., U.S. Pat. No. 7,888,121). Nucleases, such as zinc finger nucleases (ZFNs), transcription activator-like effector nucleases (TALENs), or nuclease systems such as the CRISPR/Cas system (utilizing an engineered guide RNA) or a TtAgo system, are specific for targeted genes and can be utilized such that the transgene construct is inserted by either homology directed repair (HDR) or by end capture during non-homologous end joining (NHEJ) driven processes. See, e.g., U.S. Pat. Nos. 9,045,763; 9,005,973; 8,956,828; 8,945,868; 8,932,814; 8,586,526; 6,534,261; 6,599,692; 6,503,717; 6,689,558; 7,067,317; 7,262,054; 7,888,121; 7,972,854; 7,914,796; 7,951,925; 8,110,379; 8,409,861; U.S. Patent Publications 20030232410; 20050208489; 20050026157; 20050064474; 20060063231; 20080159996; 201000218264; 20120017290; 20110265198; 20130137104; 20130122591; 20130177983; 20130177960; 20150056705 and 20150335708, the disclosures of which are incorporated by reference in their entireties.

Targeted loci include "safe harbor" loci such as the AAVS1, HPRT, albumin and CCR5 genes. See, e.g., U.S. Pat. Nos. 7,888,121; 7,972,854; 7,914,796; 7,951,925; 8,110,379; 8,409,861; 8,586,526; U.S. Patent Publications 20030232410; 20050208489; 20050026157; 20060063231; 20080159996; 201000218264; 20120017290; 20110265198; 20130137104; 20130122591; 20130177983 and 20130177960. Nuclease-mediated integration offers the prospect of improved transgene expression, increased safety and expressional durability, as compared to classic integration approaches that rely on random integration of the transgene, since it allows exact transgene positioning for a minimal risk of gene silencing or activation of nearby oncogenes.

While delivery of the transgene to the target cell is one hurdle that must be overcome to fully enact this technology, another issue that must be conquered is insuring that after the transgene is inserted into the cell and is expressed, the gene product so encoded must reach the necessary location with the organism, and be made in sufficient local concentrations to be efficacious. For diseases characterized by the lack of a protein or by the presence of an aberrant non-functional one, delivery of a transgene encoded wild type protein can be extremely helpful.

Lysosomal storage diseases (LSDs) are a group of rare metabolic monogenic diseases characterized by the lack of functional individual lysosomal proteins normally involved in the breakdown of waste lipids, glycoproteins and mucopolysaccharides. These diseases are characterized by a buildup of these compounds in the cell since it is unable to process them for recycling due to the mis-functioning of a specific enzyme. The most common examples are Gaucher's (glucocerebrosidase deficiency—gene name: GBA), Fabry's (α galactosidase deficiency—GLA), Hunter's (iduronate-2-sulfatase deficiency—IDS), Hurler's (alpha-L iduronidase deficiency—IDUA), Pompe's (alpha-glucosidase (GAA)) and Niemann-Pick's (sphingomyelin phosphodiesterase 1 deficiency—SMPD1) diseases. When grouped all together, LSDs have an incidence in the population of about 1 in 7000 births. These diseases have devastating effects on those afflicted with them. They are usually first diagnosed in babies who may have characteristic facial and body growth patterns and may have moderate to severe mental retardation. Treatment options include enzyme replacement therapy (ERT) where the missing enzyme is given to the patient, usually through intravenous injection in large doses. Such treatment is only to treat the symptoms and is not curative, thus the patient must be given repeated dosing of these proteins for the rest of their lives, and potentially may develop neutralizing antibodies to the injected protein. Often these proteins have a short serum half life, and so the patient must also endure frequent infusions of the protein. For example, Gaucher's disease patients receiving the Cerezyme® product (imiglucerase) must have infusions three times per week. Production and purification of the enzymes is also problematic, and so the treatments are very costly (>$100,000 per year per patient).

Nonetheless, there remains a need for additional methods and compositions that can be used to treat a monogenic disease (e.g. Lysosomal storage diseases) through genome editing, and methods to deliver an expressed transgene encoded gene product at an increased therapeutically relevant level.

SUMMARY

Disclosed herein are methods and compositions for treating a monogenic disease. The invention describes methods for insertion of a transgene sequence into an endogenous gene (e.g., albumin or HPRT) in a liver or stem cell, wherein the transgene encodes a protein that treats the disease and the protein is expressed at increased levels (compared to untreated subjects) in the liver and active therapeutic protein is detected in blood (plasma) and in secondary tissues such as spleen. Thus, the therapeutic protein is excreted from the target cell such that it is able to affect or be taken up by other cells that do not harbor the transgene.

In one aspect, described herein is a method of providing a therapeutic protein useful in treating a monogenic disease (e.g., LSD), the method comprising introducing the transgene into a cell (e.g., liver cell) into an endogenous gene (e.g., a safe harbor gene such as albumin or HPRT) in a subject, such that the therapeutic protein is expressed in the liver and detectable in secondary tissues in the subject. The secondary tissues include blood (plasma), spleen, muscle, etc. Furthermore, the protein may be expressed at increased levels in the liver and secondary tissues as compared to untreated subjects. In certain embodiments, the protein is an enzyme and the methods result a 2-4 fold, or 2-10 fold or 10-100 fold (or even more) increase in the enzymatic activity of the protein in liver and/or secondary tissues. The transgene may be integrated into the endogenous locus using a zinc finger nuclease, a TALEN, a CRISPR/Cas nuclease system and/or a Ttago nuclease system. The nuclease may be introduced into the subject in polynucleotide form, for example, as mRNA. In some aspects, the mRNA may be chemically modified (See e.g. Kormann et al, (2011) *Nature Biotechnology* 29(2):154-157). In some aspects, mRNA is introduced via a nanoparticle, for example via a liposome or other type of nanoparticle. In some embodiments, the nuclease is introduced in a virus. In some aspects, the virus is an AAV. In certain embodiments, the transgenes is integrated into a safe harbor locus, for example, an albumin or HPRT locus. Targeted integration of a transgene into the HPRT locus can also result in inactivation of the endogenous HPRT, which in turn allows for selection of cells comprising the transgene.

In one aspect, the invention describes a method of treating a lysosomal storage disease by inserting in a corrective transgene into a suitable target cell (e.g., liver cell) such that the product encoded by that corrective transgene is expressed. In one embodiment, the corrective transgene is inserted into a cell line for the in vitro production of the replacement protein. The cells comprising the transgene or the protein produced by the cells can be used to treat a patient in need thereof, for example following purification of the produced protein. In another embodiment, the corrective transgene is inserted into a target tissue in the body such that the replacement protein is produced in vivo. In any of the methods described herein, the LSD may be Hurler disease and the transgene may encode iduronidase; or Hunter disease and the transgene may be iduronate-2-sulfatase; and/or Gaucher disease and the transgene may be glucocerebrosidase and/or Fabry disease and the transgene may be α-galactosidase; and/or Pompe disease and the transgene may be α-glucosidase. In some aspects, the expressed protein is excreted from the cell to act on or be taken up by other cells or target tissues (e.g. plasma, spleen, etc.) that lack the transgene. In some instances, the excreting cell is in the liver. In other instances, the target tissue is the brain. In other instances, the target is blood (e.g., vasculature). In other instances, the target is skeletal muscle. In one embodiment, the corrective gene comprises the wild type sequence of the functioning gene, while in other embodiments, the sequence of the corrective transgene is altered in some manner to give enhanced biological activity. In some aspects, the corrective transgene comprises optimized codons to increase biological activity, while in other aspects, the sequence is altered to give the resultant protein more desired function (e.g., improvement in stability, alteration of charge to alter substrate binding etc.). In some embodiments, the transgene is altered for reduced immunogenicity of the expressed protein. In other cases, the transgene is altered such that the encoded protein becomes a substrate for transporter-mediated delivery in specific tissues such as the brain (see Gabathuler et al. (2010) *Neurobiology of Disease* 37: 48-57).

In some embodiments the transgene is expressed such that a therapeutic protein product is retained within the cell (e.g., precursor or mature cell). In other embodiments, the transgene is fused to the extracellular domain of a membrane protein such that upon expression, a transgene fusion will result in the surface localization of the therapeutic protein. In some aspects, the extracellular domain is chosen from those proteins listed in Table 1. In some aspects, the edited cells also comprise a transmembrane protein to traffic the cells to a particular tissue type. In one aspect, the transmembrane protein is an antibody, while in others, the transmembrane protein is a receptor. In certain embodiments, the cell is a precursor (e.g., CD34+ or hematopoietic stem cell) or mature RBC. In some aspects, the therapeutic protein product encoded on the transgene is exported out of the cell through use of a secretory peptide linked to the therapeutic protein to affect or be taken up by cells lacking the transgene. In some aspects, the secretory peptide is heterologous to the therapeutic protein and is removed during the secretion process. In further aspects, the secretory peptide is an endogenous albumin secretory peptide. In certain embodiments, the cell is a liver cell which releases the therapeutic protein into the blood stream to act on distal tissues (e.g., brain).

In one embodiment, the transgene is expressed from the endogenous promoter following insertion into the endogenous locus (e.g., the endogenous albumin promoter following insertion into the endogenous albumin gene or the endogenous HPRT promoter following insertion into the endogenous HPRT gene). The biologic encoded by the transgene then may be released into the blood stream if the transgene is inserted into a hepatocyte in vivo. In some aspects, the transgene is delivered to the liver in vivo in a viral vector through intravenous injection.

In another embodiment, the transgene encodes a non-coding RNA, e.g. an shRNA. Expression of the transgene prior to cell maturation will result in a cell containing the non-coding RNA of interest.

In one aspect, described herein is a genetically modified cell or cell line, for example as compared to the wild-type genomic sequence of the same type of cell or cell line (e.g., stem cell). The cell or cell line may be heterozygous or homozygous for the modification. The modifications may comprise insertions, deletions and/or combinations thereof and in certain embodiments are in an HPRT gene. In certain embodiments, the cells are modified with an engineered nuclease and a donor nucleic acid such that a wild type gene (e.g., protein lacking in a lysosomal storage disease) is inserted and expressed and/or an endogenous aberrant gene is corrected. In certain embodiments, the modification (e.g., insertion) is at or near the nuclease(s) binding and/or cleavage site(s), including but not limited to, modifications to sequences within 1-300 (or any number of base pairs therebetween) base pairs upstream or downstream of the site(s) of cleavage and/or binding site; modifications within 1-100 base pairs (or any number of base pairs therebetween) of either side of the binding and/or cleavage site(s); modifications within 1 to 50 base pairs (or any number of base pairs therebetween) on either side of the binding and/or cleavage site(s); and/or modifications to one or more base pairs of the nuclease binding site and/or cleavage site. In certain embodiments, the modification is at or near (e.g., 1-300 base pairs or any number of base pairs therebetween) SEQ ID NO:24 or 25. In other embodiments, the modification is 1-100 (or any number of base pairs therebetween) base pairs of SEQ ID NO:24 or 25. In certain embodiments, the modification is within SEQ ID NO:24 and/or SEQ ID NO:25, for example a modification of 1 or more base pairs in either SEQ ID NO:24 or 25. Partially or fully differentiated cells descended from the genetically modified stem cells as described herein are also provided (e.g., RBCs or RBC precursor cells). Compositions such as pharmaceutical compositions comprising the genetically modified cells as described herein are also provided. Thus, the methods of the invention may be used in vivo in transgenic animal systems. In some aspects, the transgenic animal may used in model development where the transgene encodes a human gene. In some instances, the transgenic animal may be knocked out at the corresponding endogenous locus, allowing the development of an in vivo system where the human protein may be studied in isolation. Such transgenic models may be used for screening purposes to identify small molecules, or large biomolecules or other entities which may interact with or modify the human protein of interest. In some aspects, the transgene is integrated into the selected locus (e.g., albumin, HPRT, or other safe-harbor locus) into a stem cell (e.g., an embryonic stem cell, an induced pluripotent stem cell, a hepatic stem cell, a neural stem cell etc.) or animal embryo obtained by any of the methods described herein, and then the embryo is implanted such that a live animal is born. The animal is then raised to sexual maturity and allowed to produce offspring wherein at least some of the offspring comprise the integrated transgene.

A kit, comprising the ZFN, TALEN, and/or CRISPR/Cas or TtAgo system of the invention, is also provided. The kit may comprise nucleic acids encoding the ZFN, TALEN, and/or CRISPR/Cas or TtAgo system, (e.g. RNA molecules or the ZFN, TALEN, and/or CRISPR/Cas or TtAgo system encoding genes contained in a suitable expression vector), donor molecules, expression vectors encoding the single guide RNA suitable host cell lines, instructions for performing the methods of the invention, and the like.

These and other aspects will be readily apparent to the skilled artisan in light of disclosure as a whole.

BRIEF DESCRIPTION OF THE DRAWINGS

FIG. 1 is a table showing the experimental design and viral constructs used for integration of the indicated Hurler, Hunter and Gaucher donors using into wild-type mice using albumin-targeted nucleases (ZFNs).

FIGS. 3A to 3D are graphs depicting iduronidase activity in plasma in the indicated animals as measured by enzymatic activity assay. Enzyme activity is shown for control animals ("formulation"), animals receiving ZFN and the iduronidase-encoding donor ("ZFN+donor") and iduronidase-encoding only donor only ("donor only") at day 7 (FIG. 3A), day 14 (FIG. 3B), day 21 (FIG. 3C) and day 28 (FIG. 3D).

FIGS. 5A to 5D are graphs depicting iduronate-2-sulfatase activity in plasma in the indicated animals as measured by enzymatic activity assay. Enzyme activity is shown for control animals ("formulation"), animals receiving ZFN and the iduronate-2-sulfatase-encoding donor ("ZFN+donor") and iduronate-2-sulfatase-encoding only donor only ("donor only") at day 7 (FIG. 5A), day 14 (FIG. 5B), day 21 (FIG. 5C) and day 28 (FIG. 5D).

FIGS. 6A to 6E are graphs depicting glucocerebrosidase/GBA1 activity in plasma in the indicated animals as measured by enzymatic activity assay. Enzyme activity is shown for control animals ("formulation"), animals receiving ZFN and the glucocerebrosidase-encoding donor with or without immune suppression ("IS") ("ZFN+donor no IS" and "ZFN+donor w/IS"), and animals receiving and glucocerebrosidase-encoding only donor only ("donor only") at day 7 (FIG. 6A), day 14 (FIG. 6B), day 21 (FIG. 6C), day 28 (FIG. 6D) and day 42 (FIG. 6E).

FIG. 8A shows the viability of the cells following transfection, with and without 6-TG selection while FIG. 8B shows the percent of NHEJ observed in these cell populations. FIG. 8C shows the percent of alleles in the cell population comprising an IDS transgene with and without 6-TG selection while FIG. 8D depicts the IDS enzymatic activity measured in the cell supernatant.

FIG. 9A shows the viability of the cells following transfection, with and without 6-TG selection while FIG. 9B shows the percent of NHEJ observed in these cell populations. FIG. 9C shows the percent of alleles in the cell population comprising a IDS transgene with and without 6-TG selection while FIG. 9D depicts the IDS enzymatic activity measured in the cell supernatant.

FIG. 10A shows IDUA present in the liver, FIG. 10B shows IDUA in the plasma and FIG. 10C shows IDUA detected in the spleen, kidney and lung.

FIG. 11A shows the IDS present in the liver, FIG. 11B shows the IDS in the plasma and FIG. 11C shows the IDS present in the spleen, kidney and lung.

FIGS. 12A and 12B are graphs of GAG levels found in the urine and in the tissues of MPSI mice treated as in FIG. 10. Treatment of mice with ZFN and IDUA donor was associated with lower GAG levels that untreated mice.

DETAILED DESCRIPTION

Figure 2:
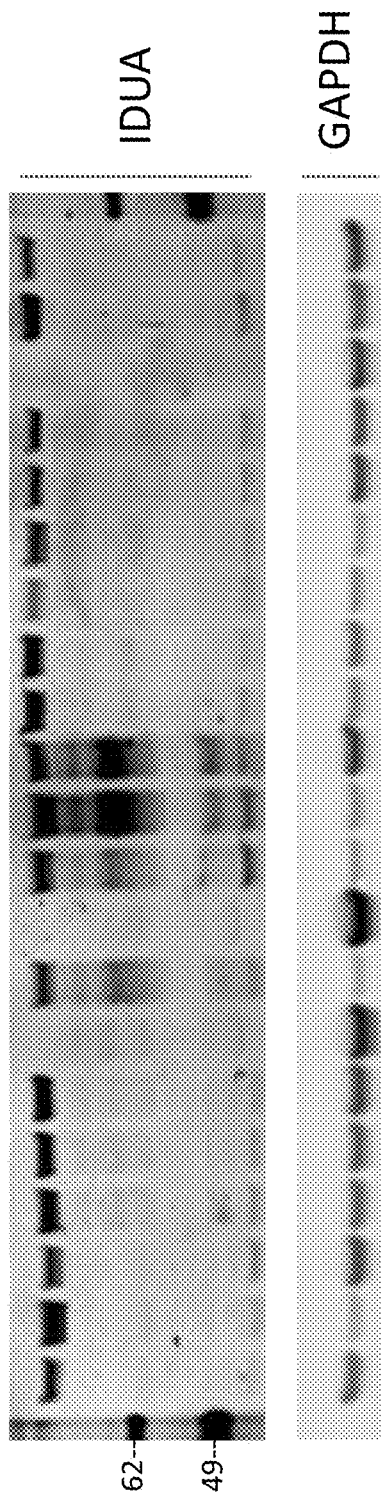
FIG. 2 depicts Western blot results of iduronidase expression in liver cells of the indicated animals (controls ("Ctrl"), donor+ZFNs, donor only and ZFN only). The material in each lane is derived from a single mouse liver biopsy on the day indicated (D7, D21, D28). The numbers for the groups (1, 2, 3, and 9) indicate the groups as shown in FIG. 1. A loading control "GAPDH" is shown at the bottom of the figure.

Disclosed herein are methods and compositions for treating or preventing a lysosomal storage disease (LSD). The invention provides methods and compositions for insertion of a gene encoding a protein that is lacking or insufficiently expressed in the subject with the LSD such that the gene introduced into an endogenous (e.g., albumin or HPRT) gene such that the gene is expressed and the therapeutic (replacement) protein is expressed in the liver of the subject and in secondary tissues such as plasma, spleen, etc. at significantly increased levels (4 to 100 fold or more) as compared to untreated subjects. The transgene encodes a protein (e.g., enzyme) that is deficient of lacking in an LSD.

General

Practice of the methods, as well as preparation and use of the compositions disclosed herein employ, unless otherwise indicated, conventional techniques in molecular biology, biochemistry, chromatin structure and analysis, computational chemistry, cell culture, recombinant DNA and related fields as are within the skill of the art. These techniques are fully explained in the literature. See, for example, Sambrook et al. MOLECULAR CLONING: A LABORATORY MANUAL, Second edition, Cold Spring Harbor Laboratory Press, 1989 and Third edition, 2001; Ausubel et al., CURRENT PROTOCOLS IN MOLECULAR BIOLOGY, John Wiley & Sons, New York, 1987 and periodic updates; the series METHODS IN ENZYMOLOGY, Academic Press, San Diego; Wolffe, CHROMATIN STRUCTURE AND FUNCTION, Third edition, Academic Press, San Diego, 1998; METHODS IN ENZYMOLOGY, Vol. 304, "Chromatin" (P. M. Wassarman and A. P. Wolffe, eds.), Academic Press, San Diego, 1999; and METHODS IN MOLECULAR BIOLOGY, Vol. 119, "Chromatin Protocols" (P. B. Becker, ed.) Humana Press, Totowa, 1999.

Definitions

The terms "nucleic acid," "polynucleotide," and "oligonucleotide" are used interchangeably and refer to a deoxyribonucleotide or ribonucleotide polymer, in linear or circular conformation, and in either single- or double-stranded form. For the purposes of the present disclosure, these terms are not to be construed as limiting with respect to the length of a polymer. The terms can encompass known analogues of natural nucleotides, as well as nucleotides that are modified in the base, sugar and/or phosphate moieties (e.g., phosphorothioate backbones). In general, an analogue of a particular nucleotide has the same base-pairing specificity; i.e., an analogue of A will base-pair with T.

The terms "polypeptide," "peptide" and "protein" are used interchangeably to refer to a polymer of amino acid residues. The term also applies to amino acid polymers in which one or more amino acids are chemical analogues or modified derivatives of a corresponding naturally-occurring amino acids.

"Binding" refers to a sequence-specific, non-covalent interaction between macromolecules (e.g., between a protein and a nucleic acid). Not all components of a binding interaction need be sequence-specific (e.g., contacts with phosphate residues in a DNA backbone), as long as the interaction as a whole is sequence-specific. Such interactions are generally characterized by a dissociation constant ($K_d$) of $10^{-6}$ $M^{-1}$ or lower. "Affinity" refers to the strength of binding: increased binding affinity being correlated with a lower $K_d$.

A "binding protein" is a protein that is able to bind to another molecule. A binding protein can bind to, for example, a DNA molecule (a DNA-binding protein), an RNA molecule (an RNA-binding protein) and/or a protein molecule (a protein-binding protein). In the case of a protein-binding protein, it can bind to itself (to form homodimers, homotrimers, etc.) and/or it can bind to one or more molecules of a different protein or proteins. A binding protein can have more than one type of binding activity. For example, zinc finger proteins have DNA-binding, RNA-binding and protein-binding activity.

A "zinc finger DNA binding protein" (or binding domain) is a protein, or a domain within a larger protein, that binds DNA in a sequence-specific manner through one or more zinc fingers, which are regions of amino acid sequence within the binding domain whose structure is stabilized through coordination of a zinc ion. The term zinc finger DNA binding protein is often abbreviated as zinc finger protein or ZFP.

A "TALE DNA binding domain" or "TALE" is a polypeptide comprising one or more TALE repeat domains/units. The repeat domains are involved in binding of the TALE to its cognate target DNA sequence. A single "repeat unit" (also referred to as a "repeat") is typically 33-35 amino acids in length and exhibits at least some sequence homology with other TALE repeat sequences within a naturally occurring TALE protein. See; e.g., U.S. Pat. No. 8,586,526.

Zinc finger and TALE binding domains can be "engineered" to bind to a predetermined nucleotide sequence, for example via engineering (altering one or more amino acids) of the recognition helix region of a naturally occurring zinc finger or TALE protein. Therefore, engineered DNA binding proteins (zinc fingers or TALEs) are proteins that are non-naturally occurring. Non-limiting examples of methods for engineering DNA-binding proteins are design and selection. A designed DNA binding protein is a protein not occurring in nature whose design/composition results principally from rational criteria. Rational criteria for design include application of substitution rules and computerized algorithms for processing information in a database storing information of existing ZFP and/or TALE designs and binding data. See, for example, U.S. Pat. Nos. 8,568,526; 6,140,081; 6,453,242; and 6,534,261; see also WO 98/53058; WO 98/53059; WO 98/53060; WO 02/016536 and WO 03/016496.

A "selected" zinc finger protein or TALE is a protein not found in nature whose production results primarily from an empirical process such as phage display, interaction trap or hybrid selection. See e.g., U.S. Pat. Nos. 8,586,526; 5,789, 538; 5,925,523; 6,007,988; 6,013,453; 6,200,759; WO 95/19431; WO 96/06166; WO 98/53057; WO 98/54311; WO 00/27878; WO 01/60970 WO 01/88197, WO 02/099084.

"TtAgo" is a prokaryotic Argonaute protein thought to be involved in gene silencing. TtAgo is derived from the bacteria *Thermus thermophilus*. See, e.g., Swarts et al, ibid, G. Sheng et al., (2013) *Proc. Natl. Acad. Sci. U.S.A.* 111, 652). A "TtAgo system" is all the components required including, for example, guide DNAs for cleavage by a TtAgo enzyme.

"Recombination" refers to a process of exchange of genetic information between two polynucleotides, including but not limited to, donor capture by non-homologous end joining (NHEJ) and homologous recombination. For the purposes of this disclosure, "homologous recombination (HR)" refers to the specialized form of such exchange that takes place, for example, during repair of double-strand breaks in cells via homology-directed repair mechanisms. This process requires nucleotide sequence homology, uses a "donor" molecule to template repair of a "target" molecule (i.e., the one that experienced the double-strand break), and is variously known as "non-crossover gene conversion" or "short tract gene conversion," because it leads to the transfer of genetic information from the donor to the target. Without wishing to be bound by any particular theory, such transfer can involve mismatch correction of heteroduplex DNA that forms between the broken target and the donor, and/or "synthesis-dependent strand annealing," in which the donor is used to resynthesize genetic information that will become part of the target, and/or related processes. Such specialized HR often results in an alteration of the sequence of the target molecule such that part or all of the sequence of the donor polynucleotide is incorporated into the target polynucleotide.

In the methods of the disclosure, one or more targeted nucleases as described herein create a double-stranded break in the target sequence (e.g., cellular chromatin) at a predetermined site, and a "donor" polynucleotide, having homology to the nucleotide sequence in the region of the break, can be introduced into the cell. The presence of the double-stranded break has been shown to facilitate integration of the donor sequence. The donor sequence may be physically integrated or, alternatively, the donor polynucleotide is used as a template for repair of the break via homologous recombination, resulting in the introduction of all or part of the nucleotide sequence as in the donor into the cellular chromatin. Thus, a first sequence in cellular chromatin can be altered and, in certain embodiments, can be converted into a sequence present in a donor polynucleotide. Thus, the use of the terms "replace" or "replacement" can be understood to represent replacement of one nucleotide sequence by another, (i.e., replacement of a sequence in the informational sense), and does not necessarily require physical or chemical replacement of one polynucleotide by another.

In any of the methods described herein, additional pairs of zinc-finger proteins or TALEN can be used for additional double-stranded cleavage of additional target sites within the cell.

Any of the methods described herein can be used for insertion of a donor of any size and/or partial or complete inactivation of one or more target sequences in a cell by targeted integration of donor sequence that disrupts expression of the gene(s) of interest. Cell lines with partially or completely inactivated genes are also provided.

Furthermore, the methods of targeted integration as described herein can also be used to integrate one or more exogenous sequences. The exogenous nucleic acid sequence can comprise, for example, one or more genes or cDNA molecules, or any type of coding or noncoding sequence, as well as one or more control elements (e.g., promoters). In addition, the exogenous nucleic acid sequence may produce one or more RNA molecules (e.g., small hairpin RNAs (shRNAs), inhibitory RNAs (RNAis), microRNAs (miRNAs), etc.).

In certain embodiments of methods for targeted recombination and/or replacement and/or alteration of a sequence in a region of interest in cellular chromatin, a chromosomal sequence is altered by homologous recombination with an exogenous "donor" nucleotide sequence. Such homologous recombination is stimulated by the presence of a double-stranded break in cellular chromatin, if sequences homologous to the region of the break are present.

In any of the methods described herein, the exogenous nucleotide sequence (the "donor sequence" or "transgene") can contain sequences that are homologous, but not identical, to genomic sequences in the region of interest, thereby stimulating homologous recombination to insert a non-identical sequence in the region of interest. Thus, in certain embodiments, portions of the donor sequence that are homologous to sequences in the region of interest exhibit between about 80 to 99% (or any integer therebetween) sequence identity to the genomic sequence that is replaced. In other embodiments, the homology between the donor and genomic sequence is higher than 99%, for example if only 1 nucleotide differs as between donor and genomic sequences of over 100 contiguous base pairs. In certain cases, a non-homologous portion of the donor sequence can contain sequences not present in the region of interest, such that new sequences are introduced into the region of interest. In these instances, the non-homologous sequence is generally flanked by sequences of 50-1,000 base pairs (or any integral value therebetween) or any number of base pairs greater than 1,000, that are homologous or identical to sequences in the region of interest. In other embodiments, the donor sequence is non-homologous to the first sequence, and is inserted into the genome by non-homologous recombination mechanisms.

"Cleavage" refers to the breakage of the covalent backbone of a DNA molecule. Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events. DNA cleavage can result in the production of either blunt ends or staggered ends. In certain embodiments, fusion polypeptides are used for targeted double-stranded DNA cleavage.

A "cleavage half-domain" is a polypeptide sequence which, in conjunction with a second polypeptide (either identical or different) forms a complex having cleavage activity (preferably double-strand cleavage activity). The terms "first and second cleavage half-domains;" "+ and − cleavage half-domains" and "right and left cleavage half-domains" are used interchangeably to refer to pairs of cleavage half-domains that dimerize.

An "engineered cleavage half-domain" is a cleavage half-domain that has been modified so as to form obligate heterodimers with another cleavage half-domain (e.g., another engineered cleavage half-domain). U.S. Pat. Nos. 7,888,121; 7,914,796; 8,034,598 and 8,823,618, incorporated herein by reference in their entireties.

The term "sequence" refers to a nucleotide sequence of any length, which can be DNA or RNA; can be linear, circular or branched and can be either single-stranded or double stranded. The term "donor sequence" refers to a nucleotide sequence that is inserted into a genome. A donor sequence can be of any length, for example between 2 and 100,000,000 nucleotides in length (or any integer value therebetween or thereabove), preferably between about 100 and 100,000 nucleotides in length (or any integer therebetween), more preferably between about 2000 and 20,000 nucleotides in length (or any value therebetween) and even more preferable, between about 5 and 15 kb (or any value therebetween).

A "homologous, non-identical sequence" refers to a first sequence which shares a degree of sequence identity with a second sequence, but whose sequence is not identical to that of the second sequence. For example, a polynucleotide comprising the wild-type sequence of a mutant gene is homologous and non-identical to the sequence of the mutant gene. In certain embodiments, the degree of homology between the two sequences is sufficient to allow homologous recombination therebetween, utilizing normal cellular mechanisms. Two homologous non-identical sequences can be any length and their degree of non-homology can be as small as a single nucleotide (e.g., for correction of a genomic point mutation by targeted homologous recombination) or as large as 10 or more kilobases (e.g., for insertion of a gene at a predetermined ectopic site in a chromosome). Two polynucleotides comprising the homologous non-identical sequences need not be the same length. For example, an exogenous polynucleotide (i.e., donor polynucleotide) of between 20 and 10,000 nucleotides or nucleotide pairs can be used.

Techniques for determining nucleic acid and amino acid sequence identity are known in the art. Typically, such techniques include determining the nucleotide sequence of the mRNA for a gene and/or determining the amino acid sequence encoded thereby, and comparing these sequences to a second nucleotide or amino acid sequence. Genomic sequences can also be determined and compared in this fashion. In general, identity refers to an exact nucleotide-to-nucleotide or amino acid-to-amino acid correspondence of two polynucleotides or polypeptide sequences, respectively. Two or more sequences (polynucleotide or amino acid) can be compared by determining their percent identity using standard techniques. Typically the percent identities between sequences are at least 70-75%, preferably 80-82%, more preferably 85-90%, even more preferably 92%, still more preferably 95%, and most preferably 98% sequence identity.

Alternatively, the degree of sequence similarity between polynucleotides can be determined by hybridization of polynucleotides under conditions that allow formation of stable duplexes between homologous regions, followed by digestion with single-stranded-specific nuclease(s), and size determination of the digested fragments. Two nucleic acid, or two polypeptide sequences are substantially homologous to each other when the sequences exhibit at least about 70%-75%, preferably 80%-82%, more preferably 85%-90%, even more preferably 92%, still more preferably 95%, and most preferably 98% sequence identity over a defined length of the molecules, as determined using the methods known in the art. Conditions for hybridization are well-known to those of skill in the art. Hybridization stringency refers to the degree to which hybridization conditions disfavor the formation of hybrids containing mismatched nucleotides, with higher stringency correlated with a lower tolerance for mismatched hybrids. Factors that affect the stringency of hybridization are well-known to those of skill in the art and include, but are not limited to, temperature, pH, ionic strength, and concentration of organic solvents such as, for example, formamide and dimethylsulfoxide. As is known to those of skill in the art, hybridization stringency is increased by higher temperatures, lower ionic strength and lower solvent concentrations.

"Chromatin" is the nucleoprotein structure comprising the cellular genome. Cellular chromatin comprises nucleic acid, primarily DNA, and protein, including histones and non-histone chromosomal proteins. The majority of eukaryotic cellular chromatin exists in the form of nucleosomes, wherein a nucleosome core comprises approximately 150 base pairs of DNA associated with an octamer comprising two each of histones H2A, H2B, H3 and H4; and linker DNA (of variable length depending on the organism) extends between nucleosome cores. A molecule of histone H1 is generally associated with the linker DNA. For the purposes of the present disclosure, the term "chromatin" is meant to encompass all types of cellular nucleoprotein, both prokaryotic and eukaryotic. Cellular chromatin includes both chromosomal and episomal chromatin.

A "chromosome," is a chromatin complex comprising all or a portion of the genome of a cell. The genome of a cell is often characterized by its karyotype, which is the collection of all the chromosomes that comprise the genome of the cell. The genome of a cell can comprise one or more chromosomes.

An "episome" is a replicating nucleic acid, nucleoprotein complex or other structure comprising a nucleic acid that is not part of the chromosomal karyotype of a cell. Examples of episomes include plasmids and certain viral genomes.

An "accessible region" is a site in cellular chromatin in which a target site present in the nucleic acid can be bound by an exogenous molecule which recognizes the target site. Without wishing to be bound by any particular theory, it is believed that an accessible region is one that is not packaged into a nucleosomal structure. The distinct structure of an accessible region can often be detected by its sensitivity to chemical and enzymatic probes, for example, nucleases.

A "target site" or "target sequence" is a nucleic acid sequence that defines a portion of a nucleic acid to which a binding molecule will bind, provided sufficient conditions for binding exist.

An "exogenous" molecule is a molecule that is not normally present in a cell, but can be introduced into a cell by one or more genetic, biochemical or other methods. "Normal presence in the cell" is determined with respect to the particular developmental stage and environmental conditions of the cell. Thus, for example, a molecule that is present only during embryonic development of muscle is an exogenous molecule with respect to an adult muscle cell. Similarly, a molecule induced by heat shock is an exogenous molecule with respect to a non-heat-shocked cell. An exogenous molecule can comprise, for example, a functioning version of a malfunctioning endogenous molecule or a malfunctioning version of a normally-functioning endogenous molecule.

An exogenous molecule can be, among other things, a small molecule, such as is generated by a combinatorial chemistry process, or a macromolecule such as a protein, nucleic acid, carbohydrate, lipid, glycoprotein, lipoprotein, polysaccharide, any modified derivative of the above molecules, or any complex comprising one or more of the above molecules. Nucleic acids include DNA and RNA, can be single- or double-stranded; can be linear, branched or circular; and can be of any length. Nucleic acids include those capable of forming duplexes, as well as triplex-forming nucleic acids. See, for example, U.S. Pat. Nos. 5,176,996 and 5,422,251. Proteins include, but are not limited to, DNA-binding proteins, transcription factors, chromatin remodeling factors, methylated DNA binding proteins, polymerases, methylases, demethylases, acetylases, deacetylases, kinases, phosphatases, integrases, recombinases, ligases, topoisomerases, gyrases and helicases.

An exogenous molecule can be the same type of molecule as an endogenous molecule, e.g., an exogenous protein or nucleic acid. For example, an exogenous nucleic acid can comprise an infecting viral genome, a plasmid or episome introduced into a cell, or a chromosome that is not normally present in the cell. Methods for the introduction of exogenous molecules into cells are known to those of skill in the art and include, but are not limited to, lipid-mediated transfer (i.e., liposomes, including neutral and cationic lipids), electroporation, direct injection, cell fusion, particle bombardment, calcium phosphate co-precipitation, DEAE-dextran-mediated transfer and viral vector-mediated transfer. An exogeneous molecule can also be the same type of molecule as an endogenous molecule but derived from a different species than the cell is derived from. For example, a human nucleic acid sequence may be introduced into a cell line originally derived from a mouse or hamster.

By contrast, an "endogenous" molecule is one that is normally present in a particular cell at a particular developmental stage under particular environmental conditions. For example, an endogenous nucleic acid can comprise a chromosome, the genome of a mitochondrion, or other organelle, or a naturally-occurring episomal nucleic acid. Additional endogenous molecules can include proteins, for example, transcription factors and enzymes.

As used herein, the term "product of an exogenous nucleic acid" includes both polynucleotide and polypeptide products, for example, transcription products (polynucleotides such as RNA) and translation products (polypeptides).

A "fusion" molecule is a molecule in which two or more subunit molecules are linked, preferably covalently. The subunit molecules can be the same chemical type of molecule, or can be different chemical types of molecules. Examples of the first type of fusion molecule include, but are not limited to, fusion proteins (for example, a fusion between a ZFP or TALE DNA-binding domain and one or more activation domains) and fusion nucleic acids (for example, a nucleic acid encoding the fusion protein described supra). Examples of the second type of fusion molecule include, but are not limited to, a fusion between a triplex-forming nucleic acid and a polypeptide, and a fusion between a minor groove binder and a nucleic acid.

Expression of a fusion protein in a cell can result from delivery of the fusion protein to the cell or by delivery of a polynucleotide encoding the fusion protein to a cell, wherein the polynucleotide is transcribed, and the transcript is translated, to generate the fusion protein. Trans-splicing, polypeptide cleavage and polypeptide ligation can also be involved in expression of a protein in a cell. Methods for polynucleotide and polypeptide delivery to cells are presented elsewhere in this disclosure.

A "gene," for the purposes of the present disclosure, includes a DNA region encoding a gene product (see infra), as well as all DNA regions which regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites and locus control regions.

"Gene expression" refers to the conversion of the information, contained in a gene, into a gene product. A gene product can be the direct transcriptional product of a gene (e.g., mRNA, tRNA, rRNA, miRNA, antisense RNA, ribozyme, structural RNA or any other type of RNA) or a protein produced by translation of an mRNA. Gene products also include RNAs which are modified, by processes such as capping, polyadenylation, methylation, and editing, and proteins modified by, for example, methylation, acetylation, phosphorylation, ubiquitination, ADP-ribosylation, myristilation, and glycosylation.

"Modulation" of gene expression refers to a change in the activity of a gene. Modulation of expression can include, but is not limited to, gene activation and gene repression. Genome editing (e.g., cleavage, alteration, inactivation, activation, random mutation) can be used to modulate expression. Gene inactivation refers to any reduction in gene expression as compared to a cell has not been modified as described herein (e.g., by a ZFP, TALE and/or CRISPR/Cas system). Gene inactivation may be partial or complete.

A "region of interest" is any region of cellular chromatin, such as, for example, a gene or a non-coding sequence within or adjacent to a gene, in which it is desirable to bind an exogenous molecule. Binding can be for the purposes of targeted DNA cleavage and/or targeted recombination. A region of interest can be present in a chromosome, an episome, an organellar genome (e.g., mitochondrial, chloroplast), or an infecting viral genome, for example. A region of interest can be within the coding region of a gene, within transcribed non-coding regions such as, for example, leader sequences, trailer sequences or introns, or within non-transcribed regions, either upstream or downstream of the coding region. A region of interest can be as small as a single nucleotide pair or up to 2,000 nucleotide pairs in length, or any integral value of nucleotide pairs.

"Eukaryotic" cells include, but are not limited to, fungal cells (such as yeast), plant cells, animal cells, mammalian cells and human cells (e.g., T-cells).

"Secretory tissues" are those tissues in an animal that secrete products out of the individual cell into a lumen of some type which are typically derived from epithelium. Examples of secretory tissues that are localized to the gastrointestinal tract include the cells that line the gut, the pancreas, and the gallbladder. Other secretory tissues include the liver, tissues associated with the eye and mucous membranes such as salivary glands, mammary glands, the prostate gland, the pituitary gland and other members of the endocrine system. Additionally, secretory tissues include individual cells of a tissue type which are capable of secretion.

The terms "operative linkage" and "operatively linked" (or "operably linked") are used interchangeably with reference to a juxtaposition of two or more components (such as sequence elements), in which the components are arranged such that both components function normally and allow the possibility that at least one of the components can mediate a function that is exerted upon at least one of the other components. By way of illustration, a transcriptional regulatory sequence, such as a promoter, is operatively linked to a coding sequence if the transcriptional regulatory sequence controls the level of transcription of the coding sequence in response to the presence or absence of one or more transcriptional regulatory factors. A transcriptional regulatory sequence is generally operatively linked in cis with a coding sequence, but need not be directly adjacent to it. For example, an enhancer is a transcriptional regulatory sequence that is operatively linked to a coding sequence, even though they are not contiguous.

With respect to fusion polypeptides, the term "operatively linked" can refer to the fact that each of the components performs the same function in linkage to the other component as it would if it were not so linked. For example, with respect to a fusion polypeptide in which a ZFP, TALE or Cas DNA-binding domain is fused to an activation domain, the ZFP, TALE or Cas DNA-binding domain and the activation domain are in operative linkage if, in the fusion polypeptide, the ZFP, TALE of Cas DNA-binding domain portion is able to bind its target site and/or its binding site, while the activation domain is able to upregulate gene expression. When a fusion polypeptide in which a ZFP, TALE or Cas DNA-binding domain is fused to a cleavage domain, the ZFP, TALE or CasDNA-binding domain and the cleavage domain are in operative linkage if, in the fusion polypeptide, the ZFP, TALE or Cas DNA-binding domain portion is able to bind its target site and/or its binding site, while the cleavage domain is able to cleave DNA in the vicinity of the target site (e.g., 1 to 500 base pairs or any value therebetween on either side of the target site).

A "functional fragment" of a protein, polypeptide or nucleic acid is a protein, polypeptide or nucleic acid whose sequence is not identical to the full-length protein, polypeptide or nucleic acid, yet retains the same function as the full-length protein, polypeptide or nucleic acid. A functional fragment can possess more, fewer, or the same number of residues as the corresponding native molecule, and/or can contain one or more amino acid or nucleotide substitutions. Methods for determining the function of a nucleic acid (e.g., coding function, ability to hybridize to another nucleic acid) are well-known in the art. Similarly, methods for determining protein function are well-known. For example, the DNA-binding function of a polypeptide can be determined, for example, by filter-binding, electrophoretic mobility-shift, or immunoprecipitation assays. DNA cleavage can be assayed by gel electrophoresis. See Ausubel et al., supra. The ability of a protein to interact with another protein can be determined, for example, by co-immunoprecipitation, two-hybrid assays or complementation, both genetic and biochemical. See, for example, Fields et al. (1989) Nature 340:245-246; U.S. Pat. No. 5,585,245 and PCT WO 98/44350.

A "vector" is capable of transferring gene sequences to target cells. Typically, "vector construct," "expression vector," and "gene transfer vector," mean any nucleic acid construct capable of directing the expression of a gene of interest and which can transfer gene sequences to target cells. Thus, the term includes cloning, and expression vehicles, as well as integrating vectors.

A "reporter gene" or "reporter sequence" refers to any sequence that produces a protein product that is easily measured, preferably although not necessarily in a routine assay. Suitable reporter genes include, but are not limited to, sequences encoding proteins that mediate antibiotic resistance (e.g., ampicillin resistance, neomycin resistance, G418 resistance, puromycin resistance), sequences encoding colored or fluorescent or luminescent proteins (e.g., green fluorescent protein, enhanced green fluorescent protein, red fluorescent protein, luciferase), and proteins which mediate enhanced cell growth and/or gene amplification (e.g., dihydrofolate reductase). Epitope tags include, for example, one or more copies of FLAG, His, myc, Tap, HA or any detectable amino acid sequence. "Expression tags" include sequences that encode reporters that may be operably linked to a desired gene sequence in order to monitor expression of the gene of interest.

A "safe harbor" locus is a locus within the genome wherein a gene may be inserted without any deleterious effects on the host cell. Most beneficial is a safe harbor locus in which expression of the inserted gene sequence is not perturbed by any read-through expression from neighboring genes. Non-limiting examples of safe harbor loci in mammalian cells are the AAVS1, HPRT, albumin and CCR5 genes in human cells, and Rosa26 in murine cells (see, e.g., U.S. Pat. Nos. 7,888,121; 7,972,854; 7,914,796; 7,951,925; 8,110,379; 8,409,861; 8,586,526; U.S. Patent Publications 20030232410; 20050208489; 20050026157; 20060063231; 20080159996; 201000218264; 20120017290; 20110265198; 20130137104; 20130122591; 20130177983 and 20130177960) and the Zp15 locus in plants (see U.S. Pat. No. 8,329,986).

The terms "subject" and "patient" are used interchangeably and refer to mammals such as human patients and non-human primates, as well as experimental animals such as rabbits, dogs, cats, rats, mice, and other animals. Accordingly, the term "subject" or "patient" as used herein means any mammalian patient or subject to which the or stem cells of the invention can be administered. Subjects of the present invention include those that have been exposed to one or more chemical toxins, including, for example, a nerve toxin.

"Stemness" refers to the relative ability of any cell to act in a stem cell-like manner, i.e., the degree of toti-, pluri-, or oligopotentcy and expanded or indefinite self-renewal that any particular stem cell may have.

Nucleases

Described herein are compositions, particularly nucleases, such as TALEs, homing endonucleases, CRISPR/Cas and/or Ttago guide RNAs, that are useful for in vivo cleavage of a donor molecule carrying a transgene and nucleases for cleavage of the genome of a cell such that the transgene is integrated into the genome in a targeted manner. In certain embodiments, one or more of the nucleases are naturally occurring. In other embodiments, one or more of the nucleases are non-naturally occurring, i.e., engineered in the DNA-binding molecule (also referred to as a DNA-binding domain) and/or cleavage domain. For example, the DNA-binding domain of a naturally-occurring nuclease may be altered to bind to a selected target site (e.g., a ZFP, TALE and/or sgRNA of CRISPR/Cas that is engineered to bind to a selected target site). In other embodiments, the nuclease comprises heterologous DNA-binding and cleavage domains (e.g., zinc finger nucleases; TAL-effector domain DNA binding proteins; meganuclease DNA-binding domains with heterologous cleavage domains). In other embodiments, the nuclease comprises a system such as the CRISPR/Cas of Ttago system.

A. DNA-Binding Domains

In certain embodiments, the composition and methods described herein employ a meganuclease (homing endonuclease) DNA-binding domain for binding to the donor molecule and/or binding to the region of interest in the genome of the cell. Naturally-occurring meganucleases recognize 15-40 base-pair cleavage sites and are commonly grouped into four families: the LAGLIDADG family ("LAGLIDADG" disclosed as SEQ ID NO: 26), the GIY-YIG family, the His-Cyst box family and the HNH family. Exemplary homing endonucleases include I-SceI, I-CeuI, PI-PspI, PI-Sce, I-SceIV, I-CsmI, I-PanI, I-SceII, I-PpoI, I-SceIII, I-CreI, I-TevI, I-TevII and I-TevIII. Their recognition sequences are known. See also U.S. Pat. Nos. 5,420,032; 6,833,252; Belfort et al. (1997) Nucleic AcidsRes. 25:3379-3388; Dujon et al. (1989) Gene 82:115-118; Perler et al. (1994) Nucleic Acids Res. 22, 1125-1127; Jasin (1996) Trends Genet. 12:224-228; Gimble et al. (1996) J. Mol. Biol. 263:163-180; Argast et al. (1998) J. Mol. Biol. 280:345-353 and the New England Biolabs catalogue.

In certain embodiments, the methods and compositions described herein make use of a nuclease that comprises an engineered (non-naturally occurring) homing endonuclease (meganuclease). The recognition sequences of homing endonucleases and meganucleases such as I-SceI, I-CeuI, PI-PspI, PI-Sce, I-SceIV, I-CsmI, I-PanI, I-SceII, I-PpoI, I-SceIII, I-CreI, I-TevI, I-TevII and I-TevIII are known. See also U.S. Pat. Nos. 5,420,032; 6,833,252; Belfort et al. (1997) *Nucleic Acids Res.* 25:3379-3388; Dujon et al. (1989) *Gene* 82:115-118; Perler et al. (1994) Nucleic Acids Res. 22, 1125-1127; Jasin (1996) *Trends Genet.* 12:224-228; Gimble et al. (1996) *J. Mol. Biol.* 263:163-180; Argast et al. (1998) *J. Mol. Biol.* 280:345-353 and the New England Biolabs catalogue. In addition, the DNA-binding specificity of homing endonucleases and meganucleases can be engineered to bind non-natural target sites. See, for example, Chevalier et al. (2002) *Molec. Cell* 10:895-905; Epinat et al. (2003) *Nucleic Acids Res.* 31:2952-2962; Ashworth et al. (2006) *Nature* 441:656-659; Paques et al. (2007) *Current Gene Therapy* 7:49-66; U.S. Patent Publication No. 20070117128. The DNA-binding domains of the homing endonucleases and meganucleases may be altered in the context of the nuclease as a whole (i.e., such that the nuclease includes the cognate cleavage domain) or may be fused to a heterologous cleavage domain.

In other embodiments, the DNA-binding domain of one or more of the nucleases used in the methods and compositions described herein comprises a naturally occurring or engineered (non-naturally occurring) TAL effector DNA binding domain. See, e.g., U.S. Pat. No. 8,586,526, incorporated by reference in its entirety herein. The plant pathogenic bacteria of the genus *Xanthomonas* are known to cause many diseases in important crop plants. Pathogenicity of *Xanthomonas* depends on a conserved type III secretion (T3S) system which injects more than 25 different effector proteins into the plant cell. Among these injected proteins are transcription activator-like (TAL) effectors which mimic plant transcriptional activators and manipulate the plant transcriptome (see Kay et al (2007) *Science* 318:648-651). These proteins contain a DNA binding domain and a transcriptional activation domain. One of the most well characterized TAL-effectors is AvrBs3 from *Xanthomonas campestgris* pv. *Vesicatoria* (see Bonas et al (1989) *Mol Gen Genet* 218: 127-136 and WO2010079430). TAL-effectors contain a centralized domain of tandem repeats, each repeat containing approximately 34 amino acids, which are key to the DNA binding specificity of these proteins. In addition, they contain a nuclear localization sequence and an acidic transcriptional activation domain (for a review see Schornack S, et al (2006) *J Plant Physiol* 163(3): 256-272). In addition, in the phytopathogenic bacteria *Ralstonia solanacearum* two genes, designated brg11 and hpx17 have been found that are homologous to the AvrBs3 family of *Xanthomonas* in the *R. solanacearum* biovar 1 strain GMI1000 and in the biovar 4 strain RS1000 (See Heuer et al (2007) *Appl and Envir Micro* 73(13): 4379-4384). These genes are 98.9% identical in nucleotide sequence to each other but differ by a deletion of 1,575 bp in the repeat domain of hpx17. However, both gene products have less than 40% sequence identity with AvrBs3 family proteins of *Xanthomonas*. See, e.g., U.S. Pat. No. 8,586,526, incorporated by reference in its entirety herein.

Specificity of these TAL effectors depends on the sequences found in the tandem repeats. The repeated sequence comprises approximately 102 bp and the repeats are typically 91-100% homologous with each other (Bonas et al, ibid). Polymorphism of the repeats is usually located at positions 12 and 13 and there appears to be a one-to-one correspondence between the identity of the hypervariable diresidues (RVDs) at positions 12 and 13 with the identity of the contiguous nucleotides in the TAL-effector's target sequence (see Moscou and Bogdanove, (2009) *Science* 326:1501 and Boch et al (2009) *Science* 326:1509-1512). Experimentally, the natural code for DNA recognition of these TAL-effectors has been determined such that an HD sequence at positions 12 and 13 leads to a binding to cytosine (C), NG binds to T, NI to A, C, G or T, NN binds to A or G, and ING binds to T. These DNA binding repeats have been assembled into proteins with new combinations and numbers of repeats, to make artificial transcription factors that are able to interact with new sequences and activate the expression of a non-endogenous reporter gene in plant cells (Boch et al, ibid). Engineered TAL proteins have been linked to a FokI cleavage half domain to yield a TAL effector domain nuclease fusion (TALEN) exhibiting activity in a yeast reporter assay (plasmid based target). See, e.g., U.S. Pat. No. 8,586,526; Christian et al ((2010)<Genetics epub 10.1534/genetics.110.120717).

In certain embodiments, the DNA binding domain of one or more of the nucleases used for in vivo cleavage and/or targeted cleavage of the genome of a cell comprises a zinc finger protein. Preferably, the zinc finger protein is non-naturally occurring in that it is engineered to bind to a target site of choice. See, for example, See, for example, Beerli et al. (2002) *Nature Biotechnol.* 20:135-141; Pabo et al. (2001) *Ann. Rev. Biochem.* 70:313-340; Isalan et al. (2001) *Nature Biotechnol.* 19:656-660; Segal et al. (2001) *Curr. Opin. Biotechnol.* 12:632-637; Choo et al. (2000) *Curr. Opin. Struct. Biol.* 10:411-416; U.S. Pat. Nos. 6,453,242; 6,534,261; 6,599,692; 6,503,717; 6,689,558; 7,030,215; 6,794,136; 7,067,317; 7,262,054; 7,070,934; 7,361,635; 7,253,273; and U.S. Patent Publication Nos. 2005/0064474; 2007/0218528; 2005/0267061, all incorporated herein by reference in their entireties.

An engineered zinc finger binding domain can have a novel binding specificity, compared to a naturally-occurring zinc finger protein. Engineering methods include, but are not limited to, rational design and various types of selection. Rational design includes, for example, using databases comprising triplet (or quadruplet) nucleotide sequences and individual zinc finger amino acid sequences, in which each triplet or quadruplet nucleotide sequence is associated with one or more amino acid sequences of zinc fingers which bind the particular triplet or quadruplet sequence. See, for example, co-owned U.S. Pat. Nos. 6,453,242 and 6,534,261, incorporated by reference herein in their entireties.

Exemplary selection methods, including phage display and two-hybrid systems, are disclosed in U.S. Pat. Nos. 5,789,538; 5,925,523; 6,007,988; 6,013,453; 6,410,248; 6,140,466; 6,200,759; and 6,242,568; as well as WO 98/37186; WO 98/53057; WO 00/27878; and WO 01/88197. In addition, enhancement of binding specificity for zinc finger binding domains has been described, for example, in co-owned WO 02/077227.

In addition, as disclosed in these and other references, zinc finger domains and/or multi-fingered zinc finger proteins may be linked together using any suitable linker sequences, including for example, linkers of 5 or more amino acids in length. See, also, U.S. Pat. Nos. 8,772,453; 6,479,626; 6,903,185; and 7,153,949 for exemplary linker sequences-. The proteins described herein may include any combination of suitable linkers between the individual zinc fingers of the protein.

Selection of target sites; ZFPs and methods for design and construction of fusion proteins (and polynucleotides encoding same) are known to those of skill in the art and described in detail in U.S. Pat. Nos. 6,140,081; 5,789,538; 6,453,242; 6,534,261; 5,925,523; 6,007,988; 6,013,453; 6,200,759; WO 95/19431; WO 96/06166; WO 98/53057; WO 98/54311; WO 00/27878; WO 01/60970 WO 01/88197; WO 02/099084; WO 98/53058; WO 98/53059; WO 98/53060; WO 02/016536 and WO 03/016496.

In addition, as disclosed in these and other references, zinc finger domains and/or multi-fingered zinc finger proteins may be linked together using any suitable linker sequences, including for example, linkers of 5 or more amino acids in length. See, also, U.S. Pat. Nos. 6,479,626; 6,903,185; and 7,153,949 for exemplary linker sequences 6 or more amino acids in length. The proteins described herein may include any combination of suitable linkers between the individual zinc fingers of the protein.

In certain embodiments, the DNA-binding domain is part of a CRISPR/Cas nuclease system, including, for example a single guide RNA (sgRNA). See, e.g., U.S. Pat. No. 8,697, 359 and U.S. Patent Publication No. 20150056705. The CRISPR (clustered regularly interspaced short palindromic repeats) locus, which encodes RNA components of the system, and the Cas (CRISPR-associated) locus, which encodes proteins (Jansen et al., 2002. *Mol. Microbiol.* 43: 1565-1575; Makarova et al., 2002. *Nucleic Acids Res.* 30: 482-496; Makarova et al., 2006. *Biol. Direct* 1: 7; Haft et al., 2005. *PLoSComput. Biol.* 1: e60) make up the gene sequences of the CRISPR/Cas nuclease system. CRISPR loci in microbial hosts contain a combination of CRISPR-associated (Cas) genes as well as non-coding RNA elements capable of programming the specificity of the CRISPR-mediated nucleic acid cleavage.

The Type II CRISPR is one of the most well characterized systems and carries out targeted DNA double-strand break in four sequential steps. First, two non-coding RNA, the pre-crRNA array and tracrRNA, are transcribed from the CRISPR locus. Second, tracrRNA hybridizes to the repeat regions of the pre-crRNA and mediates the processing of pre-crRNA into mature crRNAs containing individual spacer sequences. Third, the mature crRNA:tracrRNA complex directs Cas9 to the target DNA via Watson-Crick base-pairing between the spacer on the crRNA and the protospacer on the target DNA next to the protospacer adjacent motif (PAM), an additional requirement for target recognition. Finally, Cas9 mediates cleavage of target DNA to create a double-stranded break within the protospacer. Activity of the CRISPR/Cas system comprises of three steps: (i) insertion of alien DNA sequences into the CRISPR array to prevent future attacks, in a process called 'adaptation', (ii) expression of the relevant proteins, as well as expression and processing of the array, followed by (iii) RNA-mediated interference with the alien nucleic acid. Thus, in the bacterial cell, several of the so-called 'Cas' proteins are involved with the natural function of the CRISPR/Cas system and serve roles in functions such as insertion of the alien DNA etc.

In certain embodiments, Cas protein may be a "functional derivative" of a naturally occurring Cas protein. A "functional derivative" of a native sequence polypeptide is a compound having a qualitative biological property in common with a native sequence polypeptide. "Functional derivatives" include, but are not limited to, fragments of a native sequence and derivatives of a native sequence polypeptide and its fragments, provided that they have a biological activity in common with a corresponding native sequence polypeptide. A biological activity contemplated herein is the ability of the functional derivative to hydrolyze a DNA substrate into fragments. The term "derivative" encompasses both amino acid sequence variants of polypeptide, covalent modifications, and fusions thereof. Suitable derivatives of a Cas polypeptide or a fragment thereof include but are not limited to, mutants, fusions, covalent modifications of Cas protein or a fragment thereof. Cas protein, which includes Cas protein or a fragment thereof, as well as derivatives of Cas protein or a fragment thereof, may be obtainable from a cell or synthesized chemically or by a combination of these two procedures. The cell may be a cell that naturally produces Cas protein, or a cell that naturally produces Cas protein and is genetically engineered to produce the endogenous Cas protein at a higher expression level or to produce a Cas protein from an exogenously introduced nucleic acid, which nucleic acid encodes a Cas that is same or different from the endogenous Cas. In some cases, the cell does not naturally produce Cas protein and is genetically engineered to produce a Cas protein. Additional non-limiting examples of RNA guided nucleases that may be used in addition to and/or instead of Cas proteins include Class 2 CRISPR proteins such as Cpf1. See, e.g., Zetsche et al. (2015) *Cell* 163:1-13.

In some embodiments, the DNA binding domain is part of a TtAgo system (see Swarts et al, ibid; Sheng et al, ibid). In eukaryotes, gene silencing is mediated by the Argonaute (Ago) family of proteins. In this paradigm, Ago is bound to small (19-31 nt) RNAs. This protein-RNA silencing complex recognizes target RNAs via Watson-Crick base pairing between the small RNA and the target and endonucleolytically cleaves the target RNA (Vogel (2014) *Science* 344: 972-973). In contrast, prokaryotic Ago proteins bind to small single-stranded DNA fragments and likely function to detect and remove foreign (often viral) DNA (Yuan et al., (2005) *Mol. Cell* 19, 405; Olovnikov, et al. (2013) *Mol. Cell* 51, 594; Swarts et al., ibid). Exemplary prokaryotic Ago proteins include those from *Aquifex aeolicus, Rhodobacter sphaeroides*, and *Thermus thermophilus*.

One of the most well-characterized prokaryotic Ago protein is the one from *T. thermophilus* (TtAgo; Swarts et al. ibid). TtAgo associates with either 15 nt or 13-25 nt single-stranded DNA fragments with 5' phosphate groups. This "guide DNA" bound by TtAgo serves to direct the protein-DNA complex to bind a Watson-Crick complementary DNA sequence in a third-party molecule of DNA. Once the sequence information in these guide DNAs has allowed identification of the target DNA, the TtAgo-guide DNA complex cleaves the target DNA. Such a mechanism is also supported by the structure of the TtAgo-guide DNA complex while bound to its target DNA (G. Sheng et al., ibid). Ago from *Rhodobacter sphaeroides* (RsAgo) has similar properties (Olivnikov et al. ibid).

Exogenous guide DNAs of arbitrary DNA sequence can be loaded onto the TtAgo protein (Swarts et al. ibid.). Since the specificity of TtAgo cleavage is directed by the guide DNA, a TtAgo-DNA complex formed with an exogenous, investigator-specified guide DNA will therefore direct TtAgo target DNA cleavage to a complementary investigator-specified target DNA. In this way, one may create a targeted double-strand break in DNA. Use of the TtAgo-guide DNA system (or orthologous Ago-guide DNA systems from other organisms) allows for targeted cleavage of genomic DNA within cells. Such cleavage can be either single- or double-stranded. For cleavage of mammalian genomic DNA, it would be preferable to use of a version of TtAgo codon optimized for expression in mammalian cells. Further, it might be preferable to treat cells with a TtAgo-DNA complex formed in vitro where the TtAgo protein is fused to a cell-penetrating peptide. Further, it might be preferable to use a version of the TtAgo protein that has been altered via mutagenesis to have improved activity at 37 degrees Celcius. Ago-RNA-mediated DNA cleavage could be used to effect a panoply of outcomes including gene knock-out, targeted gene addition, gene correction, targeted gene deletion using techniques standard in the art for exploitation of DNA breaks.

Thus, the nuclease comprises a DNA-binding domain in that specifically binds to a target site in any gene into which it is desired to insert a donor (transgene).

B. Cleavage Domains

Any suitable cleavage domain can be operatively linked to a DNA-binding domain to form a nuclease. For example, ZFP DNA-binding domains have been fused to nuclease domains to create ZFNs—a functional entity that is able to recognize its intended nucleic acid target through its engineered (ZFP) DNA binding domain and cause the DNA to be cut near the ZFP binding site via the nuclease activity. See, e.g., Kim et al. (1996) *Proc Natl Acad Sci USA* 93(3):1156-1160. More recently, ZFNs have been used for genome modification in a variety of organisms. See, for example, United States Patent Publications 20030232410; 20050208489; 20050026157; 20050064474; 20060188987; 20060063231; and International Publication WO 07/014275. Likewise, TALE DNA-binding domains have been fused to nuclease domains to create TALENs. See, e.g., U.S. Pat. No. 8,586,526. CRISPR/Cas nuclease systems comprising single guide RNAs (sgRNAs) that bind to DNA and associate with cleavage domains (e.g., Cas domains) to induce targeted cleavage have also been described. See, e.g., U.S. Pat. Nos. 8,697,359 and 8,932,814 and U.S. Patent Publication No. 20150056705.

As noted above, the cleavage domain may be heterologous to the DNA-binding domain, for example a zinc finger DNA-binding domain and a cleavage domain from a nuclease or a TALEN DNA-binding domain and a cleavage domain from a nuclease; a sgRNA DNA-binding domain and a cleavage domain from a nuclease (CRISPR/Cas); and/or meganuclease DNA-binding domain and cleavage domain from a different nuclease. Heterologous cleavage domains can be obtained from any endonuclease or exonuclease. Exemplary endonucleases from which a cleavage domain can be derived include, but are not limited to, restriction endonucleases and homing endonucleases. See, for example, 2002-2003 Catalogue, New England Biolabs, Beverly, Mass.; and Belfort et al. (1997) *Nucleic Acids Res.* 25:3379-3388. Additional enzymes which cleave DNA are known (e.g., S1 Nuclease; mung bean nuclease; pancreatic DNase I; micrococcal nuclease; yeast HO endonuclease; see also Linn et al. (eds.) *Nucleases*, Cold Spring Harbor Laboratory Press, 1993). One or more of these enzymes (or functional fragments thereof) can be used as a source of cleavage domains and cleavage half-domains.

Similarly, a cleavage half-domain can be derived from any nuclease or portion thereof, as set forth above, that requires dimerization for cleavage activity. In general, two fusion proteins are required for cleavage if the fusion proteins comprise cleavage half-domains. Alternatively, a single protein comprising two cleavage half-domains can be used. The two cleavage half-domains can be derived from the same endonuclease (or functional fragments thereof), or each cleavage half-domain can be derived from a different endonuclease (or functional fragments thereof). In addition, the target sites for the two fusion proteins are preferably disposed, with respect to each other, such that binding of the two fusion proteins to their respective target sites places the cleavage half-domains in a spatial orientation to each other that allows the cleavage half-domains to form a functional cleavage domain, e.g., by dimerizing. Thus, in certain embodiments, the near edges of the target sites are separated by 5-8 nucleotides or by 15-18 nucleotides. However any integral number of nucleotides or nucleotide pairs can intervene between two target sites (e.g., from 2 to 50 nucleotide pairs or more). In general, the site of cleavage lies between the target sites.

Restriction endonucleases (restriction enzymes) are present in many species and are capable of sequence-specific binding to DNA (at a recognition site), and cleaving DNA at or near the site of binding. Certain restriction enzymes (e.g., Type IIS) cleave DNA at sites removed from the recognition site and have separable binding and cleavage domains. For example, the Type IIS enzyme Fok I catalyzes double-stranded cleavage of DNA, at 9 nucleotides from its recognition site on one strand and 13 nucleotides from its recognition site on the other. See, for example, U.S. Pat. Nos. 5,356,802; 5,436,150 and 5,487,994; as well as Li et al. (1992) *Proc. Natl. Acad. Sci. USA* 89:4275-4279; Li et al. (1993) *Proc. Natl. Acad. Sci. USA* 90:2764-2768; Kim et al. (1994a) *Proc. Natl. Acad. Sci. USA* 91:883-887; Kim et al. (1994b) *J. Biol. Chem.* 269:31,978-31,982. Thus, in one embodiment, fusion proteins comprise the cleavage domain (or cleavage half-domain) from at least one Type IIS restriction enzyme and one or more zinc finger binding domains, which may or may not be engineered.

An exemplary Type IIS restriction enzyme, whose cleavage domain is separable from the binding domain, is Fok I. This particular enzyme is active as a dimer. Bitinaite et al. (1998) *Proc. Natl. Acad. Sci. USA* 95: 10,570-10,575. Accordingly, for the purposes of the present disclosure, the portion of the Fok I enzyme used in the disclosed fusion proteins is considered a cleavage half-domain. Thus, for targeted double-stranded cleavage and/or targeted replacement of cellular sequences using zinc finger-Fok I fusions, two fusion proteins, each comprising a FokI cleavage half-domain, can be used to reconstitute a catalytically active cleavage domain. Alternatively, a single polypeptide molecule containing a zinc finger binding domain and two Fok I cleavage half-domains can also be used. Parameters for targeted cleavage and targeted sequence alteration using zinc finger-Fok I fusions are provided elsewhere in this disclosure.

A cleavage domain or cleavage half-domain can be any portion of a protein that retains cleavage activity, or that retains the ability to multimerize (e.g., dimerize) to form a functional cleavage domain.

Exemplary Type IIS restriction enzymes are described in U.S. Pat. No. 7,888,121, incorporated herein in its entirety. Additional restriction enzymes also contain separable binding and cleavage domains, and these are contemplated by the present disclosure. See, for example, Roberts et al. (2003) *Nucleic Acids Res.* 31:418-420.

In certain embodiments, the cleavage domain comprises one or more engineered cleavage half-domain (also referred to as dimerization domain mutants) that minimize or prevent homodimerization, as described, for example, in U.S. Pat. Nos. 8,772,453; 8,623,618; 8,409,861; 8,034,598; 7,914, 796; and 7,888,121, the disclosures of all of which are incorporated by reference in their entireties herein. Amino acid residues at positions 446, 447, 479, 483, 484, 486, 487, 490, 491, 496, 498, 499, 500, 531, 534, 537, and 538 of FokI are all targets for influencing dimerization of the FokI cleavage half-domains.

Exemplary engineered cleavage half-domains of FokI that form obligate heterodimers include a pair in which a first cleavage half-domain includes mutations at amino acid residues at positions 490 and 538 of FokI and a second cleavage half-domain includes mutations at amino acid residues 486 and 499.

Thus, in one embodiment, a mutation at 490 replaces Glu (E) with Lys (K); the mutation at 538 replaces Iso (I) with Lys (K); the mutation at 486 replaced Gln (Q) with Glu (E); and the mutation at position 499 replaces Iso (I) with Lys (K). Specifically, the engineered cleavage half-domains described herein were prepared by mutating positions 490 (E→K) and 538 (I→K) in one cleavage half-domain to produce an engineered cleavage half-domain designated "E490K:I538K" and by mutating positions 486 (Q→E) and 499 (I→L) in another cleavage half-domain to produce an engineered cleavage half-domain designated "Q486E: I499L". The engineered cleavage half-domains described herein are obligate heterodimer mutants in which aberrant cleavage is minimized or abolished. U.S. Pat. Nos. 7,914,796 and 8,034,598, the disclosures of which are incorporated by reference in their entireties. In certain embodiments, the engineered cleavage half-domain comprises mutations at positions 486, 499 and 496 (numbered relative to wild-type FokI), for instance mutations that replace the wild type Gln (Q) residue at position 486 with a Glu (E) residue, the wild type Iso (I) residue at position 499 with a Leu (L) residue and the wild-type Asn (N) residue at position 496 with an Asp (D) or Glu (E) residue (also referred to as a "ELD" and "ELE" domains, respectively). In other embodiments, the engineered cleavage half-domain comprises mutations at positions 490, 538 and 537 (numbered relative to wild-type FokI), for instance mutations that replace the wild type Glu (E) residue at position 490 with a Lys (K) residue, the wild type Iso (I) residue at position 538 with a Lys (K) residue, and the wild-type His (H) residue at position 537 with a Lys (K) residue or a Arg (R) residue (also referred to as "KKK" and "KKR" domains, respectively). In other embodiments, the engineered cleavage half-domain comprises mutations at positions 490 and 537 (numbered relative to wild-type FokI), for instance mutations that replace the wild type Glu (E) residue at position 490 with a Lys (K) residue and the wild-type His (H) residue at position 537 with a Lys (K) residue or a Arg (R) residue (also referred to as "KIK" and "KIR" domains, respectively). See, e.g., U.S. Pat. No. 8,772,453. In other embodiments, the engineered cleavage half domain comprises the "Sharkey" and/or "Sharkey'" mutations (see Guo et al, (2010) *J. Mol. Biol.* 400(1):96-107).

Engineered cleavage half-domains described herein can be prepared using any suitable method, for example, by site-directed mutagenesis of wild-type cleavage half-domains (Fok I) as described in U.S. Patent Publication Nos. 20050064474; 20080131962; and 20110201055.

Alternatively, nucleases may be assembled in vivo at the nucleic acid target site using so-called "split-enzyme" technology (see, e.g. U.S. Patent Publication No. 20090068164). Components of such split enzymes may be expressed either on separate expression constructs, or can be linked in one open reading frame where the individual components are separated, for example, by a self-cleaving 2A peptide or IRES sequence. Components may be individual zinc finger binding domains or domains of a meganuclease nucleic acid binding domain.

Nucleases can be screened for activity prior to use, for example in a yeast-based chromosomal system as described in U.S. Pat. No. 8,563,314. Expression of the nuclease may be under the control of a constitutive promoter or an inducible promoter, for example the galactokinase promoter which is activated (de-repressed) in the presence of raffinose and/or galactose and repressed in presence of glucose.

The Cas9 related CRISPR/Cas system comprises two RNA non-coding components: tracrRNA and a pre-crRNA array containing nuclease guide sequences (spacers) interspaced by identical direct repeats (DRs). To use a CRISPR/Cas system to accomplish genome engineering, both functions of these RNAs must be present (see Cong et al, (2013) *Sciencexpress* 1/10.1126/science 1231143). In some embodiments, the tracrRNA and pre-crRNAs are supplied via separate expression constructs or as separate RNAs. In other embodiments, a chimeric RNA is constructed where an engineered mature crRNA (conferring target specificity) is fused to a tracrRNA (supplying interaction with the Cas9) to create a chimeric cr-RNA-tracrRNA hybrid (also termed a single guide RNA). (see Jinek ibid and Cong, ibid).

Target Sites

As described in detail above, DNA domains can be engineered to bind to any sequence of choice. An engineered DNA-binding domain can have a novel binding specificity, compared to a naturally-occurring DNA-binding domain. Engineering methods include, but are not limited to, rational design and various types of selection. Rational design includes, for example, using databases comprising triplet (or quadruplet) nucleotide sequences and individual zinc finger amino acid sequences, in which each triplet or quadruplet nucleotide sequence is associated with one or more amino acid sequences of zinc fingers which bind the particular triplet or quadruplet sequence. See, for example, co-owned U.S. Pat. Nos. 6,453,242 and 6,534,261, incorporated by reference herein in their entireties. Rational design of TAL-effector domains can also be performed. See, e.g., U.S. Pat. No. 8,586,526.

Exemplary selection methods applicable to DNA-binding domains, including phage display and two-hybrid systems, are disclosed in U.S. Pat. Nos. 8,586,526; 5,789,538; 5,925,523; 6,007,988; 6,013,453; 6,410,248; 6,140,466; 6,200,759; and 6,242,568; as well as WO 98/37186; WO 98/53057; WO 00/27878; WO 01/88197 and GB 2,338,237. In addition, enhancement of binding specificity for zinc finger binding domains has been described, for example, in co-owned WO 02/077227.

Selection of target sites; nucleases and methods for design and construction of fusion proteins (and polynucleotides encoding same) are known to those of skill in the art and described in detail in U.S. Patent Application Publication Nos. 20050064474 and 20060188987, incorporated by reference in their entireties herein.

In addition, as disclosed in these and other references, DNA-binding domains (e.g., multi-fingered zinc finger proteins) may be linked together using any suitable linker sequences, including for example, linkers of 5 or more amino acids. See, e.g., U.S. Pat. Nos. 6,479,626; 6,903,185; and 7,153,949 for exemplary linker sequences 6 or more amino acids in length. The proteins described herein may include any combination of suitable linkers between the individual DNA-binding domains of the protein. See, also, U.S. Pat. No. 8,586,526.

As noted above, the DNA-binding domains of the nucleases may be targeted to any gene. In certain embodiments, the nuclease (DNA-binding domain component) is targeted to an endogenous albumin gene. See, e.g., U.S. Patent Publication Nos. 20130177983; 20130177960 and 20150056705. In other embodiments, the nuclease targets another "safe harbor" locus, which includes, by way of example only, the AAVS1, HPRT, and CCR5 genes in human cells, and Rosa26 in murine cells (see, e.g., U.S. Pat.

Nos. 7,888,121; 7,972,854; 7,914,796; 7,951,925; 8,110,379; 8,409,861; 8,586,526; U.S. Patent Publications 20030232410; 20050208489; 20050026157; 20060063231; 20080159996; 201000218264; 20120017290; 20110265198; 20130137104; 20130122591) and the Zp15 locus in plants (see U.S. Pat. No. 8,329,986).

Donors

The present disclosure relates to nuclease-mediated targeted integration of an exogenous sequence into the genome of an HSC/PC. As noted above, insertion of an exogenous sequence (also called a "donor sequence" or "donor" or "transgene"), for example for correction of a mutant gene or for increased expression of a wild-type gene or for expression of a transgene. It will be readily apparent that the donor sequence is typically not identical to the genomic sequence where it is placed. A donor sequence can contain a non-homologous sequence flanked by two regions of homology to allow for efficient HDR at the location of interest. Additionally, donor sequences can comprise a vector molecule containing sequences that are not homologous to the region of interest in cellular chromatin. A donor molecule can contain several, discontinuous regions of homology to cellular chromatin. For example, for targeted insertion of sequences not normally present in a region of interest, said sequences can be present in a donor nucleic acid molecule and flanked by regions of homology to sequence in the region of interest.

Described herein are methods of targeted insertion of any polynucleotides for insertion into a chosen location. Polynucleotides for insertion can also be referred to as "exogenous" polynucleotides, "donor" polynucleotides or molecules or "transgenes." The donor polynucleotide can be DNA or RNA, single-stranded and/or double-stranded and can be introduced into a cell in linear or circular form. See, e.g., U.S. Patent Publication Nos. 20100047805 and 20110207221. The donor sequence(s) are preferably contained within a DNA MC, which may be introduced into the cell in circular or linear form. If introduced in linear form, the ends of the donor sequence can be protected (e.g., from exonucleolytic degradation) by methods known to those of skill in the art. For example, one or more dideoxynucleotide residues are added to the 3' terminus of a linear molecule and/or self-complementary oligonucleotides are ligated to one or both ends. See, for example, Chang et al. (1987) *Proc. Natl. Acad. Sci. USA* 84:4959-4963; Nehls et al. (1996) *Science* 272:886-889. Additional methods for protecting exogenous polynucleotides from degradation include, but are not limited to, addition of terminal amino group(s) and the use of modified internucleotide linkages such as, for example, phosphorothioates, phosphoramidates, and O-methyl ribose or deoxyribose residues.

A polynucleotide can be introduced into a cell as part of a vector molecule having additional sequences such as, for example, replication origins, promoters and genes encoding antibiotic resistance. Moreover, donor polynucleotides can be introduced as naked nucleic acid, as nucleic acid complexed with an agent such as a liposome or poloxamer, or can be delivered by viruses (e.g., adenovirus, AAV, herpesvirus, retrovirus, lentivirus and integrase defective lentivirus (IDLV)).

In certain embodiments, the double-stranded donor includes sequences (e.g., coding sequences, also referred to as transgenes) greater than 1 kb in length, for example between 2 and 200 kb, between 2 and 10 kb (or any value therebetween). The double-stranded donor also includes at least one nuclease target site, for example. In certain embodiments, the donor includes at least 2 target sites, for example for a pair of ZFNs or TALENs. Typically, the nuclease target sites are outside the transgene sequences, for example, 5' and/or 3' to the transgene sequences, for cleavage of the transgene. The nuclease cleavage site(s) may be for any nuclease(s). In certain embodiments, the nuclease target site(s) contained in the double-stranded donor are for the same nuclease(s) used to cleave the endogenous target into which the cleaved donor is integrated via homology-independent methods.

The donor can be inserted so that its expression is driven by the endogenous promoter at the integration site, namely the promoter that drives expression of the endogenous gene into which the donor is inserted (e.g., albumin or HPRT). However, it will be apparent that the donor may comprise a promoter and/or enhancer, for example a constitutive promoter or an inducible or tissue specific promoter.

The donor molecule may be inserted into an endogenous gene such that all, some or none of the endogenous gene (e.g., albumin) is expressed. In other embodiments, the transgene (e.g., with or without albumin encoding sequences) is integrated into any endogenous locus, for example a safe-harbor locus. See, e.g., U.S. patent publications 20080299580; 20080159996 and 201000218264.

Furthermore, although not required for expression, exogenous sequences may also include transcriptional or translational regulatory sequences, for example, promoters, enhancers, insulators, internal ribosome entry sites, sequences encoding 2A peptides and/or polyadenylation signals. Additionally, splice acceptor sequences may be included. Exemplary splice acceptor site sequences are known to those of skill in the art and include, by way of example only, CTGACCTCTTCTCTTCCTCCCACAG, (SEQ ID NO:1) (from the human HBB gene) and TTTCTCTCCACAG (SEQ ID NO:2) (from the human Immunoglobulin-gamma gene).

In certain embodiments, the exogenous sequence (donor) comprises a fusion of a protein of interest and, as its fusion partner, an extracellular domain of a membrane protein, causing the fusion protein to be located on the surface of the cell. This allows the protein encoded by the transgene to potentially act in the serum. In the case of treatment for an LSD, the enzyme encoded by the transgene fusion would be able to act on the metabolic products that are accumulating in the serum from its location on the surface of the cell (e.g., RBC). In addition, if the RBC is engulfed by a splenic macrophage as is the normal course of degradation, the lysosome formed when the macrophage engulfs the cell would expose the membrane bound fusion protein to the high concentrations of metabolic products in the lysosome at the pH more naturally favorable to that enzyme. Non-limiting examples of potential fusion partners are shown below in Table 1.

TABLE 1

Examples of potential fusion partners

| Name | Activity |
|---|---|
| Band 3 | Anion transporter, makes up to 25% of the RBC membrane surface protein |
| Aquaporin 1 | water transporter |
| Glut1 | glucose and L-dehydroascorbic acid transporter |
| Kidd antigen protein | urea transporter |
| RhAG | gas transporter |
| ATP1A1, ATP1B1 | Na+/K+-ATPase |
| ATP2B1, ATP2B2, ATP2B3, ATP2B4 | Ca2+-ATPase |
| NKCC1, NKCC2 | Na+ K+ 2Cl--cotransporter |
| SLC12A3 | Na+—Cl--cotransporter |
| SLC12A1, SLA12A2 | Na—K-cotransporter |

TABLE 1-continued

Examples of potential fusion partners

| Name | Activity |
|---|---|
| KCC1 | K—Cl cotransporter |
| KCNN4 | Gardos Channel |

Lysosomal storage diseases typically fall into five classes. These classes are shown below in Table 2 along with specific examples of the diseases. Thus, the donor molecules described herein can include sequences coding for one or more enzymes lacking or deficient in subjects with lysosomal storage diseases, including but not limited to the proteins shown in Table 2.

TABLE 2

Lysosomal Storage Diseases

| Protein | Disease | Disease Associated Gene | Accumulated product |
|---|---|---|---|
| 1. DEFECTS IN GLYCAN DEGRADATION | | | |
| I. Defects in glycoprotein degradation | | | |
| α-Sialidase (neuraminidase) | Sialidosis | NEU1 | sialidated glycopeptides and oligosaccharides |
| Cathepsin A | Galactosialidosis | CTSA | polysaccharide |
| lysosomal alpha-mannosidase | α-Mannosidosis | MAN2B1 | mannose-rich glycoproteins and oligosaccharides |
| lysosomal beta-mannosidase | β-Mannosidosis | MANBA | |
| Glycosylasparaginase | Aspartylglucosaminuria | AGA | glycoasparagines |
| Alpha L Fucosidase | Fucosidosis | FUCA1 | fucose |
| α-N-Acetylglucosaminidase | Sanfilippo syndrome B | NAGLU | glycosaminoglycan |
| II. Defects in glycolipid degradation | | | |
| A. GM1 Ganglioside | | | |
| β-Galactosidase | GM1 gangliosidosis/MPS IVB | GLB1 | keratan sulfate |
| β-Hexosaminidase α-subunit | GM2-gangliosidosis (Tay-Sachs) | HEXA | GM2 ganglioside |
| β-Hexosaminidase β-subunit | GM2-gangliosidosis (Sandhoff) | HEXB | GM2 ganglioside |
| GM2 activator protein | GM2 gangliosidosis | GM2A | GM2 ganglioside |
| Glucocerebrosidase | Gaucher disease | GBA | glucocerebroside |
| Saposin C | Gaucher disease (atypical) | PSAP | glucocerebroside |
| B. Defects in the degradation of sulfatide | | | |
| Arylsulfatase A | Metachromatic leukodystrophy | ARSA | sulphatide |
| Saposin B | Metachromatic leukodystrophy | PSAP | sulphatide |
| Formyl-Glycin generating enzyme | Multiple sulfatase deficiency | SUMF1 | sulfated lipids |
| β-Galactosylceramidase (Krabbe) | Globoid cell leukodystrophy | GALC | galactocerebroside |
| C. Defects in degradation of globotriaosylceramide | | | |
| α-Galactosidase A | Fabry | GLA | globotriaosylcera-mide |
| III. Defects in degradation of Glycosaminoglycan (Mucopolysaccharidoses) | | | |
| A. Degradation of heparan sulphate | | | |
| Iduronate sulfatase | MPS II (Hunter) | IDS | Dermatan sulfate, Heparan sulfate |
| Iduronidase | MPS 1 (Hurler, Scheie) | IDUA | Dermatan sulfate, Heparan sulfate |
| Heparan N-sulfatase | MPS IIIa (Sanfilippo A) | SGSH | Heparan sulfate |
| Acetyl-CoA transferase | MPS IIIc (Sanfilippo C) | HGSNAT | Heparan sulfate |
| N-acetyl glucosaminidase | MPS IIIb (Sanfilippo B) | NAGLU | Heparan sulfate |
| β-glucuronidase | MPS VII (Sly) | GUSB | |
| N-acetyl glucosamine 6-sulfatase | MPS IIId (Sanfilippo D) | GNS | Heparan sulfate |
| B. Degradation of other mucopolysaccharides | | | |
| B-Galactosidase | MPS VIB (Morquio B) | GLB1 | Keratan sulfate, |
| Galactose 6-sulfatase | MPS IVA (Morquio A) | GALNS | Keratan sulfate, Chondroitin 6-sulfate |
| Hyaluronidase | MPS IX | HYAL1 | Hyaluronic acid |
| C. Defects in degradation of glycogen | | | |
| α-Glucosidase | Pompe | GAA | Glycogen |

TABLE 2-continued

Lysosomal Storage Diseases

| Protein | Disease | Disease Associated Gene | Accumulated product |
|---|---|---|---|
| 2. DEFECTS IN LIPID DEGRADATION | | | |
| *I. Defects in degradation of sphingomyelin* | | | |
| Acid sphingomyelinase | Niemann Pick type A | SMPD1 | sphingomyelin |
| Acid ceramidase | Farber lipogranulomatosis | ASAH1 | nonsulfonated acid mucopolysaccharide |
| *II. Defects in degradation of triglycerides and cholesteryls ester* | | | |
| Acid lipase | Wolman and cholesteryl ester storage disease | LIPA | cholesteryl esters |
| 3. DEFECTS IN PROTEIN DEGRADATION | | | |
| Cathepsin K | Pycnodystostosis | CTSK | |
| Tripeptidyl peptidase | Ceroide lipofuscinosis | PPT2 | |
| Palmitoyl-protein thioesterase | Ceroide lipofuscinosis | PPT1 | |
| 4. DEFECTS IN LYSOSOMAL TRANSPORTERS | | | |
| Cystinosin (cystin transport) | Cystinosis | CTNS | |
| Sialin (sialic acid transport) | Salla disease | SLC17A5 | N-acetylneuraminic acid |
| 5. DEFECTS IN LYSOSOMAL TRAFFICKING PROTEINS | | | |
| Phosphotransferase γ-subunit | Mucolipidosis III (I-cell) | GNPTG | |
| Mucolipin-1(cation channel) | Mucolipidosis | MCOLN1 | |
| LYSOSOME-ASSOCIATED MEMBRANE PROTEIN 2 | Danon | LAMP2 | |
| Niemann-Pick disease, type C1 | Niemann Pick type C | NPC1 | LDL cholesterol |
| palmitoyl-protein thioesterase-1 | Ceroid lipofuscinosis (Batten Disease) | CLN3 | autofluorescent lipopigment storage material |
| neuronal ceroid lipofuscinosis-6 | Ceroid lipofuscinosis 6 | CLN 6 | |
| neuronal ceroid lipofuscinosis-8 | Ceroid lipofuscinosis 8 | CLN 8 | |
| LYSOSOMAL TRAFFICKING REGULATOR | Chediak-Higashi | LYST | |
| Myocilin | Griscelli Type 1 | MYOC | |
| RAS-associated protein 27A | Griscelli Type 2 | RAB27A | |
| Melanophilin | Griscelli Type 3 | MLPH or MYO5A | |
| AP3 β-subunit | Hermansky Pudliak | AP3B1 | ceroid |

In certain embodiments, the donor comprises a transgene that encodes a protein lacking of deficient in Hurler, Hunter and/or Gaucher LSDs, for example, iduronidase, iduronate-2-sulfatase and/or glucocerebrosidase. Following administration to the subject, for example to the liver via intravenous injection through the portal vein, the transgene is typically expressed at much higher levels in the liver and is detectable in secondary tissues including plasma than subjects not subject to nuclease-mediated integration. Levels of the therapeutic protein in the subject's tissues (e.g., plasma) are 2-4 fold (or any value therebetween), 2-10 fold (or any value therebetween), 10-100 fold (or any value therebetween) or more than in the untreated subjects.

In some cases, the donor may be an endogenous gene that has been modified. Although antibody response to enzyme replacement therapy varies with respect to the specific therapeutic enzyme in question and with the individual patient, a significant immune response has been seen in many LSD patients being treated with enzyme replacement. In addition, the relevance of these antibodies to the efficacy of treatment is also variable (see Katherine Ponder, (2008) *J Clin Invest* 118(8):2686). Thus, the methods and compositions of the current invention can comprise the use of donor molecules whose sequence has been altered by functionally silent amino acid changes at sites known to be priming epitopes for endogenous immune responses, such that the polypeptide produced by such a donor is less immunogenic.

LSD patients often have neurological sequelae due the lack of the missing enzyme in the brain. Unfortunately, it is often difficult to deliver therapeutics to the brain via the blood due to the impermeability of the blood brain barrier. Thus, the methods and compositions of the invention may be used in conjunction with methods to increase the delivery of the therapeutic into the brain. There are some methods that cause a transient opening of the tight junctions between cells of the brain capillaries. Examples include transient osmotic disruption through the use of an intracarotid administration of a hypertonic mannitol solution, the use of focused ultrasound and the administration of a bradykinin analogue. Alternatively, therapeutics can be designed to utilize receptors or transport mechanisms for specific transport into the brain. Examples of specific receptors that may be used include the transferrin receptor, the insulin receptor or the low-density lipoprotein receptor related proteins 1 and 2 (LRP-1 and LRP-2). LRP is known to interact with a range of secreted proteins such as apoE, tPA, PAI-1 etc, and so fusing a recognition sequence from one of these proteins for LRP may facilitate transport of the enzyme into the brain, following expression in the liver of the therapeutic protein and secretion into the blood stream (see Gabathuler, (2010) ibid). The transgenes carried on the donor sequences described herein may be isolated from plasmids, cells or other sources using standard techniques known in the art such as PCR. Donors for use can include varying types of topology, including circular supercoiled, circular relaxed, linear and the like. Alternatively, they may be chemically synthesized using standard oligonucleotide synthesis techniques. In addition, donors may be methylated or lack methylation. Donors may be in the form of bacterial or yeast artificial chromosomes (BACs or YACs).

The double-stranded donor polynucleotides described herein may include one or more non-natural bases and/or backbones. In particular, insertion of a donor molecule with methylated cytosines may be carried out using the methods described herein to achieve a state of transcriptional quiescence in a region of interest.

In certain embodiments, the exogenous sequences can comprise a marker gene (described above), allowing selection of cells that have undergone targeted integration, and a linked sequence encoding an additional functionality. Non-limiting examples of marker genes include GFP, drug selection marker(s) and the like.

Construction of such expression cassettes, following the teachings of the present specification, utilizes methodologies well known in the art of molecular biology (see, for example, Ausubel or Maniatis). Before use of the expression cassette to generate a transgenic animal, the responsiveness of the expression cassette to the stress-inducer associated with selected control elements can be tested by introducing the expression cassette into a suitable cell line (e.g., primary cells, transformed cells, or immortalized cell lines).

Targeted insertion of non-coding nucleic acid sequence may also be achieved. Sequences encoding antisense RNAs, RNAi, shRNAs and micro RNAs (miRNAs) may also be used for targeted insertions.

In additional embodiments, the donor nucleic acid may comprise non-coding sequences that are specific target sites for additional nuclease designs. Subsequently, additional nucleases may be expressed in cells such that the original donor molecule is cleaved and modified by insertion of another donor molecule of interest. In this way, reiterative integrations of donor molecules may be generated allowing for trait stacking at a particular locus of interest or at a safe harbor locus.

Cells

Also provided herein are genetically modified cells, for example, liver cells or stem cells comprising a transgene encoding a protein lacking or deficient in a lysosomal storage disease, including cells produced by the methods described herein. The transgene is integrated in a targeted manner into the cell's genome using one or more nucleases. Unlike random integration, targeted integration ensures that the transgene is integrated into a specified gene. The transgene may be integrated anywhere in the target gene. In certain embodiments, the transgene is integrated at or near the nuclease binding and/or cleavage site, for example, within 1-300 (or any number of base pairs therebetween) base pairs upstream or downstream of the site of cleavage and/or binding site, more preferably within 1-100 base pairs (or any number of base pairs therebetween) of either side of the cleavage and/or binding site, even more preferably within 1 to 50 base pairs (or any number of base pairs therebetween) of either side of the cleavage and/or binding site. In certain embodiments, the integrated sequence does not include any vector sequences (e.g., viral vector sequences). In certain embodiments, the cells comprise a modification (e.g., insertion and/or deletion) made by a nuclease as described herein such that the modification is within an intron of an HPRT gene, for example intron 1. In certain embodiments, the modification is at or near (e.g., 1-300 base pairs or any number of base pairs therebetween) SEQ ID NO:24 or 25. In other embodiments, the modification is 1-100 (or any number of base pairs therebetween) base pairs of SEQ ID NO:24 or 25. In certain embodiments, the modification is within SEQ ID NO:24 and/or SEQ ID NO:25, for example a modification of 1 or more base pairs in either SEQ ID NO:24 or 25.

Any cell type can be genetically modified as described herein to comprise a transgene, including but not limited to cells or cell lines. Other non-limiting examples of genetically modified cells as described herein include T-cells (e.g., CD4+, CD3+, CD8+, etc.); dendritic cells; B-cells; autologous (e.g., patient-derived). In certain embodiments, the cells are liver cells and are modified in vivo. In certain embodiments, the cells are stem cells, including heterologous pluripotent, totipotent or multipotent stem cells (e.g., CD34+ cells, induced pluripotent stem cells (iPSCs), embryonic stem cells or the like). In certain embodiments, the cells as described herein are stem cells derived from patient.

The cells as described herein are useful in treating and/or preventing lysosomal storage disorders in a subject with the disorder, for example, by in vivo therapies. Ex vivo therapies are also provided, for example when the nuclease-modified cells can be expanded and then reintroduced into the patient using standard techniques. See, e.g., Tebas et al (2014) *New Eng J Med* 370(10):901. In the case of stem cells, after infusion into the subject, in vivo differentiation of these precursors into cells expressing the functional protein (from the inserted donor) also occurs.

Pharmaceutical compositions comprising the cells as described herein are also provided. In addition, the cells may be cryopreserved prior to administration to a patient.

Delivery

The nucleases, polynucleotides encoding these nucleases, donor polynucleotides and compositions comprising the proteins and/or polynucleotides described herein may be delivered in vivo or ex vivo by any suitable means into any cell type.

Thus, the instant disclosure includes in vivo or ex vivo treatment of diseases and conditions that are amenable to insertion of a transgenes encoding a therapeutic protein, for example treatment of LSD(s) via nuclease-mediated integration of proteins (enzymes) lacking of deficient in the LSD(s). The compositions are administered to a human patient in an amount effective to obtain the desired concentration of the therapeutic polypeptide in the serum or the target organ or cells. Administration can be by any means in which the polynucleotides are delivered to the desired target cells. For example, both in vivo and ex vivo methods are contemplated. Intravenous injection to the portal vein is a preferred method of administration. Other in vivo administration modes include, for example, direct injection into the lobes of the liver or the biliary duct and intravenous injection distal to the liver, including through the hepatic artery, direct injection in to the liver parenchyma, injection via the hepatic artery, and/or retrograde injection through the biliary tree. Ex vivo modes of administration include transduction in vitro of resected hepatocytes or other cells of the liver, followed by infusion of the transduced, resected hepatocytes back into the portal vasculature, liver parenchyma or biliary tree of the human patient, see e.g., Grossman et al., (1994) *Nature Genetics*, 6:335-341.

Methods of delivering nucleases and/or donors as described herein are described, for example, in U.S. Pat. Nos. 6,453,242; 6,503,717; 6,534,261; 6,599,692; 6,607,882; 6,689,558; 6,824,978; 6,933,113; 6,979,539; 7,013,219; and 7,163,824, the disclosures of all of which are incorporated by reference herein in their entireties.

Nucleases and/or donor constructs as described herein may also be delivered using vectors containing sequences encoding one or more of the ZFN(s), TALEN(s), CRIPSR/Cas systems or Ttago systems. Any vector systems may be used including, but not limited to, plasmid vectors, retroviral vectors, lentiviral vectors, adenovirus vectors, poxvirus vectors; herpesvirus vectors and adeno-associated virus (AAV) vectors, etc. See, also, U.S. Pat. Nos. 6,534,261; 6,607,882; 6,824,978; 6,933,113; 6,979,539; 7,013,219; and 7,163,824, incorporated by reference herein in their entireties. Furthermore, it will be apparent that any of these vectors may comprise one or more of the sequences needed for treatment. Thus, when one or more nucleases and a donor construct are introduced into the cell, the nucleases and/or donor polynucleotide may be carried on the same vector or on different vectors (DNA MC(s)). When multiple vectors are used, each vector may comprise a sequence encoding one or multiple nucleases and/or donor constructs.

Conventional viral and non-viral based gene transfer methods can be used to introduce nucleic acids encoding nucleases and donor constructs in cells (e.g., mammalian cells) and target tissues. Non-viral vector delivery systems include DNA or RNA plasmids, DNA MCs, naked nucleic acid, and nucleic acid complexed with a delivery vehicle such as a liposome, other nanoparticle or poloxamer. Viral vector delivery systems include DNA and RNA viruses, which have either episomal or integrated genomes after delivery to the cell. For a review of in vivo delivery of engineered DNA-binding proteins and fusion proteins comprising these binding proteins, see, e.g., Rebar (2004) *Expert Opinion Invest. Drugs* 13(7):829-839; Rossi et al. (2007) *Nature Biotech.* 25(12):1444-1454 as well as general gene delivery references such as Anderson, *Science* 256:808-813 (1992); Nabel & Feigner, *TIBTECH* 11:211-217 (1993); Mitani & Caskey, *TIBTECH* 11:162-166 (1993); Dillon, *TIBTECH* 11:167-175 (1993); Miller, *Nature* 357:455-460 (1992); Van Brunt, *Biotechnology* 6(10):1149-1154 (1988); Vigne, *Restorative Neurology and Neuroscience* 8:35-36 (1995); Kremer & Perricaudet, *British Medical Bulletin* 51(1):31-44 (1995); Haddada et al., in *Current Topics in Microbiology and Immunology* Doerfler and Böhm (eds.) (1995); and Yu et al., *Gene Therapy* 1:13-26 (1994).

Methods of non-viral delivery of nucleic acids include electroporation, lipofection, microinjection, biolistics, virosomes, liposomes, immunoliposomes, polycation or lipid:nucleic acid conjugates, nanoparticles, naked DNA, artificial virions, and agent-enhanced uptake of DNA. Sonoporation using, e.g., the Sonitron 2000 system (Rich-Mar) can also be used for delivery of nucleic acids.

Additional exemplary nucleic acid delivery systems include those provided by AmaxaBiosystems (Cologne, Germany), Maxcyte, Inc. (Rockville, Md.), BTX Molecular Delivery Systems (Holliston, Mass.) and Copernicus Therapeutics Inc, (see for example U.S. Pat. No. 6,008,336). Lipofection is described in e.g., U.S. Pat. Nos. 5,049,386; 4,946,787; and 4,897,355) and lipofection reagents are sold commercially (e.g., Transfectam™ and Lipofectin™). Cationic and neutral lipids that are suitable for efficient receptor-recognition lipofection of polynucleotides include those of Feigner, WO 91/17424, WO 91/16024.

The preparation of lipid:nucleic acid complexes, including targeted liposomes such as immunolipid complexes, is well known to one of skill in the art (see, e.g., Crystal, *Science* 270:404-410 (1995); Blaese et al., *Cancer Gene Ther.* 2:291-297 (1995); Behr et al., *Bioconjugate Chem.* 5:382-389 (1994); Remy et al., *Bioconjugate Chem.* 5:647-654 (1994); Gao et al., *Gene Therapy* 2:710-722 (1995); Ahmad et al., *Cancer Res.* 52:4817-4820 (1992); U.S. Pat. Nos. 4,186,183, 4,217,344, 4,235,871, 4,261,975, 4,485,054, 4,501,728, 4,774,085, 4,837,028, and 4,946,787).

Additional methods of delivery include the use of packaging the nucleic acids to be delivered into EnGeneIC delivery vehicles (EDVs). These EDVs are specifically delivered to target tissues using bispecific antibodies where one arm of the antibody has specificity for the target tissue and the other has specificity for the EDV. The antibody brings the EDVs to the target cell surface and then the EDV is brought into the cell by endocytosis. Once in the cell, the contents are released (see MacDiarmid et al (2009) *Nature Biotechnology* 27(7):643).

The use of RNA or DNA viral based systems for the delivery of nucleic acids encoding engineered ZFPs, TALEs and/or CRISPR/Cas or TtAgo systems take advantage of highly evolved processes for targeting a virus to specific cells in the body and trafficking the viral payload to the nucleus. Viral vectors can be administered directly to patients (in vivo) or they can be used to treat cells in vitro and the modified cells are administered to patients (ex vivo). Conventional viral based systems for the delivery of ZFPs include, but are not limited to, retroviral, lentivirus, adenoviral, adeno-associated, vaccinia and herpes simplex virus vectors for gene transfer. Integration in the host genome is possible with the retrovirus, lentivirus, and adeno-associated virus gene transfer methods, often resulting in long term expression of the inserted transgene. Additionally, high transduction efficiencies have been observed in many different cell types and target tissues.

The tropism of a retrovirus can be altered by incorporating foreign envelope proteins, expanding the potential target population of target cells. Lentiviral vectors are retroviral vectors that are able to transduce or infect non-dividing cells and typically produce high viral titers. Selection of a retroviral gene transfer system depends on the target tissue. Retroviral vectors are comprised of cis-acting long terminal repeats with packaging capacity for up to 6-10 kb of foreign sequence. The minimum cis-acting LTRs are sufficient for replication and packaging of the vectors, which are then used to integrate the therapeutic gene into the target cell to provide permanent transgene expression. Widely used retroviral vectors include those based upon murine leukemia virus (MuLV), gibbon ape leukemia virus (GaLV), Simian Immunodeficiency virus (SIV), human immunodeficiency virus (HIV), and combinations thereof (see, e.g., Buchscher et al., *J. Virol.* 66:2731-2739 (1992); Johann et al., *J. Virol.* 66:1635-1640 (1992); Sommerfelt et al., *Virol.* 176:58-59 (1990); Wilson et al., *J. Virol.* 63:2374-2378 (1989); Miller et al., *J. Virol.* 65:2220-2224 (1991); PCT/US94/05700).

In applications in which transient expression is preferred, adenoviral based systems can be used. Adenoviral based vectors are capable of very high transduction efficiency in many cell types and do not require cell division. With such vectors, high titer and high levels of expression have been obtained. This vector can be produced in large quantities in a relatively simple system. Adeno-associated virus ("AAV") vectors are also used to transduce cells with target nucleic acids, e.g., in the in vitro production of nucleic acids and peptides, and for in vivo and ex vivo gene therapy procedures (see, e.g., West et al., *Virology* 160:38-47 (1987); U.S. Pat. No. 4,797,368; WO 93/24641; Kotin, *Human Gene Therapy* 5:793-801 (1994); Muzyczka, *J. Clin. Invest.* 94:1351 (1994). Construction of recombinant AAV vectors are described in a number of publications, including U.S. Pat. No. 5,173,414; Tratschin et al., *Mol. Cell. Biol.* 5:3251-3260 (1985); Tratschin, et al., *Mol. Cell. Biol.* 4:2072-2081 (1984); Hermonat & Muzyczka, *PNAS* 81:6466-6470 (1984); and Samulski et al., *J. Virol.* 63:03822-3828 (1989).

At least six viral vector approaches are currently available for gene transfer in clinical trials, which utilize approaches that involve complementation of defective vectors by genes inserted into helper cell lines to generate the transducing agent.

pLASN and MFG-S are examples of retroviral vectors that have been used in clinical trials (Dunbar et al., *Blood* 85:3048-305 (1995); Kohn et al., *Nat. Med.* 1:1017-102 (1995); Malech et al., *PNAS* 94:22 12133-12138 (1997)). PA317/pLASN was the first therapeutic vector used in a gene therapy trial. (Blaese et al., *Science* 270:475-480 (1995)). Transduction efficiencies of 50% or greater have been observed for MFG-S packaged vectors. (Ellem et al., *Immunol Immunother.* 44(1):10-20 (1997); Dranoff et al., *Hum. Gene Ther.* 1:111-2 (1997).

Recombinant adeno-associated virus vectors (rAAV) are a promising alternative gene delivery systems based on the defective and nonpathogenic parvovirus adeno-associated type 2 virus. All vectors are derived from a plasmid that retains only the AAV 145 bp inverted terminal repeats flanking the transgene expression cassette. Efficient gene transfer and stable transgene delivery due to integration into the genomes of the transduced cell are key features for this vector system. (Wagner et al., *Lancet* 351:9117 1702-3 (1998), Kearns et al., *Gene Ther.* 9:748-55 (1996)). Other AAV serotypes, including AAV1, AAV2, AAV3, AAV4, AAV5, AAV6, AAV7, AAV8, AAV9 and AAVrh.10 and any novel AAV serotype can also be used in accordance with the present invention. In some embodiments, mixed AAV serotypes are used (e.g. comprising ITR sequence from one AAV and capsid sequences from another). Examples of these mixed AAVs include AAV2/5, AAV2/6 and AAV2/8.

Replication-deficient recombinant adenoviral vectors (Ad) can be produced at high titer and readily infect a number of different cell types. Most adenovirus vectors are engineered such that a transgene replaces the Ad E1a, E1b, and/or E3 genes; subsequently the replication defective vector is propagated in human 293 cells that supply deleted gene function in trans. Ad vectors can transduce multiple types of tissues in vivo, including nondividing, differentiated cells such as those found in liver, kidney and muscle. Conventional Ad vectors have a large carrying capacity. An example of the use of an Ad vector in a clinical trial involved polynucleotide therapy for antitumor immunization with intramuscular injection (Sterman et al., *Hum. Gene Ther.* 7:1083-9 (1998)). Additional examples of the use of adenovirus vectors for gene transfer in clinical trials include Rosenecker et al., *Infection* 24:1 5-10 (1996); Sterman et al., *Hum. Gene Ther.* 9:7 1083-1089 (1998); Welsh et al., *Hum. Gene Ther.* 2:205-18 (1995); Alvarez et al., *Hum. Gene Ther.* 5:597-613 (1997); Topf et al., *Gene Ther.* 5:507-513 (1998); Sterman et al., *Hum. Gene Ther.* 7:1083-1089 (1998).

Packaging cells are used to form virus particles that are capable of infecting a host cell. Such cells include 293 cells, which package adenovirus, and ψ2 cells or PA317 cells, which package retrovirus. Virus particles can also be made in insect cell systems using a baculovirus. Viral vectors used in gene therapy are usually generated by a producer cell line that packages a nucleic acid vector into a viral particle. The vectors typically contain the minimal viral sequences required for packaging and subsequent integration into a host (if applicable), other viral sequences being replaced by an expression cassette encoding the protein to be expressed. The missing viral functions are supplied in trans by the packaging cell line. For example, AAV vectors used in gene therapy typically only possess inverted terminal repeat (ITR) sequences from the AAV genome which are required for packaging and integration into the host genome. Viral DNA is packaged in a cell line, which contains a helper plasmid encoding the other AAV genes, namely rep and cap, but lacking ITR sequences. The cell line is also infected with adenovirus as a helper. The helper virus promotes replication of the AAV vector and expression of AAV genes from the helper plasmid. The helper plasmid is not packaged in significant amounts due to a lack of ITR sequences. Contamination with adenovirus can be reduced by, e.g., heat treatment to which adenovirus is more sensitive than AAV.

In many gene therapy applications, it is desirable that the gene therapy vector be delivered with a high degree of specificity to a particular tissue type. Accordingly, a viral vector can be modified to have specificity for a given cell type by expressing a ligand as a fusion protein with a viral coat protein on the outer surface of the virus. The ligand is chosen to have affinity for a receptor known to be present on the cell type of interest. For example, Han et al., *Proc. Natl. Acad. Sci. USA* 92:9747-9751 (1995), reported that Moloney murine leukemia virus can be modified to express human heregulin fused to gp70, and the recombinant virus infects certain human breast cancer cells expressing human epidermal growth factor receptor. This principle can be extended to other virus-target cell pairs, in which the target cell expresses a receptor and the virus expresses a fusion protein comprising a ligand for the cell-surface receptor. For example, filamentous phage can be engineered to display antibody fragments (e.g., FAB or Fv) having specific binding affinity for virtually any chosen cellular receptor. Although the above description applies primarily to viral vectors, the same principles can be applied to nonviral vectors. Such vectors can be engineered to contain specific uptake sequences which favor uptake by specific target cells.

Gene therapy vectors can be delivered in vivo by administration to an individual patient, typically by systemic administration (e.g., intravenous, intraperitoneal, intramuscular, subdermal, or intracranial infusion) or topical application, as described below. Alternatively, vectors can be delivered to cells ex vivo, such as cells explanted from an individual patient (e.g., lymphocytes, bone marrow aspirates, tissue biopsy) or universal donor hematopoietic stem cells, followed by reimplantation of the cells into a patient, usually after selection for cells which have incorporated the vector.

Vectors (e.g., retroviruses, adenoviruses, liposomes, etc.) containing nucleases and/or donor constructs can also be administered directly to an organism for transduction of cells in vivo. Alternatively, naked DNA can be administered. Administration is by any of the routes normally used for introducing a molecule into ultimate contact with blood or tissue cells including, but not limited to, injection, infusion, topical application and electroporation. Suitable methods of administering such nucleic acids are available and well known to those of skill in the art, and, although more than one route can be used to administer a particular composition, a particular route can often provide a more immediate and more effective reaction than another route.

Vectors suitable for introduction of polynucleotides (e.g. nuclease-encoding and/or double-stranded donors) described herein include non-integrating lentivirus vectors (IDLV). See, for example, Ory et al. (1996) Proc. Natl. Acad. Sci. USA 93:11382-11388; Dull et al. (1998) J. Virol. 72:8463-8471; Zuffery et al. (1998) J. Virol. 72:9873-9880; Follenzi et al. (2000) Nature Genetics 25:217-222; U.S. Pat. No. 8,936,936.

Pharmaceutically acceptable carriers are determined in part by the particular composition being administered, as well as by the particular method used to administer the composition. Accordingly, there is a wide variety of suitable formulations of pharmaceutical compositions available, as described below (see, e.g., *Remington's Pharmaceutical Sciences,* 17th ed., 1989).

It will be apparent that the nuclease-encoding sequences and donor constructs can be delivered using the same or different systems. For example, the nucleases and donors can be carried by the same DNA MC. Alternatively, a donor polynucleotide can be carried by a MC, while the one or more nucleases can be carried by a standard plasmid or AAV vector. Furthermore, the different vectors can be administered by the same or different routes (intramuscular injection, tail vein injection, other intravenous injection, intraperitoneal administration and/or intramuscular injection. The vectors can be delivered simultaneously or in any sequential order.

The effective amount of nuclease(s) and donor to be administered will vary from patient to patient and according to the therapeutic polypeptide of interest. Accordingly, effective amounts are best determined by the physician administering the compositions and appropriate dosages can be determined readily by one of ordinary skill in the art. After allowing sufficient time for integration and expression (typically 4-15 days, for example), analysis of the serum or other tissue levels of the therapeutic polypeptide and comparison to the initial level prior to administration will determine whether the amount being administered is too low, within the right range or too high. Suitable regimes for initial and subsequent administrations are also variable, but are typified by an initial administration followed by subsequent administrations if necessary. Subsequent administrations may be administered at variable intervals, ranging from daily to annually to every several years. One of skill in the art will appreciate that appropriate immunosuppressive techniques may be recommended to avoid inhibition or blockage of transduction by immunosuppression of the delivery vectors, see e.g., Vilquin et al., (1995) *Human Gene Ther.,* 6:1391-1401.

Formulations for both ex vivo and in vivo administrations include suspensions in liquid or emulsified liquids. The active ingredients often are mixed with excipients which are pharmaceutically acceptable and compatible with the active ingredient. Suitable excipients include, for example, water, saline, dextrose, glycerol, ethanol or the like, and combinations thereof. In addition, the composition may contain minor amounts of auxiliary substances, such as, wetting or emulsifying agents, pH buffering agents, stabilizing agents or other reagents that enhance the effectiveness of the pharmaceutical composition.

Applications

The methods of this invention contemplate the provision of high levels of one or more proteins lacking in one or more LSDs in all tissues of a subject, including blood, following nuclease-mediated integration of a sequence encoding the one or more proteins into an endogenous locus (e.g., albumin in liver cells or HPRT) of the subject. Thus, also contemplated treatment of a monogenic disease (e.g. lysosomal storage disease). Treatment can comprise insertion of the corrected disease associated gene in safe harbor locus (e.g. albumin or HPRT) for expression of the needed enzyme and release into the blood stream. Insertion into a secretory cell, such as a liver cell for release of the product into the blood stream, is particularly useful and surprisingly is shown herein to increase circulating levels of the protein in the subject to levels by 4 to 100 fold (as compared to untreated subjects).

Thus, this technology may be of use in a condition where a patient is deficient in some protein due to problems (e.g., problems in expression level or problems with the protein expressed as sub- or non-functioning). Particularly useful with this invention is the expression of transgenes to correct or restore functionality in lysosomal storage disorders.

The following Examples relate to exemplary embodiments of the present disclosure in which the nuclease comprises a zinc finger nuclease (ZFN) or TALEN. It will be appreciated that this is for purposes of exemplification only and that other nucleases or nuclease systems can be used, for instance homing endonucleases (meganucleases) with engineered DNA-binding domains and/or fusions of naturally occurring engineered homing endonucleases (meganucleases) DNA-binding domains and heterologous cleavage domains and/or a CRISPR/Cas or TtAgo systems optionally comprising an engineered single guide RNA and at least one nuclease.

EXAMPLES

Example 1: Design, Construction and General Characterization of Albumin-Specific Nucleases Nucleases (e.g., ZFNs, TALENs, CRISPR/Cas) targeted to albumin are described in U.S. Patent Publication Nos. 20130177983; 20130177960 and 20150056705). For these experiments, ZFNs comprising the ZFPs (operably linked to the engineered cleavage domains) were used to introduce donors comprising sequences encoding proteins lacking in LSDs to mice and are shown below in Tables 3 and 4.

TABLE 3

Mouse Albumin Designs

| SBS # | F1 | F2 | F3 | F4 | F5 |
|---|---|---|---|---|---|
| 31523 | RSDNLSE (SEQ ID NO: 3) | QSGNLAR (SEQ ID NO: 4) | DRSNLSR (SEQ ID NO: 5) | WRSSLRA (SEQ ID NO: 6) | DSSDRKK (SEQ ID NO: 7) |
| 48641 | TSGSLTR (SEQ ID NO: 8) | RSDALST (SEQ ID NO: 9) | QSATRTK (SEQ ID NO: 10) | LRHHLTR (SEQ ID NO: 11) | QAGQRRV (SEQ ID NO: 12) |

TABLE 4

Target Sites of mouse albumin-specific zinc fingers

| SBS # | Target site |
|---|---|
| 31523 | ttTCCTGTAACGATCGGgaactggcatc (SEQ ID NO: 13) |

TABLE 4-continued

Target Sites of mouse
albumin-specific zinc fingers

| SBS # | Target site |
|---|---|
| 48641 | ctGAAGGTgGCAATGGTTcctctctgct (SEQ ID NO: 14) |

Figure 1:
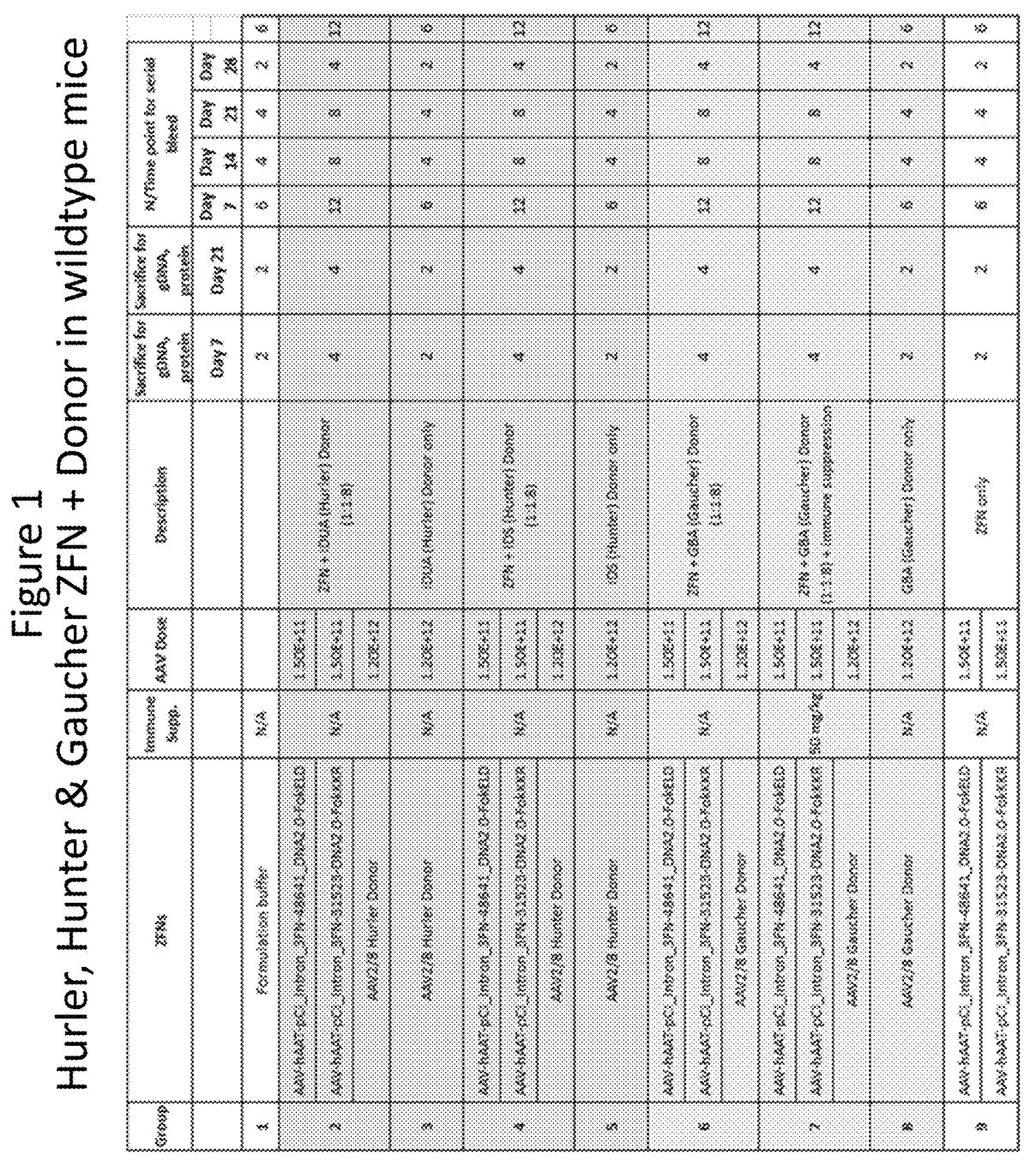

In particular, ZFNs targeted to mouse albumin were used with AAV (e.g., AAV2) donors in the combinations and dosages shown in FIG. 1. AAV donors included homology arms to the mouse albumin locus. Donors without homology arms may be also be used. See, e.g., U.S. Publication Nos. 20110207221. The donors encoded iduronidase (Hurler), iduronate-2-sulfatase (Hunter) or glucocerebrosidase (Gaucher) and were expressed from the endogenous albumin promoter.

ZFNs and donor comprising AAV were administered to the liver of the subjects via intravenous injection through the tail vein of the animal. In each case, the ZFN pairs used were an ELD/KKR pair. AAV dose used is shown in FIG. 1 which also indicates the ratio of the AAVs comprising the ZFNs with the AAVs comprising the donor DNAs. FIG. 1 also shows the number of animals used, the group types of animals used, and the days when the animals were tested. In some experiments, the animals were additionally subject to an immunosuppression ("+IS") regime. In these animals, cyclophosphamide was administered at a dose of 50 mg/kg by intraperitoneal (IP) injection at days 0 and 14. Expression of the proteins encoded by the transgenes was evaluated using standard techniques, namely by Western blotting in the liver and by plasma enzymatic activity assays that measure the levels of activity of the expressed protein in the mouse plasma.

The enzymatic assays used were fluorescence based assays performed by incubating tissue lysate or plasma with the appropriate substrates which, upon reaction with the active therapeutic protein, produce a fluorescent product which can be measured by standard protocols. The substrates used were the following: for testing the presence of active IDUA, 4-Methylumbelliferyl alpha-L-iduronide (from Santa Cruz Biotechnology) was used; for active IDS, 4-Methylumbelliferyl α-L-Idopyranosiduronic Acid 2-Sulfate Disodium Salt (from Santa Cruz Biotechnology) was used; for active GBA, 4-methylumbelliferyl β-D-glucopyranoside (Sigma-Aldrich). For production of a standard curve, 4-methylumbelliferone (from Sigma-Aldrich) was used.

The Western blots were done using standard methods known in the art. For the assay of IDUA protein, an antibody purchased from R&D Systems was used, while for the assay of the IDS protein, a different antibody purchased from R&D Systems was used.

Figure 4:
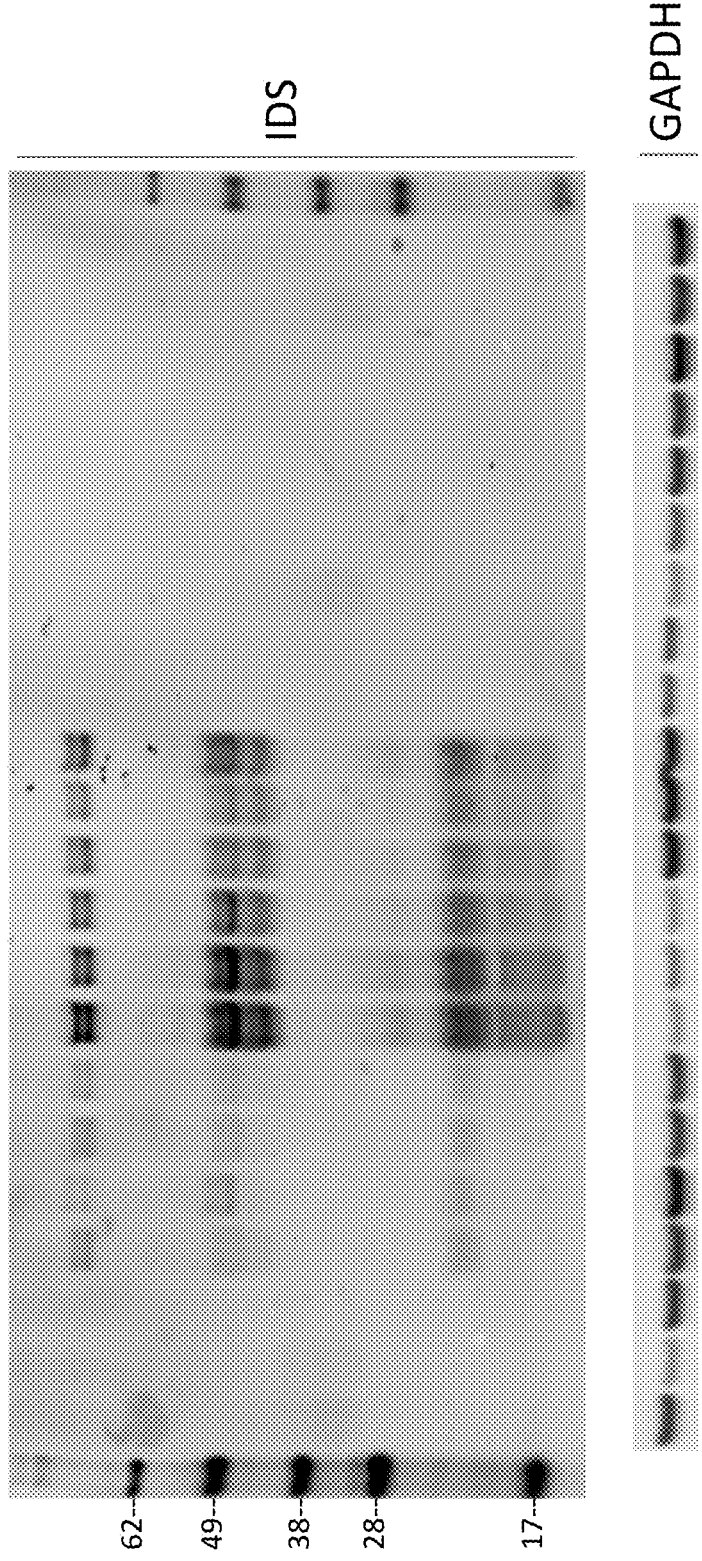
FIG. 4 depicts Western blot results of iduronate-2-sulfatase expression in liver cells of the indicated animals (controls, donor+ZFNs, donor only and ZFN only), labeled as described for FIG. 2. A loading control ("GADPH") is shown at the bottom of the figure.

As shown in FIGS. 2 and 3, animals receiving both ZFN and the iduronidase donor exhibited increased expression and activity as compared to subject not receiving donor and ZFN. Likewise, as shown in FIGS. 4 and 5, animals receiving both ZFN and the iduronate-2-sulfatase donor exhibited increased expression and activity as compared to subject not receiving donor and ZFN. As shown in FIG. 6, animals receiving both ZFN and the glucocererosidase donor exhibited increased activity as compared to subject not receiving donor and ZFN.

Thus, nuclease-mediated integration into liver of a transgene encoding a protein lacking or deficient in an LSD significantly increases (2-100 fold or more) the levels and activity of the protein in secondary tissues outside the liver, including in circulating blood.

Example 2: Selection of Cells Comprising an Integrated IDS Transgene Using HPRT

Nucleases (e.g., ZFNs, TALENs, CRISPR/Cas) targeted to HPRT are described in U.S. Pat. No. 8,895,264 and U.S. Patent Publication No. 20130137104. For these experiments, ZFNs comprising the ZFPs (operably linked to the engineered cleavage domains) were used to introduce donors comprising sequences encoding proteins lacking in LSDs to the HPRT locus in K562 cells and human CD34+ HSC. Specifically, the nuclease pair listed below in Tables 5 and 6 was used to introduce the IDS transgene.

TABLE 5 human HPRT designs

| Target species/ SBS # | F1 | F2 | F3 | F4 | F5 | F6 |
|---|---|---|---|---|---|---|
| Human 34306 | TSGSLSR (SEQ ID NO: 15) | QSGNLAR (SEQ ID NO: 4) | QSSDLSR (SEQ ID NO: 16) | RSDHLSQ (SEQ ID NO: 17) | DNSNRIN (SEQ ID NO: 18) | NA |
| Human 34303 | QSGDLTR (SEQ ID NO: 19) | TSGSLTR (SEQ ID NO: 8) | RSDVLSE (SEQ ID NO: 20) | RNQHRKT (SEQ ID NO: 21) | RSAHLSR (SEQ ID NO: 22) | DRSDLSR (SEQ ID NO: 23) |

TABLE 6

Target Sites of human HPRT-specific zinc fingers

| SBS # | Target site |
|---|---|
| 34306 | tgCACAGGgGCTGAAGTTgtcccacagg (SEQ ID NO: 24) |
| 34303 | tgGCCAGGAGGCTGGTTGCAaacattt (SEQ ID NO: 25) |

Figure 7:
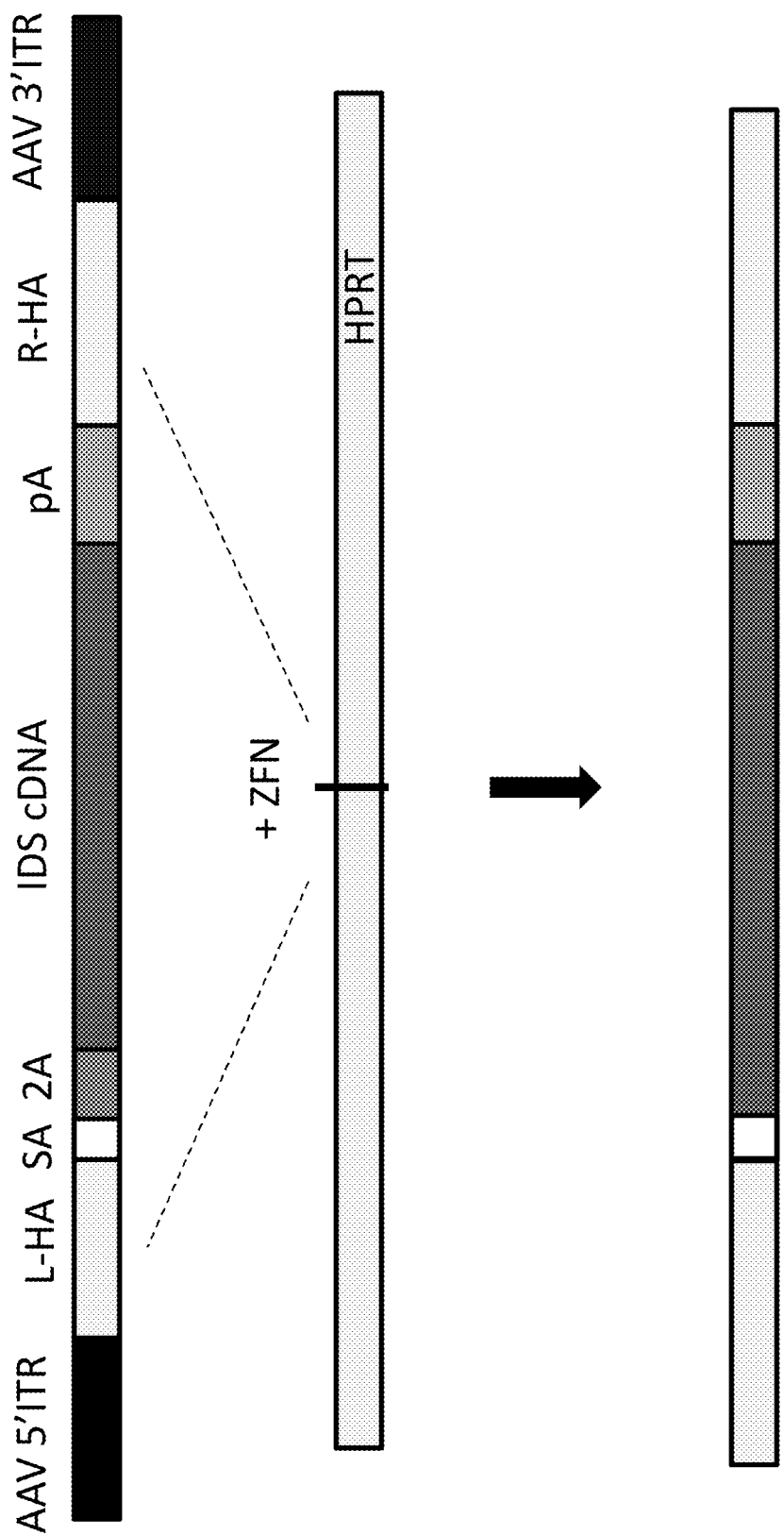
FIG. 7 is an illustration of the iduronate sulfatase (IDS) cDNA transgene donor and its integration into the endogenous HPRT locus. The donor construct is shown across the top and comprises AAV6 LTR sequences ("AAV"), the right and left homology arms, homologous to the endogenous HPRT gene, that flank the IDS transgene ("R-HA" for right homology arm and "L-HA" for left homology arm), a splice acceptor site ("SA"), a 2A self-cleaving peptide sequence ("2A"), and the IDS cDNA transgene ("IDS cDNA"). The middle line shows the endogenous HPRT for integration of the donor transgene, and bottom line shows an illustration of the integrated IDS cDNA transgene into the endogenous HPRT gene.

For these experiments, the IDS cDNA donor was delivered via an AAV2/6 particle, and the IDS cDNA transgene comprised homology arms for the HPRT regions flanking the cut site (see FIG. 7). The homology arms were approximately and the IDS encoding transgene was approximately 1652 base pairs.

To integrate the IDS cDNA transgene and assay its expression, HPRT specific zinc finger nucleases in the form of mRNA were transfected into human peripheral blood mobilized hematopoietic stem cells (CD34+ cells, from a male donor, i.e. these cells only had one copy of the HPRT gene per cell) or K562 cells. Briefly, 200,000 cells were transfected by BTX nucleofection by standard methods. The concentrations of nucleases were 40 µg/mL mRNA each per nucleofection. An AAV6 transgene donor was delivered 16 hours prior to transfection at an MOI of 1e4 viral genomes/cell. 24 hours after transfection the cells were then cultured in erythroid differentiation medium (EDM) on the basis of IMDM supplemented with stabilized glutamine, 330 µg/mL holo-human transferrin, 10 µg/mL recombinant human insulin, 2 IU/mL heparin, and 5% human plasma. The expansion procedure comprised 3 steps. In the first step (day 0 to day 7), $10^4$ cells/mL CD34+ cells were cultured in EDM in the presence of 10 µM hydrocortisone, 100 ng/mL SCF, 5 ng/mL IL-3, and 3 IU/mL Epo. On day 4, 1 volume of cell culture was diluted in 4 volumes of fresh medium containing SCF, IL-3, Epo, and hydrocortisone. 100 nM 6-TG was added to wells at this stage. In the second step (day 7 to day 11), the cells were resuspended at $10^5$ cells/mL in EDM supplemented with SCF and Epo. In the third step (day 11 to day 18), the cells were cultured in EDM supplemented with Epo alone. At day 11, 6-TG concentration was increased to 300 nM. Cell counts were adjusted to $7.5 \times 10^5$ to $1 \times 10^6$ and $5\text{-}10 \times 10^6$ cells/mL on days 11 and 15, respectively. On day 13, 6-TG concentration was increased to 2 µM. Cells were harvested for protein lysate and genomic DNA at day 18 (19 days post transfection). Supernatant was also collected for IDS enzymatic activity analysis. Integration of the exogenous DNA sequence into HPRT was assayed by high-throughput sequencing (Miseq, Illumina). IDS enzymatic activity was conducted by incubating cell lysate and supernatant with 4-Methylumbelliferyl α-L-Iduronate-2-Sulfate as described above for 4 hours at 37° C., then adding recombinant IDUA to cleave the substrate. Fluorescence was then measured at 450 nm emission after 365 nm excitation. Viability was measured with propidium iodide via flow cytometry. As a control, cells were also transfected with GFP encoding donors.

Figure 8B:
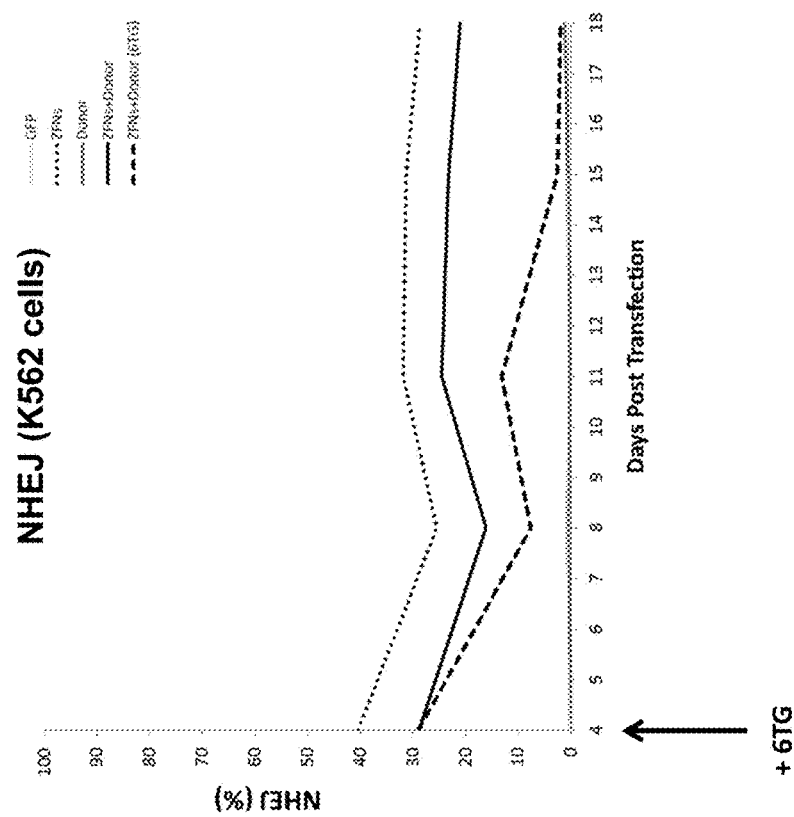
FIGS. 8A to 8D show graphs displaying the results of IDS transgene insertion into K562 cells.
Figure 8A:
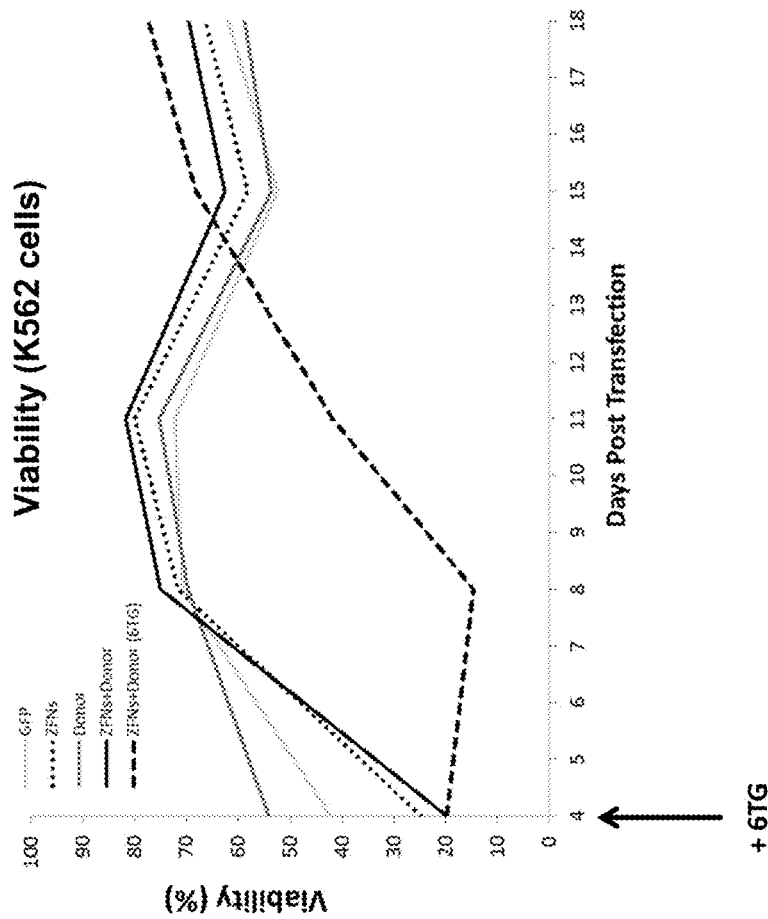
Figure 8D:
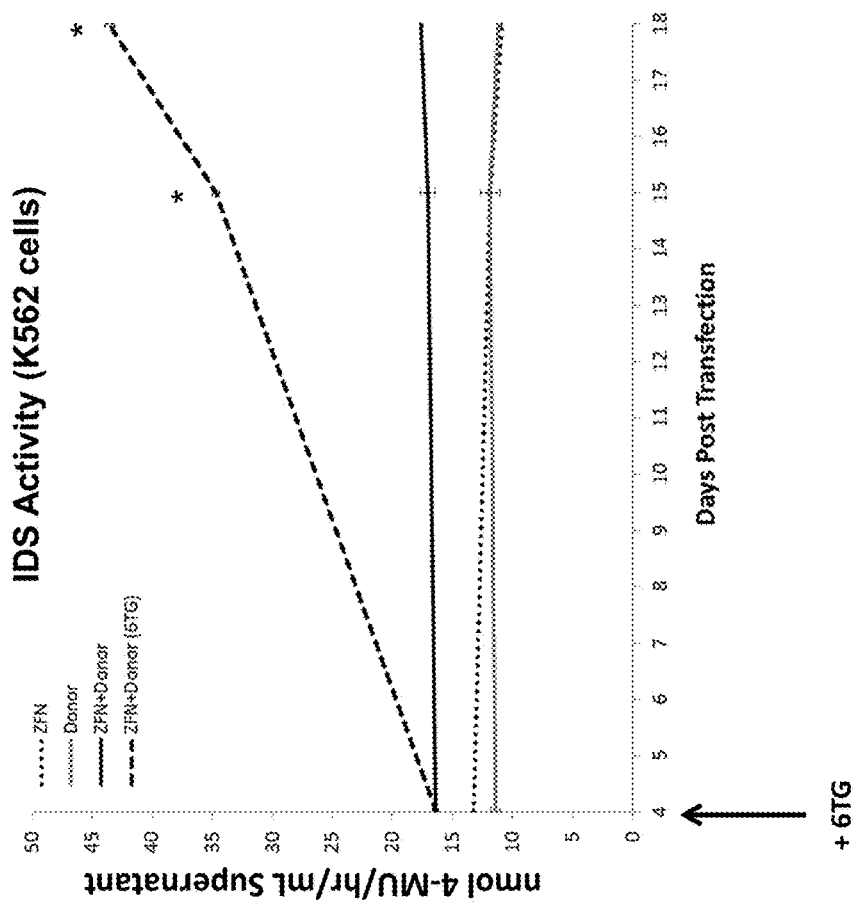
Figure 8C:
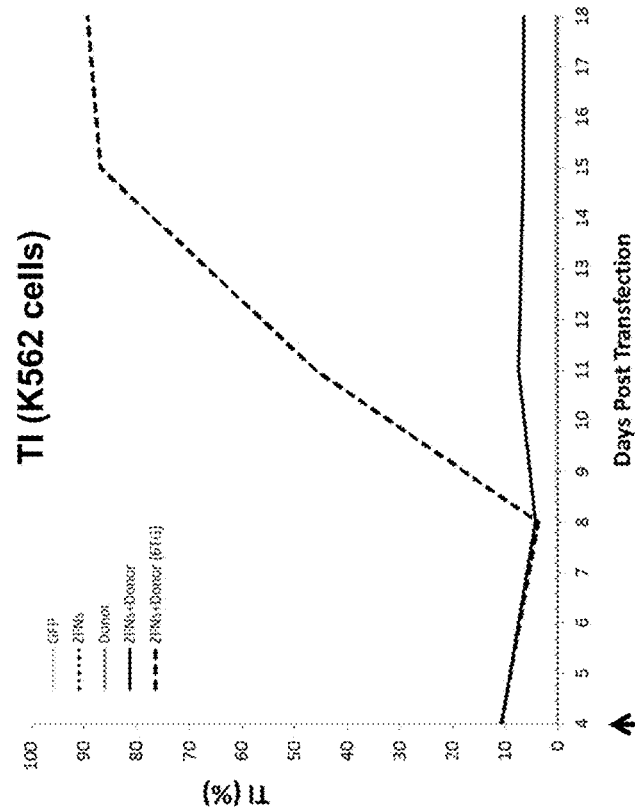

For the experiments done in K562 cells, viability of cells modified with a full IDS cDNA transgene downstream of a splice acceptor (SA) and 2A self-cleaving peptide sequence were assayed by flow cytometry with and without 6-TG selection (see FIG. 8A). The percent NHEJ (FIG. 8B) following nuclease cleavage was stable in cells grown without 6-TG selection, while cells modified with the ZFNs and the therapeutic IDS transgene donor showed decreased levels of NHEJ after 6-TG selection as assayed by MiSeq analysis (Illumina), done according to methods known in the art. Sequencing analysis also demonstrated that the levels of targeted integration of the IDS transgene reached 90% of all alleles after 6-TG selection (FIG. 8C). A 3-fold increase in IDS enzymatic activity in cell culture supernatant in the cells transfected with the IDS transgene was observed after two weeks of 6-TG selection (FIG. 8D, * P<0.05 compared to unselected controls).

Figure 9B:
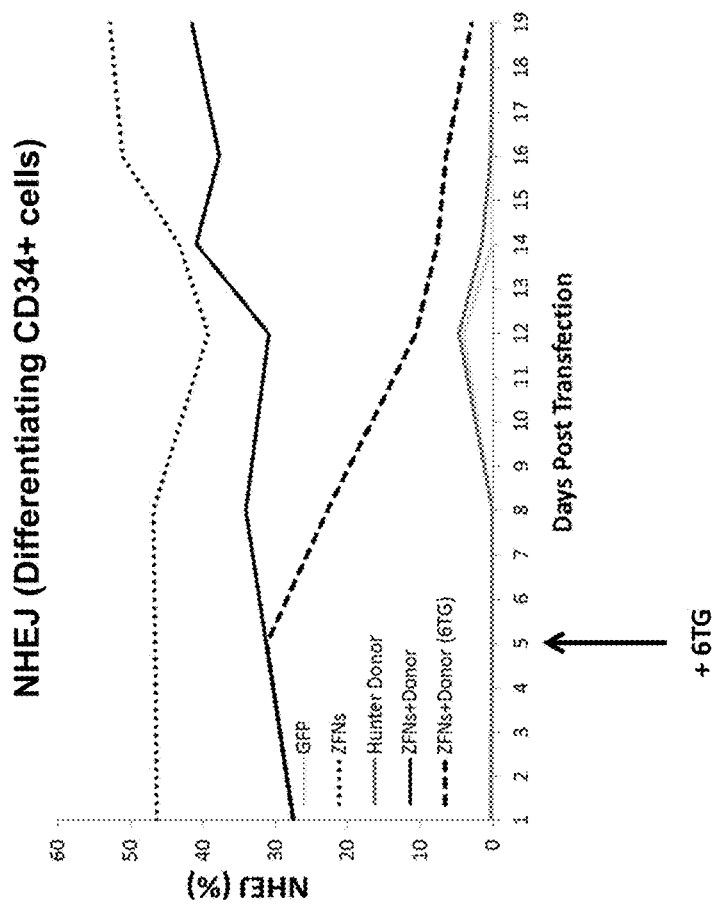
FIGS. 9A to 9D show graphs displaying the results of IDS transgene insertion into mobilized human CD34+ cells.
Figure 9A:
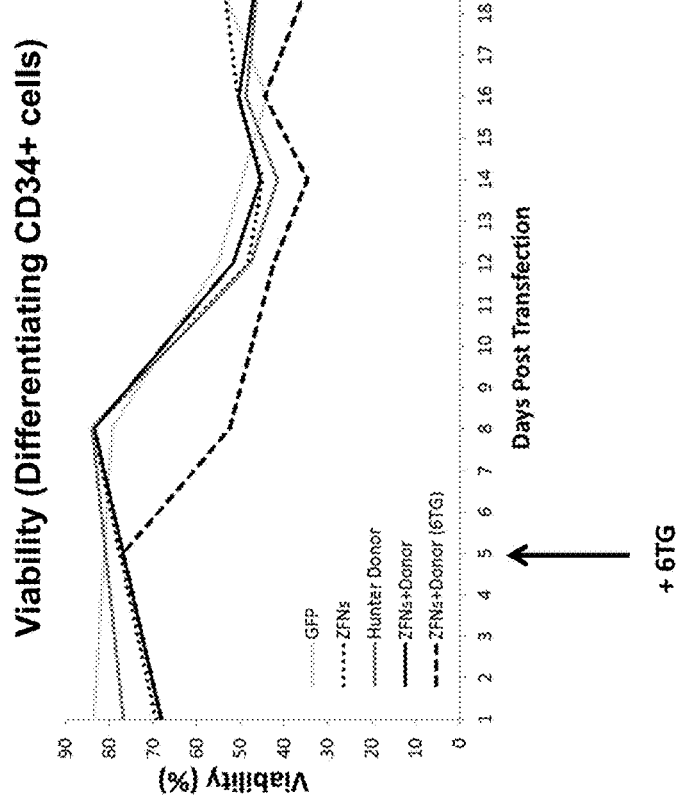
Figure 9D:
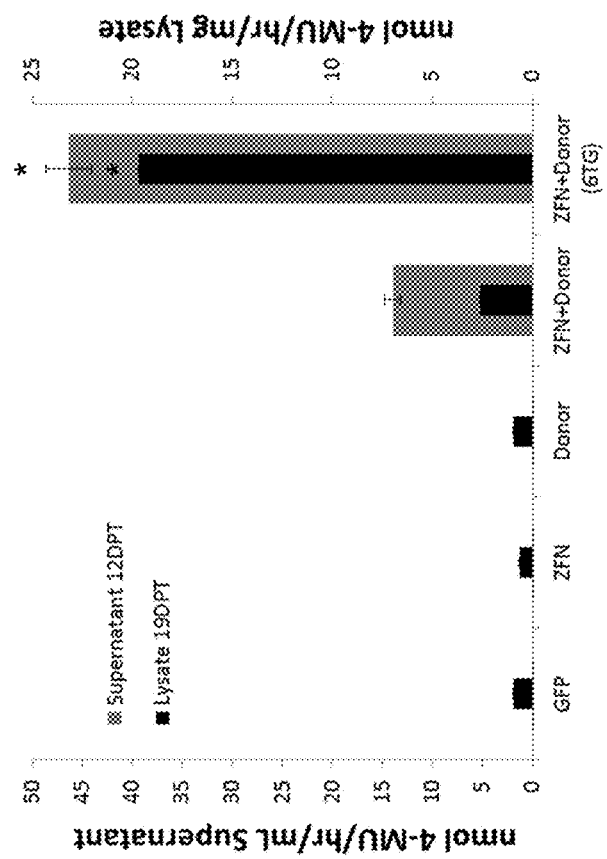
Figure 9C:
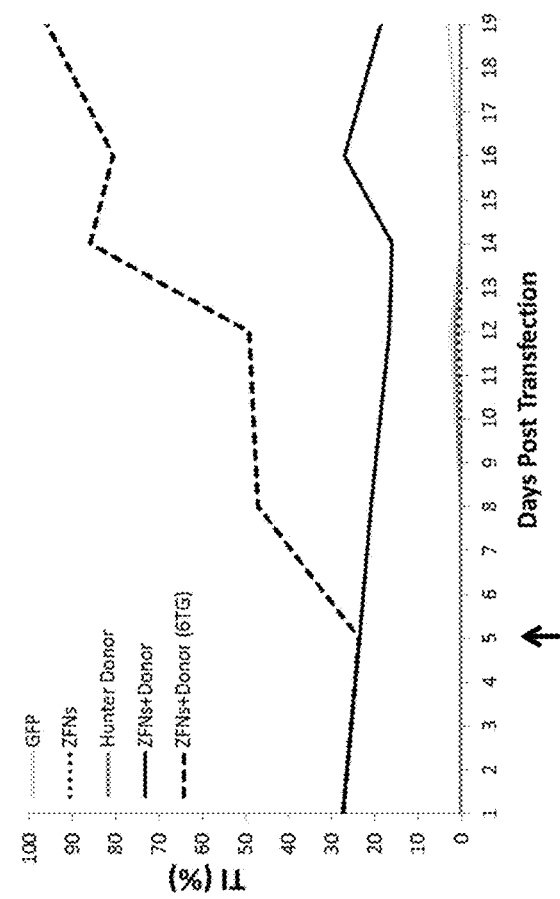

These experiments were also done in human mPB CD34+ cells. Viability and percent NHEJ were measured as described above (see FIGS. 9A and 9B) in cells undergoing erythroid differentiation. Relatively stable NHEJ in differentiating CD34+ cells modified with ZFNs without 6-TG selection was observed, while cells modified with ZFNs and therapeutic IDS transgene donor showed decreased levels of NHEJ after 6-TG selection as assayed by Miseq analysis. Levels of TI reach 96% of all alleles after 6-TG selection as assayed by sequence analysis in cells treated with the nuclease pair and the IDS transgene donor (FIG. 9C), and a 3-fold increase in IDS enzymatic activity in cell culture supernatant after one week of 6-TG selection, and an 8-fold increase in enzymatic activity in cell lysate after 2 weeks selection was observed (FIG. 9D, * P<0.05 compared to unselected controls).

Example 3: Detection of LSD Donor Transgenes In Vivo

A. Albumin

Donors for four lysosomal storage disease transgenes were constructed for the purpose of integrating into the mouse albumin gene in intron1: the transgenes were α-galactosidase A (GLA), Acid β-glucosidase (GBA), α-L-iduronidase (IDUA) and Iduronate-2-sulfatase (IDS), genes lacking in Fabry's, Gaucher's, Hurler's and Hunter's diseases, respectively.

The donors were then used in in vivo studies to observe integration of the transgenes into albumin. The murine albumin specific ZFNs and the donors were inserted all into AAV2/8 virus, and then were injected into mice. In these experiments, the virus was formulated for injection in D-PBS+35 mM NaCl, 5% glycerol and frozen prior to injection. The donor- and nuclease-containing viruses were mixed together prior to freezing. At Day 0, the virus preparation was thawed and administered to the mice by tail vein injection where the total injection volume was 200 µL. At the indicated times, the mice were sacrificed and then serum, liver and spleen were harvested for protein and DNA analysis by standard protocols. The dose groups are shown below in Table 7.

TABLE 7

Treatment groups for LSD transgene integration

| Group | Treatment | N/group/time point |
|---|---|---|
| 1 | murine Alb intron 1+ Fabry @ 1:5 ratio; ZFN @ 3.0e11, Donor @ 1.5e12 | 3 |
| 2 | murine Alb intron 1+ Hunters donor @ 1:5 ratio; ZFN @ 3.0e11, Donor @ 1.5e12 | 3 |
| 3 | murine Alb intron 1+ Hurlers donor @ 1:5 ratio; ZFN @ 3.0e11, Donor @ 1.5e12 | 3 |
| 4 | murine Alb intron 1 | 3 |
| 5 | Fabry donor only | 2 |
| 6 | Hunter's donor only | 2 |
| 7 | Hurler's donor only | 2 |

At day 30, liver homogenates were analyzed by Western blot analysis for the presence of the LSD proteins encoded by the donors. Liver homogenates were analyzed by Western blot using standard methodologies, using the following primary antibodies: α-Galactosidase A (Fabry's)-specific rabbit monoclonal antibody was purchased from Sino Biological, Inc.; Human α-L-Iduronidase (Hurler's)-specific mouse monoclonal antibody was purchased from R&D Systems; Human iduronate 2-Sulfatase (Hunter's)-specific mouse monoclonal was purchased from R&D Systems. The results showed expression, especially in the mice that received both the ZFN containing virus and the transgene donor containing virus.

The manner of integration of the donor DNA into the albumin locus was also investigated. In all of the transgene integrations, integration via both HRD and NHEJ mechanisms was observed.

Donor DNAs were also designed to include a tag sequence for later recognition of the protein using the tag specific antibodies. The donors were integrated as described above, and all were capable of integration as demonstrated by PCR.

B. HPRT

Donors as described herein are integrated into the mouse HPRT gene as described above in Example 3, part A for albumin. An exemplary treatment schedule for donors comprising one or more proteins lacking or deficient in an LSD is shown in Table 8:

TABLE 8

Treatment groups for LSD transgene integration

| Group | Treatment | N/group/ time point |
|---|---|---|
| 1 | murine HPRT intron 1+ donor (IDS, IDUA, α-Galactosidase A, alpha-glucosidase, etc.) @ 1:5 ratio; ZFN @ 3.0e11, Donor @ 1.5e12 | 3 |
| 2 | murine HPRT intron 1 | 3 |
| 3 | Donor only | 3 (per donor) |

At day 30, liver homogenates are analyzed by Western blot analysis for the presence of the protein encoded by the donor. Liver homogenates are analyzed by Western blot using standard methodologies, using the appropriate specific mouse monoclonal purchased from R&D Systems. The results show high IDS expression in the animals that receive both the ZFN and the IDS donor.

Example 4: Detection of hIDUA in MPS I Mice

Figures 10A, 10B, 10C:
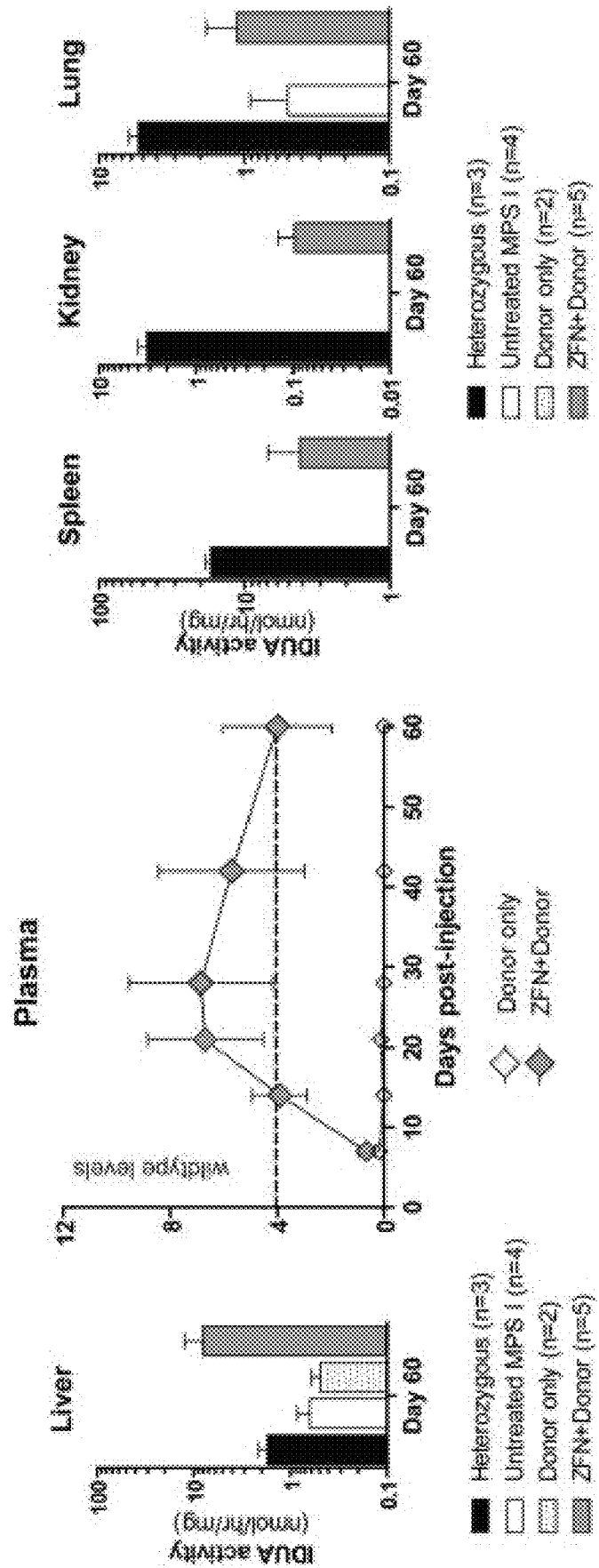
FIGS. 10A to 10C show graphs of IDUA activity in MPS1 mice treated with albumin ZFNs (AAV) and AAV-IDUA transgene donor.
Figures 11A, 11B, 11C:
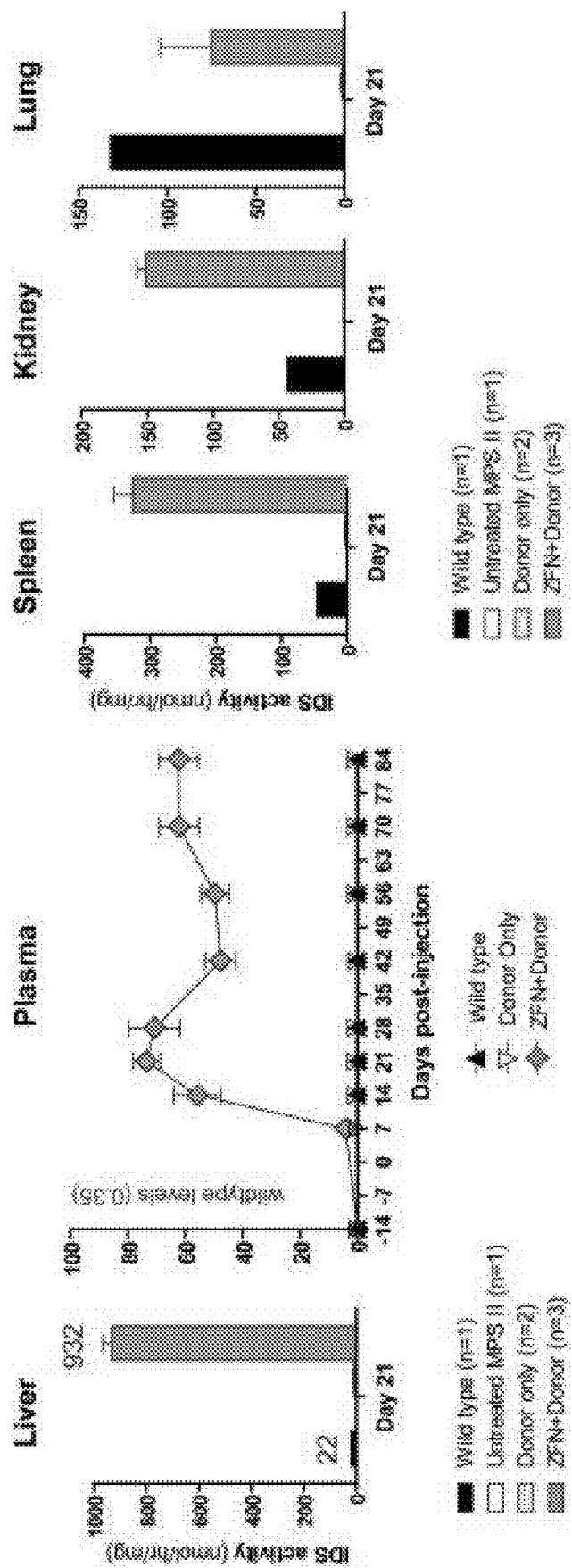
FIGS. 11A to 11C shows graphs of IDS activity in MPSII mice treated with albumin ZFNs (AAV) and AAV-IDS transgene donor.

We next sought to see if expression of human IDUA would be detectable in MPS I (Idua −/−) mice or MPS II (Ids Y/−). Idua −/− mice (see Hartung et al (2004) *Mol Ther* 9(6):866) and Ids Y/− mice (see e.g. Cardone et al (2006) *Hum Mol Genet* 15(7):1225) were treated as described above in Example 3 for the wild type mice using albumin targeted ZFNs. Human IDUA and human IDS were assayed as described above in several tissues in the animals, and the hIDUA was detected for at least 60 days post treatment (FIG. 10), while the hIDS was detectable for at least 84 days in the plasma (FIG. 11). Further, levels of GAG accumulation was measured in the urine and tissues of the animals as described previously (Hartung ibid).

Figure 13B:
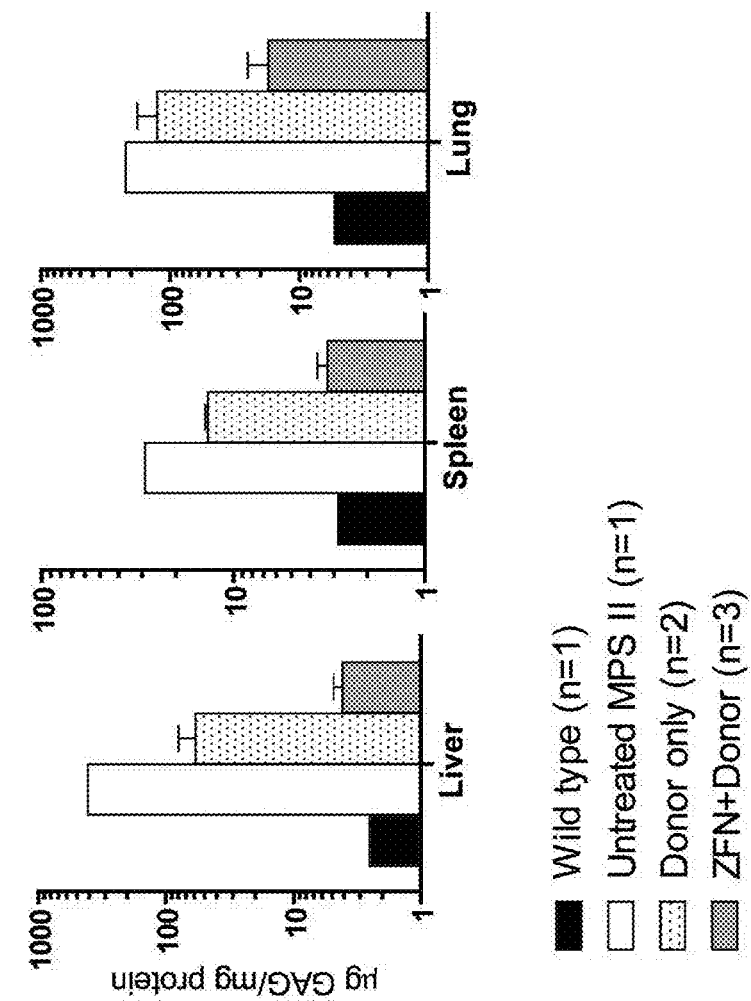
FIGS. 13A and 13B are graphs of GAG levels found in the urine and in the tissues of MPSII mice treated as in FIG. 11. Treatment of mice with ZFN and IDS donor was associated with lower GAG levels that untreated mice.
Figure 13A:
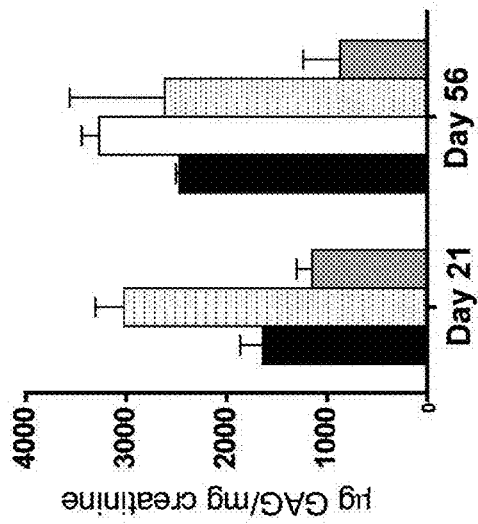

The results (FIG. 12 and FIG. 13) demonstrated that the AAV mediated delivery of ZFNs and the hIDUA transgene donor reduced GAG levels.

Example 5: Correction of Abnormal Neurologic Function in MPS I Mice

MPS I mice are evaluated for spatial memory and navigation using a Barnes Maze (see e.g. Sunyer et al (2007) Protocol Exchange doi:10.1038/nprot.2007.390). In brief, the maze has 20-40 holes around the periphery, where one hole leads to an escape box. Visual cues are placed on the walls of the maze and the mouse is trained to find the hole leading to the escape box. The basic function of Barnes maze is to measure the ability of a mouse to learn and remember the location of a target zone using a configuration of distal visual cues located around the testing area. After mastering the maze, the target hole is blocked off and the mouse is placed in the maze and its search strategies are analyzed to see how it searches for the hole to the escape box. The search strategies are defined as either 1) Direct (spatial) where the mouse moves directly or nearly directly to the hole, 2) Mixed, where the hole searches are separated by crossing through the center of the maze, or the mouse conducts an unorganized search, and 3) Serial, where the mouse finds the target hole by visiting the neighbor holes in either the clockwise or counterclockwise holes in a serial manner.

The MPS I mice treated with the albumin ZFNs and AAV-hIDUA donor are able to find the target hole faster and in a more organized manner than the control MPS1 mice.

All patents, patent applications and publications mentioned herein are hereby incorporated by reference in their entirety.

Although disclosure has been provided in some detail by way of illustration and example for the purposes of clarity of understanding, it will be apparent to those skilled in the art that various changes and modifications can be practiced without departing from the spirit or scope of the disclosure. Accordingly, the foregoing descriptions and examples should not be construed as limiting.

What is claimed is:

1. A method of treating a mouse or human with mucopolysaccharidosis type I (MPS I) or mucopolysaccharidosis type II (MPS II) disease, the method comprising
intravenously injecting first and second AAV vectors, encoding first and second ZFNs of a pair of zinc finger nucleases that cleave in an endogenous albumin gene, into the mouse or human with MPS I or MPS II disease;
intravenously injecting a third AAV vector comprising a transgene encoding (a) an iduronidase (IDUA) protein into the mouse or human with MPS I disease or (b) a DNA sequence encoding an iduronate sulfatase (IDS) protein into the mouse or human with MPS II disease, wherein the transgene is flanked by sequences having homology with the endogenous albumin gene;
wherein the first, second and third AAV vectors are delivered at a ratio of 1:1:8 and further wherein the transgene is integrated into the endogenous albumin gene in liver cells of the mouse or human and the liver cells express and secrete therapeutic amounts of the IDUA or IDS protein and a symptom of the MPS I or MPS II disease is treated in the mouse or human.

2. The method of claim 1, wherein the method treats neurological deficits associated with MPS I or MPS II disease.

3. The method of claim 1, wherein the method reduces GAG accumulation in the mouse or human.

4. The method of claim 1, wherein the AAV vectors are AAV2 and/or AAV6 vectors.

* * * * *

SEQUENCE LISTING

```
<160> NUMBER OF SEQ ID NOS: 26

<210> SEQ ID NO 1
<211> LENGTH: 25
<212> TYPE: DNA
<213> ORGANISM: Homo sapiens

<400> SEQUENCE: 1
ctgacctctt ctcttcctcc cacag                                    25

<210> SEQ ID NO 2
<211> LENGTH: 13
<212> TYPE: DNA
<213> ORGANISM: Homo sapiens

<400> SEQUENCE: 2
tttctctcca cag                                                 13

<210> SEQ ID NO 3
<211> LENGTH: 7
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 3

Arg Ser Asp Asn Leu Ser Glu
1               5

<210> SEQ ID NO 4
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gln Ser Gly Asn Leu Ala Arg
1               5

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Asp Arg Ser Asn Leu Ser Arg
1               5

<210> SEQ ID NO 6
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Trp Arg Ser Ser Leu Arg Ala
1               5

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Asp Ser Ser Asp Arg Lys Lys
1               5

<210> SEQ ID NO 8
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Thr Ser Gly Ser Leu Thr Arg
1               5
```

<210> SEQ ID NO 9
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Arg Ser Asp Ala Leu Ser Thr
1               5

<210> SEQ ID NO 10
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Gln Ser Ala Thr Arg Thr Lys
1               5

<210> SEQ ID NO 11
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Leu Arg His His Leu Thr Arg
1               5

<210> SEQ ID NO 12
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Gln Ala Gly Gln Arg Arg Val
1               5

<210> SEQ ID NO 13
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
tttcctgtaa cgatcgggaa ctggcatc                                    28

<210> SEQ ID NO 14
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
ctgaaggtgg caatggttcc tctctgct                                              28

<210> SEQ ID NO 15
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Thr Ser Gly Ser Leu Ser Arg
1               5

<210> SEQ ID NO 16
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Gln Ser Ser Asp Leu Ser Arg
1               5

<210> SEQ ID NO 17
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Arg Ser Asp His Leu Ser Gln
1               5

<210> SEQ ID NO 18
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Asp Asn Ser Asn Arg Ile Asn
1               5

<210> SEQ ID NO 19
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Gln Ser Gly Asp Leu Thr Arg
1               5

<210> SEQ ID NO 20
<211> LENGTH: 7
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 20

Arg Ser Asp Val Leu Ser Glu
1               5

<210> SEQ ID NO 21
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Arg Asn Gln His Arg Lys Thr
1               5

<210> SEQ ID NO 22
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Arg Ser Ala His Leu Ser Arg
1               5

<210> SEQ ID NO 23
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Asp Arg Ser Asp Leu Ser Arg
1               5

<210> SEQ ID NO 24
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
tgcacagggg ctgaagttgt cccacagg                                        28

<210> SEQ ID NO 25
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
tggccaggag gctggttgca aacatttt                                        28

<210> SEQ ID NO 26
<211> LENGTH: 9
```

```
<212> TYPE: PRT
<213> ORGANISM: Unknown
<220> FEATURE:
<223> OTHER INFORMATION: Description of Unknown:
      'LAGLIDADG' family peptide motif sequence

<400> SEQUENCE: 26

Leu Ala Gly Leu Ile Asp Ala Asp Gly
1               5
```